US 8,811,777 B2

(12) United States Patent
Younge et al.

(10) Patent No.: US 8,811,777 B2
(45) Date of Patent: Aug. 19, 2014

(54) OPTICAL FIBER SHAPE SENSING SYSTEMS

(75) Inventors: Robert G. Younge, Portola Valley, CA (US); Bhaskar S. Ramamurthy, Los Altos, CA (US); Neal A. Tanner, Mountain View, CA (US); Randall L. Schlesinger, San Mateo, CA (US); Eric Udd, Fairview, OR (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 34 days.

(21) Appl. No.: 13/594,629

(22) Filed: Aug. 24, 2012

(65) Prior Publication Data

US 2012/0323075 A1 Dec. 20, 2012

Related U.S. Application Data

(60) Division of application No. 13/073,295, filed on Mar. 28, 2011, now Pat. No. 8,515,215, which is a continuation of application No. 12/106,254, filed on Apr. 18, 2008, now Pat. No. 8,050,523.

(60) Provisional application No. 60/925,449, filed on Apr. 20, 2007, provisional application No. 60/925,472, filed on Apr. 20, 2007.

(51) Int. Cl.
*G02B 6/00* (2006.01)
*A61B 1/07* (2006.01)

(52) U.S. Cl.
USPC ............................................. 385/13; 600/182

(58) Field of Classification Search
USPC ............................................. 385/13; 600/182
See application file for complete search history.

(56) References Cited

U.S. PATENT DOCUMENTS

| 3,807,390 A | 4/1974 | Ostrowski et al. |
| 4,443,698 A | 4/1984 | Schiffner |
| 4,761,073 A | 8/1988 | Meltz et al. |
| 4,960,410 A | 10/1990 | Pinchuk |
| 4,996,419 A | 2/1991 | Morey |
| 5,007,705 A | 4/1991 | Morey et al. |
| 5,066,133 A | 11/1991 | Brienza |
| 5,118,931 A | 6/1992 | Udd et al. |
| 5,144,690 A | 9/1992 | Domash |
| 5,267,339 A | 11/1993 | Yamauchi et al. |
| 5,380,995 A | 1/1995 | Udd et al. |
| 5,397,891 A | 3/1995 | Udd et al. |

(Continued)

FOREIGN PATENT DOCUMENTS

| EP | 1103223 | 5/2001 |
| WO | WO 92/02276 | 2/1992 |

(Continued)

OTHER PUBLICATIONS

Eric Udd, "Good Sense", Spie's OE Magazine, Aug. 2002, pp. 27-30.

(Continued)

*Primary Examiner* — Jerry Rahll
(74) *Attorney, Agent, or Firm* — Pillsbury Winthrop Shaw Pittman, LLP

(57) ABSTRACT

A method for measuring bending is provided. The method includes receiving a reflected signal from a strain sensor provided on an optical fiber; determining a spectral profile of the reflected signal; and determining bending of the optical fiber based on a comparison of the spectral profile of the reflected signal with a predetermined spectral profile.

24 Claims, 46 Drawing Sheets

(56) References Cited

U.S. PATENT DOCUMENTS

| | | |
|---|---|---|
| 5,401,956 A | 3/1995 | Dunphy et al. |
| 5,477,856 A | 12/1995 | Lundquist |
| 5,563,967 A | 10/1996 | Haake |
| 5,591,965 A | 1/1997 | Udd |
| 5,627,927 A | 5/1997 | Udd |
| 5,630,783 A | 5/1997 | Steinberg |
| 5,713,946 A | 2/1998 | Ben-Haim |
| 5,738,096 A | 4/1998 | Ben-Haim |
| 5,798,521 A | 8/1998 | Froggatt |
| 5,828,059 A | 10/1998 | Udd |
| 5,833,608 A | 11/1998 | Acker |
| 5,843,076 A | 12/1998 | Webster, Jr. et al. |
| 5,876,325 A | 3/1999 | Mizuno et al. |
| 5,917,978 A | 6/1999 | Rutterman |
| 6,035,082 A | 3/2000 | Murphy et al. |
| 6,069,420 A | 5/2000 | Mizzi et al. |
| 6,083,170 A | 7/2000 | Ben-Haim |
| 6,144,026 A | 11/2000 | Udd et al. |
| 6,215,943 B1 | 4/2001 | Crotts et al. |
| 6,233,476 B1 | 5/2001 | Strommer et al. |
| 6,256,090 B1 | 7/2001 | Chen et al. |
| 6,266,551 B1 | 7/2001 | Osadchy et al. |
| 6,272,371 B1 | 8/2001 | Shlomo |
| 6,275,511 B1 | 8/2001 | Pan et al. |
| 6,275,628 B1 | 8/2001 | Jones et al. |
| 6,301,420 B1 | 10/2001 | Greenaway |
| 6,366,722 B1 | 4/2002 | Murphy et al. |
| 6,370,411 B1 | 4/2002 | Osadchy et al. |
| 6,389,187 B1 | 5/2002 | Greenaway et al. |
| 6,404,956 B1 | 6/2002 | Brennan, III et al. |
| 6,426,796 B1 | 7/2002 | Pulliam et al. |
| 6,470,205 B2 | 10/2002 | Bosselmann et al. |
| 6,471,710 B1 | 10/2002 | Bucholtz |
| 6,545,760 B1 | 4/2003 | Froggatt et al. |
| 6,571,639 B1 | 6/2003 | May et al. |
| 6,611,700 B1 | 8/2003 | Vilsmeier et al. |
| 6,626,899 B2 | 9/2003 | Houser et al. |
| 6,671,055 B1 | 12/2003 | Wavering et al. |
| 6,716,178 B1 | 4/2004 | Kilpatrick et al. |
| 6,817,974 B2 | 11/2004 | Cooper et al. |
| 6,826,343 B2 | 11/2004 | Davis et al. |
| 6,850,817 B1 | 2/2005 | Green |
| 6,868,195 B2 | 3/2005 | Fujita |
| 6,876,786 B2 | 4/2005 | Chliaguine |
| 6,888,623 B2 | 5/2005 | Clements |
| 6,898,337 B2 | 5/2005 | Averett et al. |
| 6,905,460 B2 | 6/2005 | Wang et al. |
| 6,923,048 B2 | 8/2005 | Willsch et al. |
| 6,949,105 B2 | 9/2005 | Bryan et al. |
| 6,963,792 B1 | 11/2005 | Green |
| 6,965,708 B2 | 11/2005 | Luo et al. |
| 6,987,897 B2 | 1/2006 | Elster et al. |
| 7,010,182 B2 | 3/2006 | Pennington |
| 7,038,190 B2 | 5/2006 | Udd et al. |
| 7,042,573 B2 | 5/2006 | Froggatt |
| 7,046,866 B2 | 5/2006 | Sahlgren et al. |
| 7,154,081 B1 | 12/2006 | Friedersdorf et al. |
| 7,248,944 B2 | 7/2007 | Green |
| 7,320,700 B2 | 1/2008 | Cooper et al. |
| 7,330,245 B2 | 2/2008 | Froggatt |
| 7,343,195 B2 | 3/2008 | Strommer et al. |
| 7,371,210 B2 | 5/2008 | Brock et al. |
| 7,538,883 B2 | 5/2009 | Froggatt |
| 7,561,276 B2 | 7/2009 | Boyd |
| 7,618,371 B2 | 11/2009 | Younge |
| 7,742,805 B2 | 6/2010 | Furnish |
| 7,772,541 B2 | 8/2010 | Froggatt et al. |
| 7,781,724 B2 | 8/2010 | Childers |
| 7,789,874 B2 | 9/2010 | Yu |
| 7,789,875 B2 | 9/2010 | Brock et al. |
| 8,050,523 B2 | 11/2011 | Younge et al. |
| 2002/0064330 A1 | 5/2002 | Croteau et al. |
| 2003/0135204 A1 | 7/2003 | Lee et al. |
| 2004/0034365 A1 | 2/2004 | Lentz et al. |
| 2005/0036140 A1 | 2/2005 | Elster et al. |
| 2005/0197530 A1 | 9/2005 | Wallace |
| 2005/0201664 A1 | 9/2005 | Udd et al. |
| 2005/0222554 A1 | 10/2005 | Wallace et al. |
| 2006/0013523 A1 | 1/2006 | Childlers et al. |
| 2006/0036164 A1 | 2/2006 | Wilson |
| 2006/0036213 A1 | 2/2006 | Viswanathan |
| 2006/0057560 A1 | 3/2006 | Hlavka et al. |
| 2006/0084945 A1 | 4/2006 | Moll |
| 2006/0095022 A1 | 5/2006 | Moll |
| 2006/0100610 A1 | 5/2006 | Wallace et al. |
| 2006/0111692 A1 | 5/2006 | Hlavka et al. |
| 2006/0200026 A1 | 9/2006 | Wallace et al. |
| 2006/0200049 A1 | 9/2006 | Leo et al. |
| 2006/0276775 A1 | 12/2006 | Rosenberg et al. |
| 2007/0043338 A1 | 2/2007 | Moll et al. |
| 2007/0060847 A1 | 3/2007 | Leo et al. |
| 2007/0156019 A1 | 7/2007 | Larkin et al. |
| 2007/0156123 A1 | 7/2007 | Moll et al. |
| 2007/0197896 A1 | 8/2007 | Moll et al. |
| 2007/0197939 A1 | 8/2007 | Wallace et al. |
| 2007/0233044 A1 | 10/2007 | Wallace et al. |
| 2007/0265503 A1 | 11/2007 | Schlesinger et al. |
| 2007/0293724 A1 | 12/2007 | Saadat et al. |
| 2008/0009750 A1 | 1/2008 | Aeby et al. |
| 2008/0015445 A1 | 1/2008 | Saadat et al. |
| 2008/0218770 A1 | 9/2008 | Moll et al. |
| 2008/0243064 A1 | 10/2008 | Stahler et al. |
| 2008/0249536 A1 | 10/2008 | Stahler et al. |
| 2008/0262480 A1 | 10/2008 | Stahler et al. |
| 2008/0262513 A1 | 10/2008 | Stahler et al. |
| 2008/0300592 A1 | 12/2008 | Weitzner et al. |
| 2009/0123111 A1 | 5/2009 | Udd |
| 2009/0138025 A1 | 5/2009 | Stahler et al. |
| 2011/0172680 A1 | 7/2011 | Younge et al. |

FOREIGN PATENT DOCUMENTS

| | | |
|---|---|---|
| WO | WO 01/33165 | 5/2001 |
| WO | WO 02/19898 | 3/2002 |
| WO | WO 02/47751 | 6/2002 |
| WO | WO 03/006595 | 8/2003 |
| WO | WO 04/001469 | 12/2003 |
| WO | WO 2005/087128 | 9/2005 |
| WO | WO 2006/092707 | 9/2006 |
| WO | WO 2006/099056 | 9/2006 |
| WO | WO 2007/015139 | 2/2007 |
| WO | WO 2007/045028 | 4/2007 |
| WO | WO 2007/109778 | 9/2007 |
| WO | WO 2008/094949 | 8/2008 |
| WO | WO 2008/131303 | 10/2008 |

OTHER PUBLICATIONS

Roger Duncan, "Sensing Shape: Fiber-Bragg-grating sensor arrays monitor shape at a high resolution", Spie's OE Magazine, Sep. 2005, pp. 18-21.

G.M.H. Flockhart et al., "Two-axis bend measurement with Bragg gratings in multicore optical fiber", Optics Letters, Mar. 15, 2003, pp. 387-389, vol. 28 No. 6, Optical Society of America.

Alan D. Kersey et al., "Fiber Grating Sensors", Journal of Lightwave Technology, Aug. 1997, pp. 1442-1463 vol. 15 No. 8.

Mark Froggatt et al., "Distributed measurement of static strain in an optical fiber with multiple Bragg gratings at nominally equal wavelengths", Applied Optics, Apr. 1, 1998, pp. 1741-1746, vol. 37 No. 10.

Raymond M. Measaures, "Fiber Optic Strain Sensing", Fiber Optic Smart Structures, 1995, pp. 171-247, John Wiley & Sons Inc.

C.M. Lawrence et al., "A Fiber Optic Sensor for Transverse Strain Measurement", Experimental Mechanics, Sep. 1999, pp. 202-209, vol. 39 No. 3.

File history of U.S. Appl. No. 11/450,072, filed Jun. 9 2006, published as 2008-0009750, on Jan. 10, 2008 (submitted via EFS-Web as k_NPL-part-1, part-2, part-3).

Meng-Chou Wu et al., "Fabrication of self-apodized short-length fiber Bragg gratings", Applied Optics, Sep. 1, 2003, pp. 5017-5023, vol. 42, No. 25.

(56) References Cited

OTHER PUBLICATIONS

Kenneth O. Hill et al., "Fiber Bragg Grating Technology Fundamentals and Overview", Journal of Lightwave Technology, Aug. 1997, pp. 1263-1276, vol. 15 No. 8.

Yan Zhang et al., "Fiber-Bragg-grating-based seismic geophone for oil/gas prospecting", Optical Engineering, Aug. 2006, pp. 84404-1-84404-4, vol. 45 No. 8.

Matthew T. Raum, "Error Analysis of Three Dimensional Shape Sensing Algorithm", Virginia Tech, Apr. 26, 2005.

Mark E. Froggatt et al., "Distributed Fiber-Optic Strain and Temperature Sensors Using Photoinduced Bragg Gratings", Feb. 1995, pp. 1741-1746, Blacksburg Virginia.

Claire Davis, "Strain Survey of an F/A-18 Stabilator Spindle Using High Density Bragg Grating Arrays", Feb. 2005, Australia.

Zhang Lun-Wei, "Novel shape detection systems based on FBG sensor net for intelligent endoscope", Journal of Shanghai University (English Edition), Apr. 2006, pp. 154-155, vol. 10 No. 2.

V.V. Wong et al., "Distributed Bragg grating integrated-optical filters: Synthesis and fabrication", American Vacuum Society, Nov./Dec. 1995, pp. 2859-2864, vol. 13 No. 6.

Youngmin Kim et al., "Micromachined Fabry-Perot Cavity Pressure Transducer", IEEE Photonics Technology Letters, Dec. 1995, pp. 1471-1473, vol. 7 No. 12.

John W. Berthold III, "Historical Review of Microbend Fiber-Optic Sensors", Journal of Lightwave Technology, Jul. 1995, pp. 1193-1199, vol. 13 No. 7.

R. Posey Jr. et al., "Strain sensing based on coherent Rayleigh scattering in an optical fibre", Electronics Letters, Sep. 28, 2000, pp. 1688-1689, vol. 36 No. 20.

Kazuo Notate et al., "Proposal and experimental verification of Bragg wavelength distribution measurement within a long-length FBG by synthesis of optical coherence function" Optics Express, May 26, 2008, pp. 7881-7887, vol. 16 No. 11.

M.M. Ohn et al., "Arbitrary strain profile measurement within fibre gratings using interferometric Fourier transform technique", Electronics Letters, Jul. 3, 1997, pp. 1242-1243, vol. 33 No. 14.

Zhang Lunwei et al., "FBG Sensor Devices for Spatial Shape Detection of Intelligent Colonscope", Apr. 2004, pp. 835-840, New Orleans Louisiana.

Craig M. Lopatin et al., "Distributed Measurement of Strain in Smart Materials Using Rayleigh Scattering", 32 International SAMPE Technical Conference, Nov. 2000, pp. 231-241.

X.G. Tian et al., "Torsion Measurement Using Fiber Bragg Grating Sensors", Experimental Mechanics, Sep. 2001, pp. 248-253, vol. 41 No. 3.

Garret Lee et al., "Intraoperative Use of Duel Fiberoptic Catheter for Simultaneous In Vivo Visualization and Laser Vaporization of Peripheral Atherosclerotic Obstructive Disease", Catheterization and Cardiovascular Diagnosis, 1984, pp. 11-16.

Mark Froggatt et al., "High-spatial-resolution distributed strain measurement in optical fiber with Rayleigh scatter", Applied Optics, Apr. 1, 1998, pp. 1735-1740, vol. 37 No. 10.

Gary A. Miller et al., "Shape Sensing Using Distributed Fiber Optic Strain Measurements", Second European Workshop on Optical Fibre Sensors, Proceedings of the SPIE, Jun. 2004, pp. 528-531, vol. 5502.

M. J. Gander et al., "Measurement of bending in two dimensions using multicore optical fibre", European Workshop on Optical Fibre Sensors, Jun. 1998, p. 64-68, Proc. SPIE vol. 3483.

Ad A. M. Mass, "Shape measurement using phase shifting speckle interferomentry", Laser Interferometry IV: Computer-Aided Interferometry, Jan. 1, 1992, pp. 558-568, Proceedings SPIE vol. 1553.

Roger R. Duncan et al., "Use of high spatial resolution fiber-optic shape sensors to monitor the shape of deployable space structures" Space Technology and Applications Int.Forum-Staif 2005: Conf. Thermophys in Micrograv;Conf Comm/Civil Next Gen.Space Transp; 22nd Symp Space Nucl.Powr Propuls.;Conf.Human/Robotic Techn.Nat'l Vision Space Expl.; 3rd Symp Space Colon.; 2nd Symp. New Frontiers. AIP Conference Proceedings, Feb. 2005, pp. 880-886, vol. 746.

Joeseph R. Blandino et al., "Three-dimensional shape sensing for inflatable booms", 46th AIAA/ASME/ASCE/AHS/ASC Structures, Structural Dynamics & Materials Conference, Austin, Texas, Conference Dates : Apr. 18-21, 2005, pp. 1-10.

Roger R. Duncan et al., "Characterization of a fiber optic shape and position sensor" Conference Title: Smart Structures and Materials 2006: Smart Sensor Monitoring Systems and Applications; San Diego, CA, Conference Date: Monday Feb. 27, 2006, Published in: Proc. SPIE, vol. 6167, 616704 (2006); doi:10.1117/12.658535, Online Publication Date: Mar. 30, 2006.

A. F. Abouraddy et al., "Towards multimaterial multifunctional fibres that see, hear, sense, and communicate", Nature Materials 6, Publication date: May 2007, pp. 336-347.

Roger R. Duncan et al., "High-accuracy fiber-optic shape sensing" Conference Title: Sensor Systems and Networks: Phenomena, Technology, and Applications for NDE and Health Monitoring 2007, San Diego, California, USA, Conference Date: Monday Mar. 19, 2007, Published in: Proc. SPIE, vol. 6530, 65301S (2007); doi:10.1117/12.720914, Online Publication Date: Apr. 10, 2007.

Eric Udd et al., "Progress on developing a multiaxis fiber optic strain sensor" Third Pacific Northwest Fiber Optic Sensor Workshop, Publication Date: Sep. 2, 1997, pp. 50-56, Proceedings SPIE vol. 3180.

Eric Udd et al., "Multidimensional strain field measurements using fiber optic grating sensors", Smart Structures and Materials 2000: Sensory Phenomena and Measurement Instrumentation for Smart Structures and Materials, Publication Date: Jun. 12, 2000, pp. 254-262, Proceedings SPIE vol. 3986.

Juncheng Xu et al., "Miniature fiber optic pressure and temperature sensors", Fiber Optic Sensor Technology and Applications IV, Publication Date: Nov. 10, 2005, pp. 600403-1-600403-6, Proceedings SPIE vol. 6004.

M. Lequime et al., "Fiber optic pressure and temperature sensor for down-hole applications", , Fiber Optic Sensors: Engineering and Applications, Publication Date: Aug. 1, 1991,pp. 244-249, Proceedings SPIE vol. 1511.

T. Sato et al., "Ground strain measuring system using optical fiber sensors", Smart Structures and Materials 2000: Sensory Phenomena and Measurement Instrumentation for Smart Structures and Materials, Publication Date: Jun. 12, 2000, pp. 180-190, Proceedings SPIE vol. 3986.

Sandra M. Klute et al., "Fiber-optic shape sensing and distributed strain measurements on a morphing chevron", 44th AIAA Aerospace Sciences Meeting and Exhibit, Conference dates: Jan. 9-12, 2006, pp. 1-25, Reno Nevada.

Roger R. Duncan et al., "Fiber-optic shape and position sensing", Proceedings of the 5th International Conference on Structural Health Monitoring (2005), Structural Health Monitoring, 2005: Advancements and Challenges for Implementation, Copyright 2005.

Mark Froggatt, Intracore and extracore examination of fiber gratings with coherent, Thesis (PhD). The University of Rochester, Jun. 2001, pp. 6540, Source DAI-B 61/12.

Brooks A. Childers et al., "Recent development in the application of optical frequency domain reflectometry to distributed Bragg grating sensing", Fiber Optic Sensor Technology and Applications, pp. 19-31, Feb. 2002, Proc. SPIE vol. 4578.

J. Grant et al., "Investigation of structural properties of carbon-epoxy composites using fiber-bragg gratings", Applications of Photonic Technology 5, Publication Date: Feb. 17, 2003, pp. 191-199, Proceedings SPIE vol. 4833.

Roger R. Duncan et al., "A distributed sensing technique for aerospace applications", 42nd AIAA Aerospace Sciences Meeting and Exhibit, Conference dates: Jan. 5-8, 2004, Reno, Nevada.

S. Huang et al., "Continuous arbitrary strain profile measurements with fiber bragg gratings", Smart Materials and Structures, Publication Date: Apr. 1998, pp. 248-256, vol. 7, No. 2.

Youngmin Kim et al., "Design for manufacture of micromachined Fabry-Perot cavity-based sensors", Sensors and actuators. A, Physical, ISSN 0924-4247, 1995, pp. 141-146 [(article)], vol. 50, n°1-2.

Eric Pinet et al., "True challenges of disposable optic fiber sensors for clinical environment", Third European Workshop on Optical Fibre Sensors, Antonello Cutolo; Brian Culshaw; José Miguel López-Higuera, Editors, 66191Q, Publication Date: Jul. 2, 2007, pp. 66191Q-1-66191Q-4, Proceedings SPIE vol. 6619.

(56) References Cited

OTHER PUBLICATIONS

Brian J. Soller et al., "Optical frequency domain reflectometry for single- and multi-mode avionics fiber-optics applications", Avionics Fiber-Optics and Photonics, Publication Date: Sep. 12-14, 2006, pp. 38-39, IEEE Conference.

Jin-Seok Heo et al., "Design of TR-EFPI fiber optic pressure sensor for the medical application", International Journal of Human-friendly Welfare Robotic Systems, Published : 2002, pp. 2-7, vol. 3, No. 2.

Matt Raum et al "Performance Analysis of a Fiber-Optic Shape Sensing Systems" cited as reference of 'Fiber-optic shape sensing and distributed strain measurements on a morphing chevron', Collection of Technical papers—$44^{th}$ AIAA, vol. 10, 2006, pp. 7460-7482.

Distributed Sensing System Sensor Array Specification, www.lunainnovations.com, pp. 1-3.

Kirby et al, "Optimal sensor layout for shape estimation form strain sensors", Smart Structures and Materials, Mar. 1995, pp. 367-376, Proc. SPIE vol. 2444.

Maas, "Shape Measurement using phase shifting speckle interferometry", Laser Interferometry IV, Jan. 1992, pp. 558-568, SPIE vol. 1553.

Davis et al, "Fiber-optic bragg grating array for shape and vibration mode sensing", May 1994, pp. 94-102, Proceedings SPIE vol. 2191.

Gander et al, "Bend Measurements using multicore fiber", Jan. 2000, pp. 166-169, Electronics Letters, 36 Issue 2.

Gander et al, "Bend Measurement using multicore optical fiber", Proceedings of OFS-12, Oct. 1997, pp. 166-169.

Kreger et al, "Distributed strain and temperature sensing in plastic optical fiber using Rayleigh scattering", Apr. 2009, pp. 73160A-1-73160A-8, Proc. of SPIE 7316.

Kreger et al, "High-resolution extended distance distributed fiber-optic sensing using Rayleigh backscatter", Apr. 2007, pp. 65301R-1-65301R-30, Proc. of SPIE 6530.

Danisch et al, "Spatially continuous six degree of freedom position and orientation sensor", Sensor Review, 1999, pp. 106-112, vol. 19.

Gifford et al, "Swept-wavelength interferometric interrogation of fiber Rayleigh scatter for distributed sensing applications", 2007, pp. 67700F-1-67700F-9, Proc. of SPIE col. 6770.

Miller et al, "Fiber-optic shape sensing for flexible structures", Feb. 1989, pp. 399-404, SPIE 1170.

Morey, "Fiber-optic bragg grating sensors", 1989, pp. 98-107, SPIEL col. 1169.

Trimble, "Successful fiber sensor for medical applications", May 1993, pp. 147-150, Proceedings SPIE vol. 1886.

Danish et al, "Bend-enhanced fiber optic sensors in teleoperation application", Sep. 1993, pp. 73-85, Proc. SPIE vol. 2070.

Grossman et al, "Development of microbend sensors for pressure, load, displacement measurements in civil engineering", May 1994, pp. 112-125, Proceedings SPIE vol. 2191.

Lawrence et al, "Multi-parameter sensing with fiber bragg gratings", 1996, pp. 24-31, Proceedings of SPIE vol. 2872.

Schulz et al, "Health monitoring of adhesive joints using multi-axis fiber grating strain sensor system", Jan. 1999, pp. 41-52, Proceedings of SPIE vol. 3586.

"Fiber Optic Interferometer Fabry-Perot", http://physics-animations.com/sensors/English/interf.htm, pp. 1-5.

Katsuki et al, "The Experimental Research on the Health Monitoring of the Concrete Structures Using Optical Fiber Sensor", BAM International Symposium (NDT-CE 2003), Non-destructive Testing in Civil Engineering, Sep. 16-19, 2003.

Hayano et al., "Structural Health Monitoring System Using FBG Sensor Simultaneous Detection of Acceleration and Strain", Department of System Design Engineering, Keio University, pp. 1-10.

Ye et al., "A Polarization-maintaining Fiber Bragg Grating Interrogation System for Multi-Axis Strain Sensing", Measurement Science and Technology, Aug. 7, 2002, pp. 1446-1449.

Wippich et al., "Tunable Lasers and Fiber-Bragg-Grating Sensors", The Industrial Physicist, Jun./Jul. 2003, pp. 24-27.

Sorin, W.V. "Survey of Different Techniques", Optical Reflectometry for Component Characterization, Fiber Optic Test and Measurement, Dennis Derickson (editor), 1997, , Chapter 10, Section 10.5, pp. 424-429.

Schulz et al., "Advanced Fiber Grating Strain Sensor Systems for Bridges, Structures, and Highways", Proceedings of SPIE 3325, 212 (1998).

Schreiber et al., "Stress-induced Birefringence in Large-mode-area Micro-structured Optical Fibers", Optics Express, May 16, 2005, pp. 3637-3646, vol. 13 No. 10.

Capouilliet al., "A Fiber Bragg Grating Measurement System for Monitoring Optical Fiber Strain", IWCS/FOCUS Internat conference Nov. 12-15, 2001, pp. 240-248.

Xue et al., "Simultaneous Measurement of Stress and Temperature with a Fiber Bragg Grating Based on Loop Thin-Wall Section Beam", Mar. 2, 2006, pp. 1-16.

Soller et al., "High Resolution Optical Frequency Domain Reflectometry for Characterization of Components and Assemblies", Optics Express, Jan. 24, 2005, pp. 666-674, vol. 13 No. 2.

Satava, "How the Future of Surgery is Changing: Robotics, Telesurgery, Surgical Simulators and Other Advanced Technologies", May 2006, pp. 2-21.

Janssen et al., "Signal Averaging in the Undergraduate Laboratory", Europe Journal of Physics, 9 (1988), pp. 131-134.

Danisch et al., "Bend Enhanced Fiber Optic Sensors in a Teleoperation Application", Fiber Optic and Laser Sensors XI, 1993, pp. 73-85, SPIE vol. 2070.

PCT International Search Report for PCT/US2007/064728, Applicant Hansen Medical, Inc., Forms PCT/ISA/210 and 220, dated Jul. 31, 2007 (7 pages).

PCT Written Opinion of the International Search Authority for PCT/US2007/064728, Applicant: Hansen Medical, Inc., Form PCT/ISA/237, dated Jul. 31, 2007 (9 pages).

File History for related application U.S. Appl. No. 11/690,116, filed Mar. 22, 2007, Inventor Schlensinger et at, (43 pages total) including: Office Action dated Apr. 28, 2010 Amendment and Response to Office Action dated Apr. 28, 2010, submitted on Aug. 30, 2010 Final Office Action dated Nov. 19, 2010.

PCT Invitation to Pay Additional Fees from the International Search Authority for PCT/US2008/082236, Applicant Hansen Medical Inc., Form PCT/ISA/206 and Annex to Form PCT/ISA/206, dated Jul. 6, 2009 (9 pages).

Turan Erdogan, "Fiber Grating Spectra", Journal of Lightwave Technology, vol. 15, No. 8, Aug. 1997, IEEE Service Center, New York, NY (18 pages).

PCT International Search Report and Written Opinion for PCT/US2008/082236, Applicant Hansen Medical, Inc., Forms PCT/ISA/210, 220, and 237 dated Oct. 16, 2009 (19 pages).

File History for related application U.S. Appl. No. 12/236,478, filed Sep. 23, 2008, Inventor Udd, (35 pages total) including: Office Action, restriction requirement, dated Dec. 1, 2009 Response to Office Action dated Dec. 1, 2009, submitted on Dec. 29, 2009 Office Action dated Apr. 6, 2010 Amendment and Response to Office Action dated Apr. 6, 2010, submitted on Oct. 6, 2010.

PCT International Search Report and Written Opinion for PCT/US2008/001505, Applicant Hansen Medical, Inc., Forms PCT/ISA/210, 220 and 237, dated Dec. 3, 2008 (12 pages).

PCT International Search Report and Written Opinion of the International Search Authority for PCT/US2008/060936, Applicant Hansen Medical, Inc., mailed Nov. 6, 2008 (16 pages).

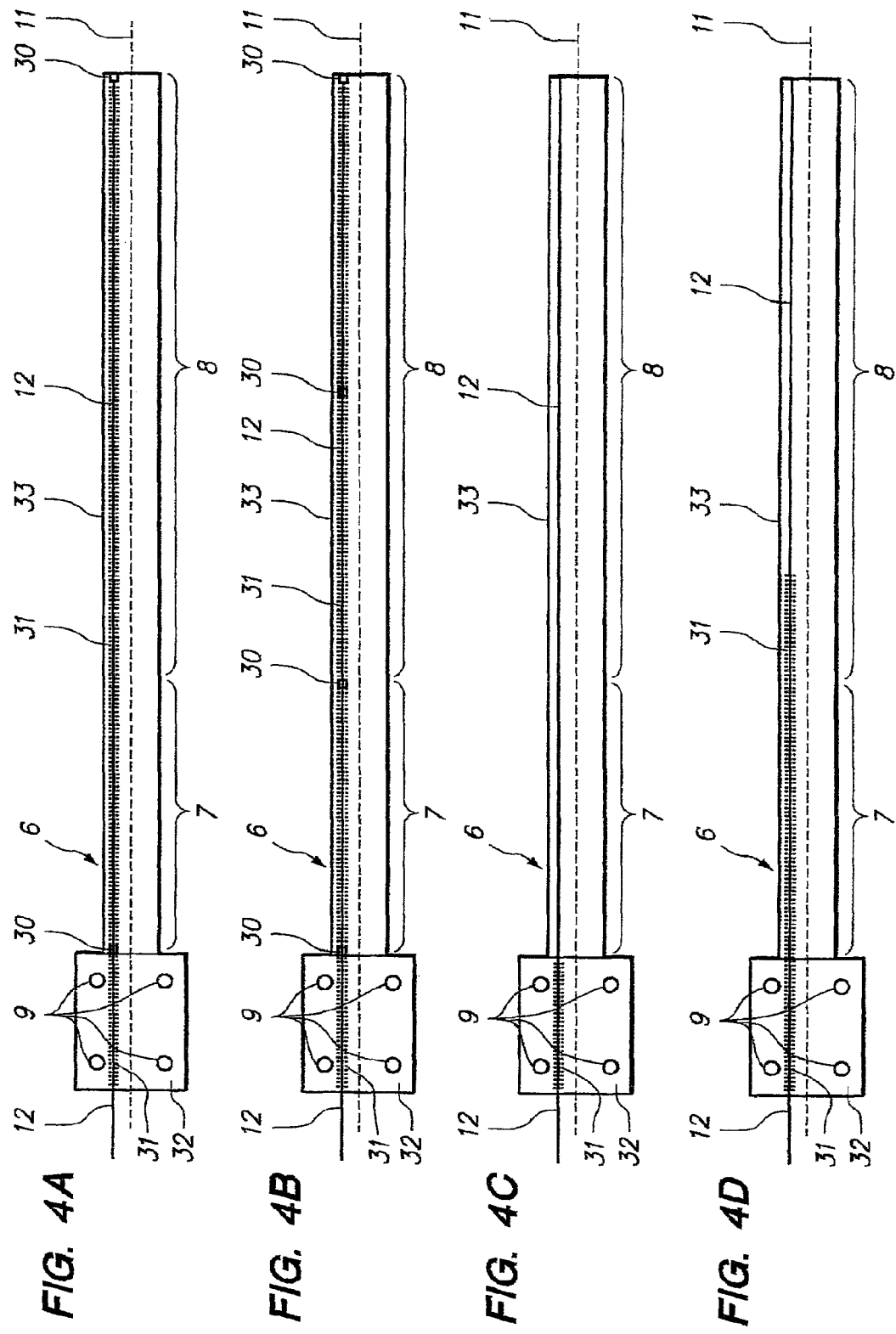

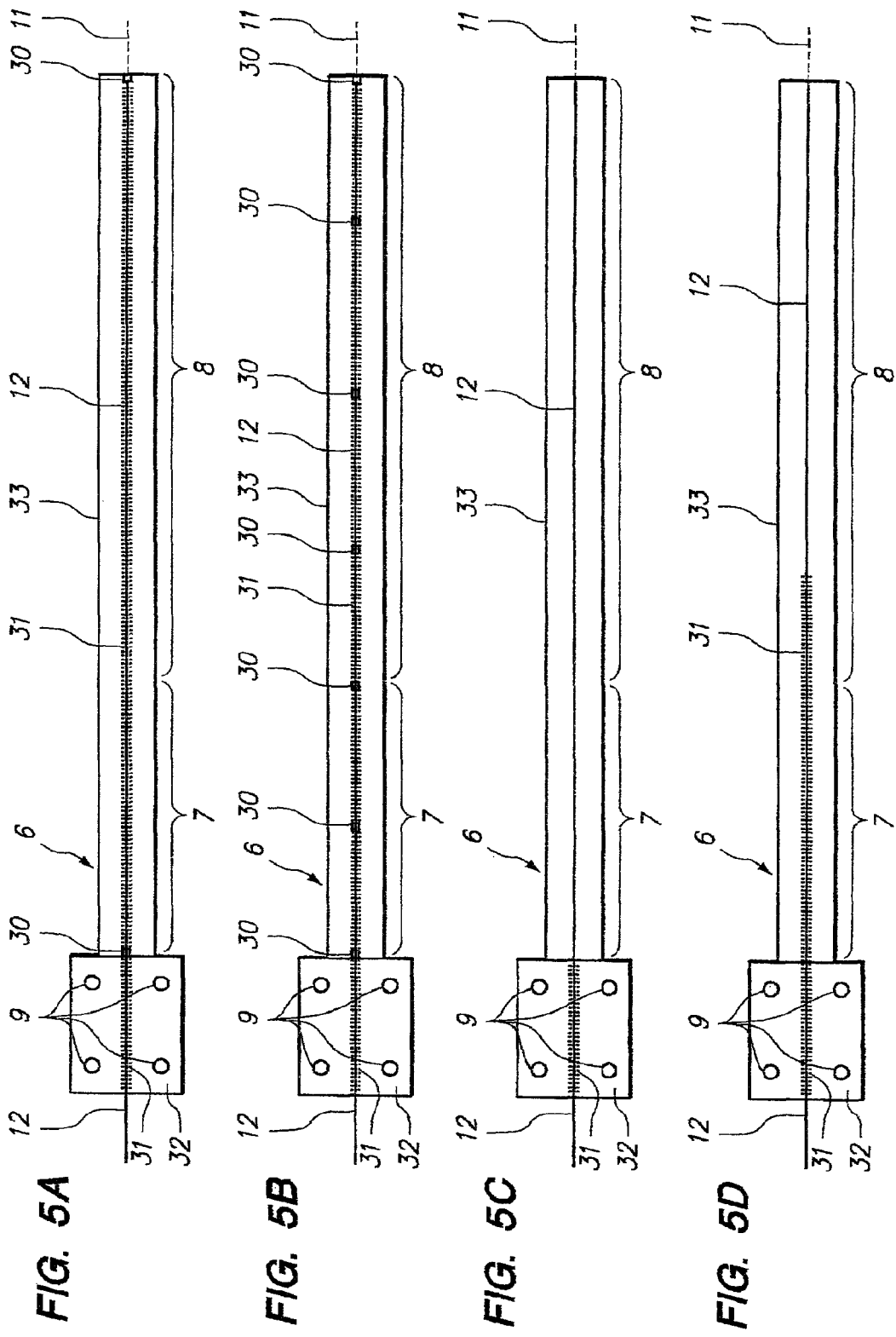

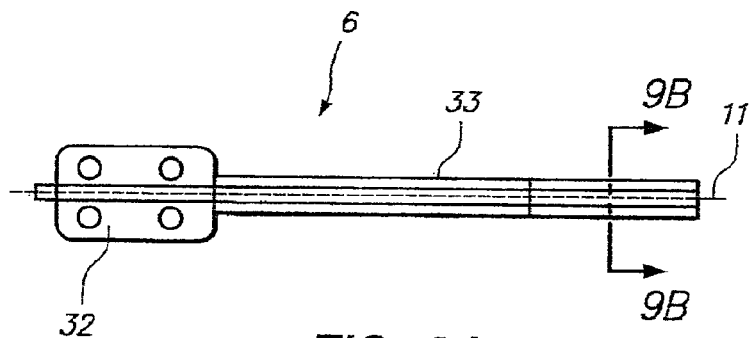 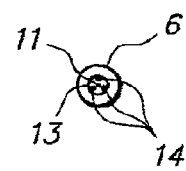
FIG. 9A  FIG. 9B
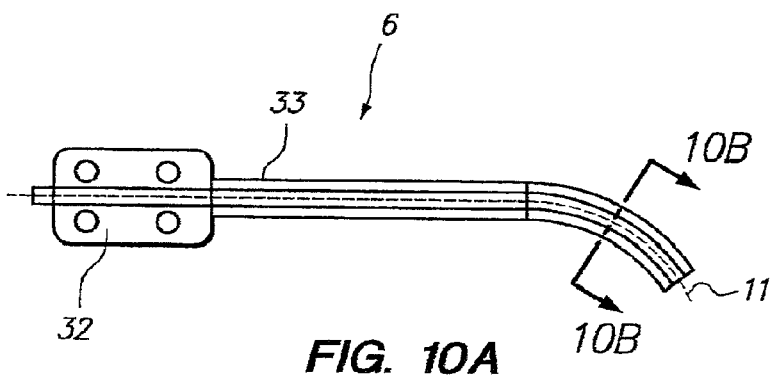 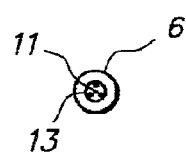
FIG. 10A  FIG. 10B
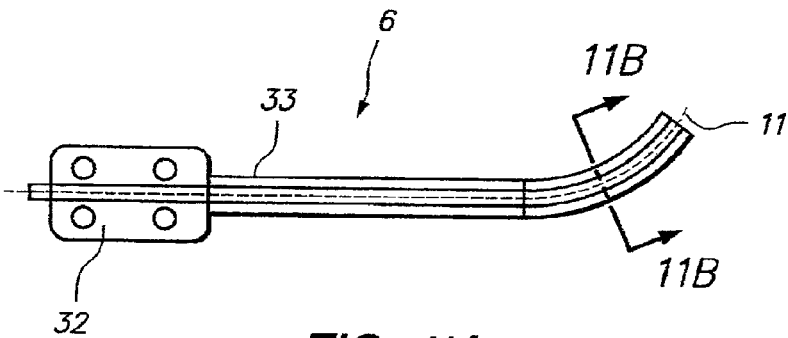 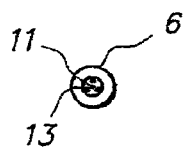
FIG. 11A  FIG. 11B

FIG. 17G-1

A: The first step comprises placing a Nylon 12 Jacket approx. 2-3 mils thick over the entire length (proximal and distal) of the mandrel

B: Polymide tubes lined with PTFE are stuffed with rectangular mandrels 4mil X 12mil. Also, add mandrels for optical fiber. The small mandrels are placeholders for the tension elements, to be installed later with the pertinent ring element to which they are soldered. Then the polymide-PTFE-lined mandrels are heat shrinked to the nylon jacket (from "A" above).

C: Subsequently the entire length is braided with 1X3 mil rectangular wire in a diamond pattern; 75 ppi (picks per inch) from the proximal end to the proximal ring, then loosened to 60 ppi from proximal ring to distal end.

C+: The portion distal of the proximal ring is then covered with a later-to-be-removed layer of heat shrink tubing.

D: At this point, the entire length of the sheath is braided again with the same wire at a 40 ppi rate.

E: Next, a 3 mil thick nylon-12 jacket, approximately 80d hardness, is applied over the portion of the sheath proximal to the proximal ring

| FIG. 17G-1 | FIG. 17G-2 |

OPTICAL FIBER SHAPE SENSING SYSTEMS

RELATED APPLICATION DATA

The present application is a divisional of U.S. patent application Ser. No. 13/073,295, filed on Mar. 28, 2011, now U.S. Pat. No. 8,515,215 which is a continuation of U.S. patent application Ser. No. 12/106,254, filed on Apr. 18, 2008 and issued as U.S. Pat. No. 8,050,523, which claims benefit under 35 U.S.C. §119 to U.S. Provisional Patent Application Ser. Nos. 60/925,449, filed on Apr. 20, 2007 and U.S. Provisional Patent Application Ser. No. 60/925,472, filed on Apr. 20, 2007, the contents of each of which are incorporated herein by reference as though set forth in full.

The present application may also be related to subject matter disclosed in the following applications, the contents of which are also incorporated herein by reference as though set forth in full: U.S. patent application Ser. No. 11/073,363, filed on Mar. 4, 2005; U.S. patent application Ser. No. 11/481,433, filed on Jul. 3, 2006; U.S. patent application Ser. No. 11/690,116, filed on Mar. 22, 2007; and U.S. patent application Ser. No. 12/012,795, filed on Feb. 1, 2008.

BACKGROUND

Field

The present disclosure relates generally to optical fibers with Bragg gratings that are configured to provide real-time feedback of its own dynamic shape, and more particularly to methods, systems, and apparatus for sensing and determining the dynamic shape, positions, temperatures, and stress or strain along portions, sections, or the length of an elongate steerable instrument using optical fibers with Bragg gratings.

Current minimally invasive procedures for diagnosis and treatment of medical conditions use elongate instruments, such as catheters or more rigid arms or shafts, to approach and address various tissue structures within the body. For many reasons, it is highly valuable to be able to determine the 3-dimensional spatial positions and/or orientations of various portions of such elongate instruments relative to other structures, such as pertinent tissue structures, other instruments, particular reference points, the operating table, etc. Conventional technologies such as electromagnetic position sensors, available from providers such as the Biosense Webster division of Johnson & Johnson, Inc., may be utilized to measure 3-dimensional spatial positions. However, conventional technology has limited utility for elongate medical instrument applications due to hardware geometric constraints, electromagnetivity issues, etc.

Accordingly, there is a need for an alternative technology to facilitate the execution of minimally-invasive interventional or diagnostic procedures while monitoring 3-dimensional spatial positions and/or orientations of elongate instruments.

SUMMARY

In accordance with one aspect of the present disclosure, a method for measuring bending is provided. The method includes receiving a reflected signal from a strain sensor provided on an optical fiber; determining a spectral profile of the reflected signal; and determining bending of the optical fiber based on a comparison of the spectral profile of the reflected signal with a predetermined spectral profile.

In accordance with another aspect of the present disclosure, an instrument system that includes an optical fiber, a detector and a controller is provided. The optical fiber has a strain sensor provided thereon. The detector is operatively coupled to the optical fiber and is configured to receive a reflected signal from the strain sensor. The controller is operatively coupled to the detector and is configured to determine a spectral profile of the reflected signal received by the detector, and determine bending of the optical fiber based on a comparison of the spectral profile of the reflected signal with a predetermined spectral profile.

These and other aspects of the present disclosure, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. In one embodiment, the structural components illustrated can be considered are drawn to scale. It is to be expressly understood, however, that the drawings are for the purpose of illustration and description only and are not intended as a definition of the limits of the present disclosure. It shall also be appreciated that the features of one embodiment disclosed herein can be used in other embodiments disclosed herein. As used in the specification and in the claims, the singular form of "a", "an", and "the" include plural referents unless the context clearly dictates otherwise.

BRIEF DESCRIPTION OF THE DRAWINGS

The present disclosure will be readily understood by the following detailed description, taken in conjunction with accompanying drawings, illustrating by way of examples the principles of the present disclosure. The drawings illustrate the design and utility of preferred embodiments of the present disclosure, in which like elements are referred to by like reference symbols or numerals. The objects and elements in the drawings are not necessarily drawn to scale, proportion or precise positional relationship; instead emphasis is focused on illustrating the principles of the present disclosure.

FIGS. 4A-4D illustrate the implementations of an optical fiber with Bragg gratings to an elongate instrument such as a robotically-steerable catheter.

FIGS. 5A-5D illustrate the implementations of an optical fiber with Bragg gratings to an elongate instrument such as a robotically-steerable catheter.

FIGS. 9A-9B illustrate top and cross-sectional views of an elongate instrument such as a catheter having a multi-fiber structure with Bragg gratings.

FIGS. 10A-10B illustrate top and cross-sectional views of an elongate instrument such as a catheter having a multi-fiber structure with Bragg gratings.

FIGS. 11A-11B illustrate top and cross-sectional views of an elongate instrument such as a catheter having a multi-fiber structure with Bragg gratings.

DETAILED DESCRIPTION OF THE ILLUSTRATED EMBODIMENTS

Reference will now be made in detail to the preferred embodiments of the present disclosure, examples of which are illustrated in the accompanying drawings. While the present disclosure will be described in conjunction with the preferred embodiments, it will be understood that they are not intended to limit the present disclosure to these embodiments. On the contrary, the present disclosure is intended to cover alternatives, modifications and equivalents that may be included within the spirit and scope of the present disclosure. Furthermore, in the following detailed description of the present disclosure, numerous specific details are set forth in to order to provide a thorough understanding of the present disclosure. However, it will be readily apparent to one skilled in the art that the present disclosure may be practiced without these specific details. In other instances, well-known methods, procedures, and components have not been described in detail so as not to unnecessarily obscure aspects of the present disclosure.

Figure 1:
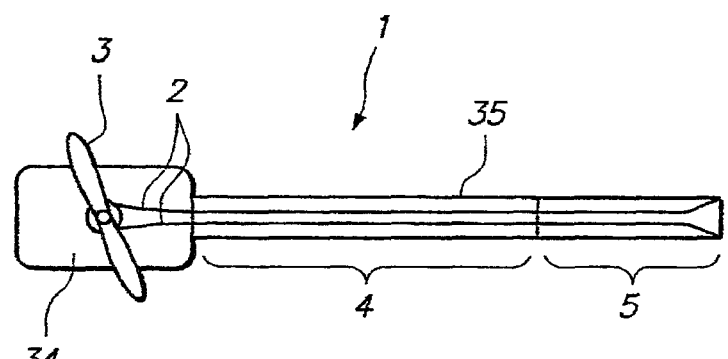
FIG. 1 illustrates an example of an elongate instrument such as a conventional manually operated catheter.

All of the following technologies may be utilized with manually or robotically steerable instruments, such as those described in the aforementioned U.S. patent application Ser. No. 11/073,363 and U.S. patent application Ser. No. 11/481, 433. FIG. 1 illustrates an example of elongate instrument that may be used for minimal invasive interventional or diagnostic operations. In this example the elongate instrument is a manually-steerable catheter suitable for performing interventional or diagnostic operations. Catheter (1) includes pullwires (2) that may be selectively tensioned by manipulating a handle (3) on the proximal portion of the catheter structure to make a more flexible distal portion (5) of the catheter (1) bend or steer in a controlled manner. The handle (3) may be coupled, rotatably or slidably, for example, to a proximal catheter structure (34) which may be configured to be held by an operator, and may be coupled to the elongate portion (35) of the catheter (1). A more proximal, and typically less steerable, portion (4) of the catheter (1) may be configured to be compliant to loads exerted from surrounding tissues (for example, to facilitate passing the catheter, including portions of the proximal portion, through various tortuous pathways such as those formed by blood vessels in a body), yet less steerable as compared to the distal portion (5) of the catheter (1). As will be explained below, embodiments of the present disclosure enable the determination of 3-dimensional spatial positions and/or orientation of portions of such elongate instruments.

Figure 2:
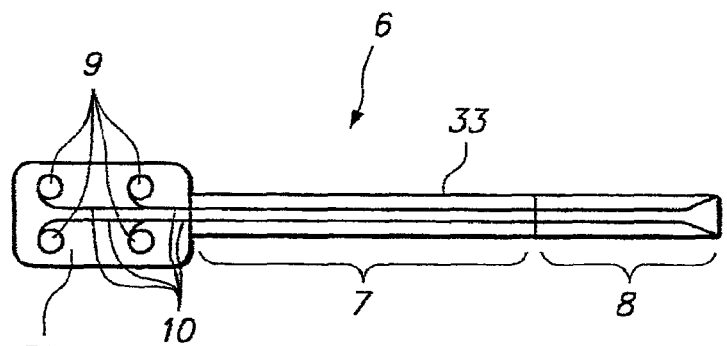
FIG. 2 illustrates another example of an elongate instrument such as a robotically-driven steerable catheter.

FIG. 2 illustrates another example of an elongate instrument that may be used for minimally invasive interventional or diagnostic procedures. In this example the elongate instrument is a robotically-driven steerable catheter, similar to those described in detail in U.S. patent application Ser. No. 11/176,598, incorporated by reference herein in its entirety. This catheter (6) has some similarities with the manually-steerable catheter (1) of FIG. 1 in that it has pullwires (10) associated distally with a more flexible section (8) that is configured to be steered or bent when the pullwires (10) are tensioned in various manners, as compared with a typically less steerable proximal portion (7) configured to be stiffer and more resistant to bending or steering. The depicted embodiment of the robotically-driven steerable catheter (6) comprises proximal axles or spindles (9) configured to primarily interface not with an operator, but with an electromechanical instrument driver that is configured to coordinate and drive, by means of a control unit such as a computer and associated hardware (not shown), each of the spindles (9) to produce precise steering or bending movements of the catheter (6). The spindles (9) may be rotatably coupled to a proximal catheter structure (32) which may be configured to be mounted to an electromechanical instrument driver apparatus, such as that described in the aforementioned U.S. patent application Ser. No. 11/176,598, and may be coupled to the elongate portion (33) of the catheter (6).

Each of the embodiments depicted in FIGS. 1 and 2 may have a working lumen (not shown) located, for example, down the central or neutral axis of the catheter body, or may be without such a working lumen. A lumen may be tubular space or channel within any organ, structure of the body, or instrument. For example, a lumen may be a tube in a catheter, the space or channel in a blood vessel, intestine, etc., or a cavity or opening in an organ. If a working lumen is formed by the catheter structure, it may extend directly out the distal end of the catheter, or may be capped or blocked at the distal tip of the catheter. It is highly useful in many minimally invasive interventional or diagnostic procedures to have precise information regarding the position of the distal tip of such catheters or other elongate instruments, such as those available from suppliers such as the Ethicon Endosurgery division of Johnson & Johnson, Inc., Intuitive Surgical, Inc., or Hansen Medical, Inc. The examples and illustrations that follow are made in reference to a robotically-steerable catheter such as that depicted in FIG. 2, but as would be apparent to one skilled in the art, the same principles may be applied to other elongate instruments, such as the manually-steerable catheter depicted in FIG. 1, or other elongate instruments, flexible or not, from suppliers such as the Ethicon Endosurgery division of Johnson & Johnson, Inc., Intuitive Surgical, Inc., or Hansen Medical, Inc.

Figure 3A:
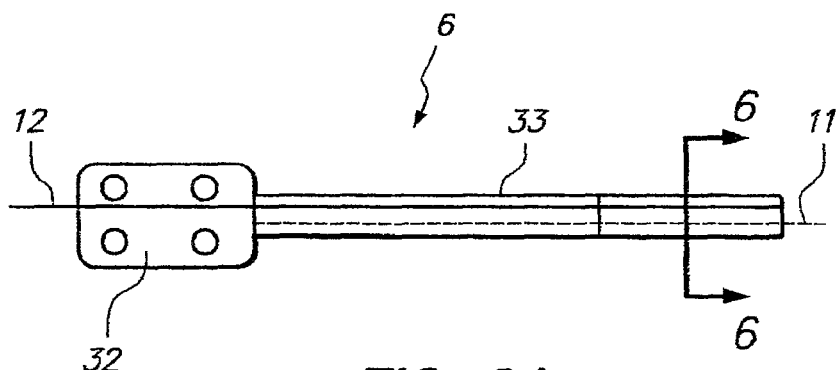
FIGS. 3A-3C illustrate the implementations of an optical fiber with Bragg gratings to an elongate instrument such as a robotically-steerable catheter.
Figure 3B:
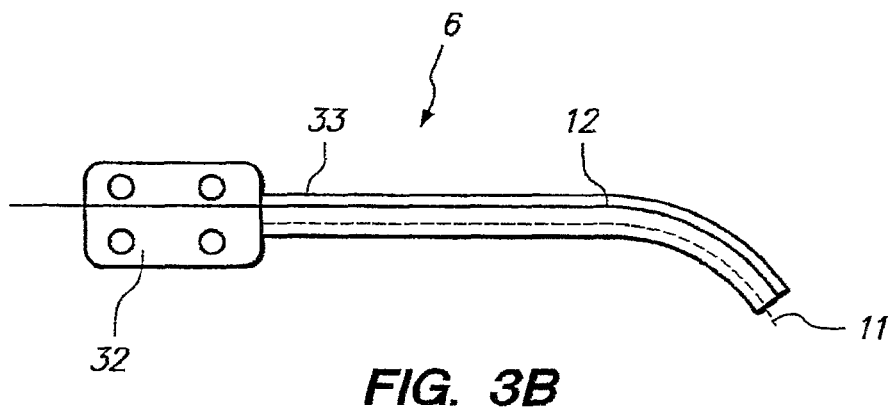
Figure 3C:
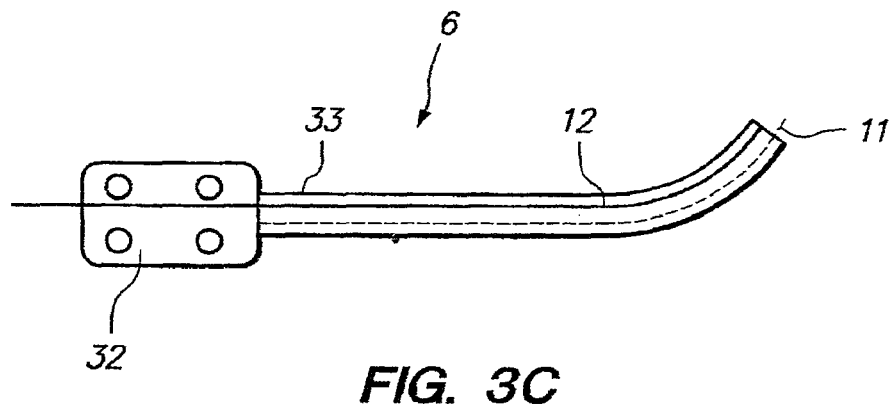

Referring to FIGS. 3A-3C, a robotically-steerable catheter (6) is depicted having an optical fiber (12) positioned along one aspect of the wall of the catheter (6). The fiber is not positioned coaxially with the central or neutral axis (11) of the catheter in the bending scenarios depicted in FIGS. 3B and 3C. Indeed, with the fiber (12) attached to, or longitudinally constrained by, at least two different points along the length of the catheter (6) body (33) and unloaded from a tensile perspective relative to the catheter body in a neutral position of the catheter body (33) such as that depicted in FIG. 3A, the longitudinally constrained portion of the fiber (12) would be placed in tension in the scenario depicted in FIG. 3B, while the longitudinally constrained portion of the fiber (12) would be placed in compression in the scenario depicted in FIG. 3C. Such relationships are elementary to solid mechanics, but may be applied as described herein with the use of Bragg fiber gratings or other fiber optic strain sensors for determining and monitoring 3-dimensional spatial shapes and positions of elongate instruments.

Conventional "fiber Bragg grating" ("FBG") sensors or components thereof, available from suppliers such as Luna Innovations, Inc., of Blacksburg, Va., Micron Optics, Inc., of Atlanta, Ga., Avensys, Inc., and LxSix Photonics, Inc., of Quebec, Canada, and Ibsen Photonics A/S, of Denmark, have been used in various applications to measure strain in structures such as highway bridges and aircraft wings.

FIGS. 4A-4D illustrate several different embodiments of optical fibers with Bragg grating implemented on an elongate instrument such as a catheter in accordance with embodiments of the present disclosure. Referring to FIG. 4A, a robotic catheter (6) is depicted having a fiber (12) deployed through a lumen (31) which extends from the distal tip of the distal portion (8) of the catheter body (33) to the proximal end of the proximal catheter structure (32). In one embodiment a broadband reference reflector (not shown) is positioned near the proximal end of the fiber in an operable relationship with the fiber Bragg grating wherein an optical path length is established for each reflector/grating relationship comprising the subject fiber Bragg sensor configuration; additionally, such configuration also comprises a reflectometer (not shown) to conduct spectral analysis of detected reflected portions of light waves.

Constraints (30) may be provided to substantially constrain axial or longitudinal motion of the fiber (12) at the location of each constraint (30). Alternatively, the constraints (30) may only substantially constrain the position of the fiber (12) relative to the lumen (31) in the location of the constraints (30). For example, in one variation of the embodiment depicted in FIG. 4A, the most distal constraint (30) may be configured to substantially constrain longitudinal or axial movement of the fiber (12) relative to the catheter body (33) at the location of such constraint (30), while the more proximal constraint (30) may merely act as a guide to lift the fiber (12) away from the walls of the lumen (31) at the location of such proximal constraint (30). In another variation of the embodiment depicted in FIG. 4A, both the more proximal and more distal constraints (30) may be configured to substantially constrain longitudinal or axial movement of the fiber (12) at the locations of such constraints, and so on. As shown in the embodiment depicted in FIG. 4A, the lumen (31) in the region of the proximal catheter structure (32) is without constraints to allow for free longitudinal or axial motion of the fiber relative to the proximal catheter structure (32). Constraints configured to substantially constrain relative motion between the constraints (30) and fiber (12) at a given location may comprise small adhesive or polymeric welds, interference fits formed with small geometric members comprising materials such as polymers or metals, locations wherein braiding structures are configured with extra tightness to prohibit motion of the fiber (12), or the like. Constraints (30) configured to guide the fiber (12) but to also substantially allow relative longitudinal or axial motion of the fiber (12) relative to such constraints (30) may comprise small blocks, spheres, hemispheres, etc. defining small holes, generally through the geometric middle of such structures, for passage of the subject fiber (12).

The embodiment of FIG. 4B is similar to that of FIG. 4A, with the exception that there are two additional constraints (30) provided to substantially guide and/or constrain longitudinal or axial movement of the fiber (12) relative to such constraints (30) at these locations. In one variation, each of the constraints is a total relative motion constraint, to isolate the longitudinal strain within each of three "cells" provided by isolating the length of the fiber (12) along the catheter body (33) into three segments utilizing the constraints (30). In another variation of the embodiment depicted in FIG. 4B, the proximal and distal constraints (30) may be total relative motion constraints, while the two intermediary constraints (30) may be guide constraints configured to allow longitudinal or axial relative motion between the fiber (12) and such constraints at these intermediary locations, but to keep the fiber aligned near the center of the lumen (31) at these locations.

Referring to FIG. 4C, an embodiment similar to those of FIGS. 4A and 4B is depicted, with the exception that entire length of the fiber that runs through the catheter body (33) is constrained by virtue of being substantially encapsulated by the materials which comprise the catheter body (33). In other words, while the embodiment of FIG. 4C does have a lumen (31) to allow free motion of the fiber (12) longitudinally or axially relative to the proximal catheter structure (32), there is no such lumen defined to allow such motion along the catheter body (33), with the exception of the space naturally occupied by the fiber as it extends longitudinally through the catheter body (33) materials which encapsulate it.

FIG. 4D depicts a configuration similar to that of FIG. 4C with the exception that the lumen (31) extends not only through the proximal catheter structure (32), but also through the proximal portion (7) of the catheter body (33); the distal portion of the fiber (12) which runs through the distal portion of the catheter body (33) is substantially encapsulated and constrained by the materials which comprise the catheter body (33).

FIGS. 5A-5D illustrate other embodiments of optical fibers with Bragg grating implemented on an elongate instrument such as a catheter similar to those depicted in FIGS. 4A-D. However, as shown in FIGS. 5A-5D, the fiber (12) is positioned substantially along the central or neutral axis (11) of the catheter body (33), and in the embodiment of FIG. 5B, there are seven constraints (30) as opposed to the three of the embodiment in FIG. 4B.

Figure 6:
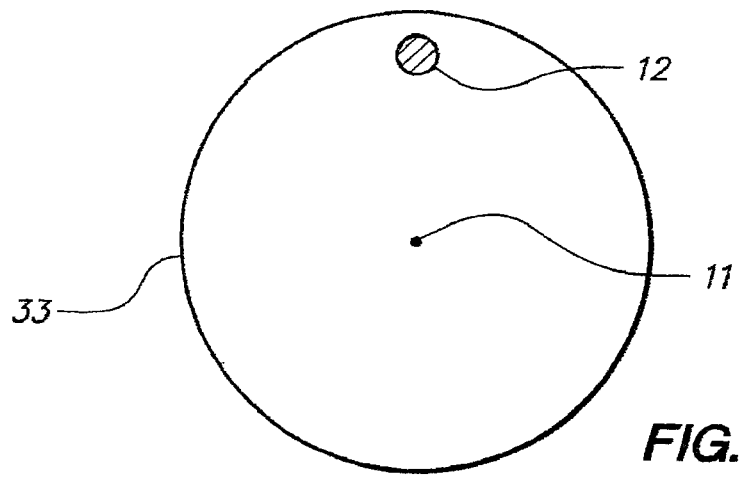
FIG. 6 illustrates a cross-sectional view of an elongate instrument such as a catheter including an optical fiber with Bragg gratings.
Figure 7:
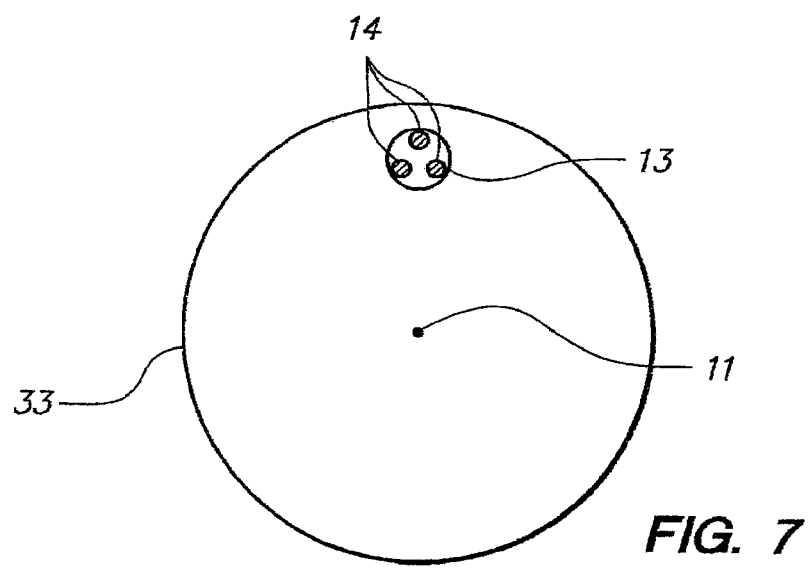
FIG. 7 illustrates a cross-sectional view of an elongate instrument such as a catheter including an optical fiber with Bragg gratings, wherein the optical fiber is a multi-fiber bundle.
Figure 8:
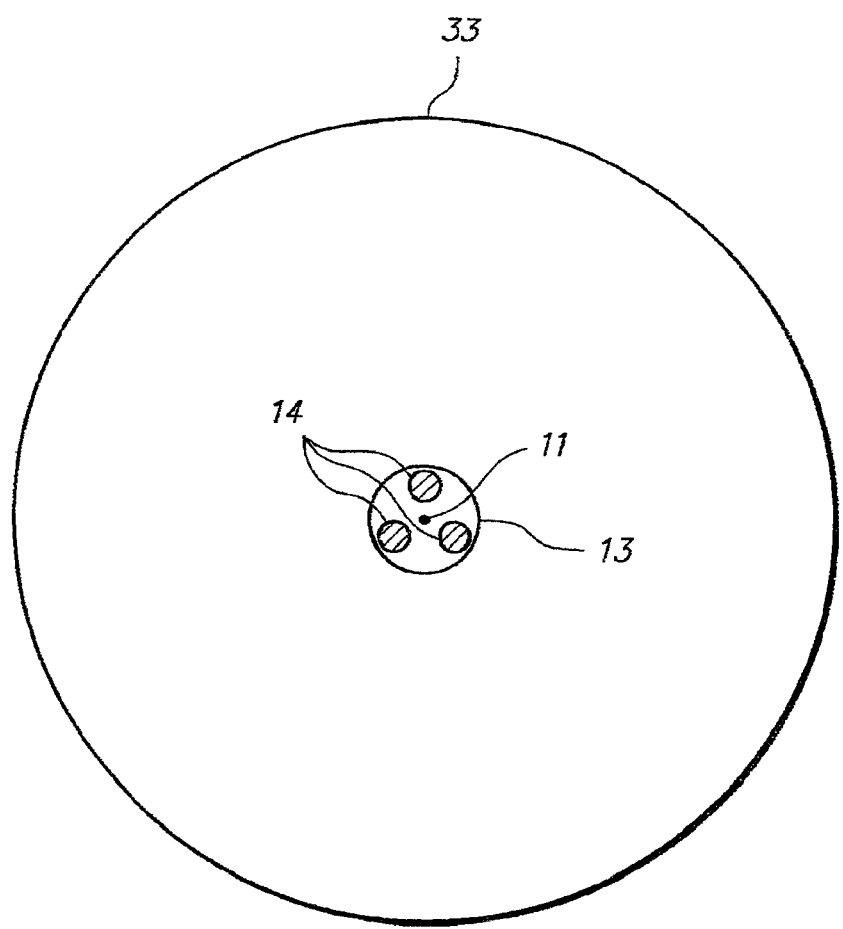
FIG. 8 illustrates a cross-sectional view of an elongate instrument such as a catheter including an optical fiber with Bragg gratings, wherein the optical fiber is a multi-fiber bundle.

FIG. 6 illustrates a cross sectional view of a section of an elongate instrument such as a catheter body (33) similar to the configuration shown in FIG. 4C. As FIG. 6 illustrates, fiber (12) is not placed concentrically with the central or neutral axis (11) of the catheter body (33). FIG. 7 illustrates a similar embodiment, wherein a multi-fiber bundle (13), such as those available from Luna Technologies, Inc., is positioned within the wall of the catheter rather than a single fiber as depicted in FIG. 6. The fiber bundle (13) comprises of multiple individual (e.g., smaller) fibers or fiber cores (14), for example three fibers or fiber cores. When a structure such as that depicted in FIG. 7 is placed in bending as illustrated in FIG. 3B or 3C, the most radially outward (from the central or neutral axis (11)) fiber or fibers (14) will be exposed to greater compressive or tensile stress than the more radially inward fiber or fibers. Alternatively, in an embodiment such as that depicted in FIG. 8, which shows a cross section of an elongate instrument such as a catheter body (33) similar to the configuration illustrated in FIG. 5C. A multi-fiber bundle (13) is positioned coaxially with the central or neutral axis (11) of the catheter (6). Each of the three individual fibers (14), as shown in either FIG. 7 or FIG. 8, within the bundle (13) will be exposed to different tensile or compressive stresses in accordance with the bending or steering deflection of the subject catheter. As will be discussed in more detail below, the 3-dimensional shape of the fiber structure (13) may be determined from the different tensile or compressive stress exposed to each of the multiple fibers (14) in the bundle (13) due to bending or steering deflection of the catheter body (33).

FIGS. 9A and 9B illustrate top and cross sectional views of an elongate instrument such as a catheter. As shown in FIG. 9A, catheter (33) is in a neutral position. As such, all three individual fibers (14) comprising the depicted bundle (13) may be in an unloaded configuration. FIGS. 10A and 10B illustrate top and cross sectional views of an elongate instrument such as a catheter. As illustrated in FIG. 10A, catheter (33) is deflected downward. Because of the downward bending or deflection, the lowermost two fibers in the fiber bundle (13) may be exposed to compressive stress, while the uppermost fiber may be exposed to tensile stress. The opposite would happen with an upward bending or deflection scenario such as that depicted in FIGS. 11A and 11B. Since the fiber bundles (13) shown in FIGS. 9-11 are all multiple fiber bundles, the different compressive or tensile stresses will provide the information necessary to determine the 3-dimensional shape of the fiber bundle structures (13) respectively associated with the catheter bodies (33) illustrated in FIGS. 9-11. In addition to the up and down bending of the catheter, the catheter (33) may be bent left and right. The fiber bundle (13) will measure the 3-dimensional shape of the catheter regardless of the direction of bend, e.g., up, down, left, right, any arbitrary direction or shape including a bend that would cause the catheter to point backwards (i.e., catheter doubleback on itself), or bends that would create loops, etc.

Indeed, various fiber position configurations may be employed, depending upon the particular application, such as those depicted in FIGS. 12A-12H. For simplicity, each of the cross sectional embodiments of FIGS. 12A-12H is depicted without reference to lumens adjacent the fibers, or constraints (i.e., each of the embodiments of FIGS. 12A-12H are depicted in reference to catheter body configurations analogous to those depicted, for example, in FIGS. 4C and 5C, wherein the fibers are substantially encapsulated by the materials comprising the catheter body (33). Additional variations comprising combinations and permutations of constraints and constraining structures, such as those depicted in FIGS. 4A-5D, are within the scope of this present disclosure. FIG.

Figure 12A:
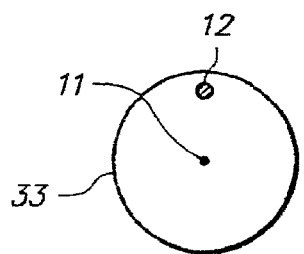
FIGS. 12A-12H illustrate cross-sectional views of elongate instruments with various fiber positions and configurations.
Figure 12B:
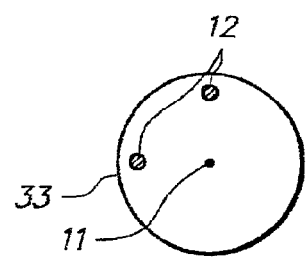
Figure 12C:
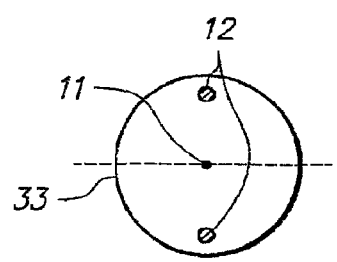
Figure 12D:
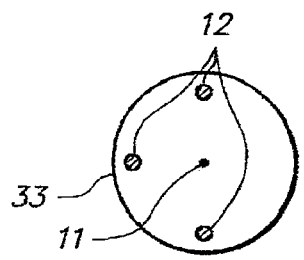
Figure 12E:
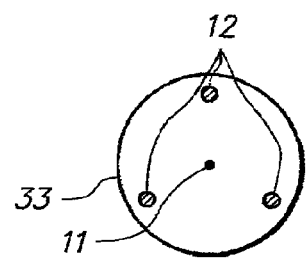
Figure 12F:
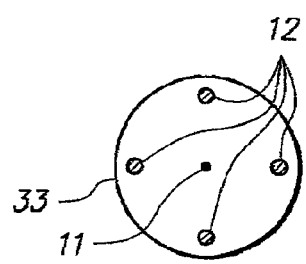
Figure 12G:
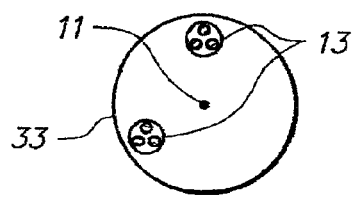
Figure 12H:
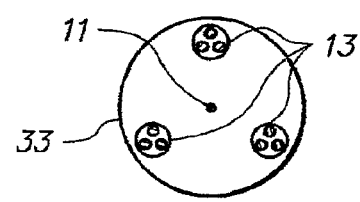

12A depicts an embodiment having one fiber (12). FIG. 12B depicts a variation having two fibers (12) in a configuration capable of detecting tensions sufficient to calculate three-dimensional spatial deflection of the catheter portion. FIG. 12C depicts a two-fiber variation that may be redundant for detecting bending about a bending axis such as that depicted in FIG. 3B or FIG. 3C. FIGS. 12D and 12E depict three-fiber configurations configured for detecting three-dimensional spatial deflection of the subject catheter portion. FIG. 12F depicts a variation having four fibers configured to accurately detect three-dimensional spatial deflection of the subject catheter portion. FIGS. 12G and 12H depict embodiments similar to 12B and 12E, respectively, with the exception that multiple bundles of fibers are integrated, as opposed to having a single fiber in each location. Each of the embodiments depicted in FIGS. 12A-12H, may be utilized to detect deflection of the catheter body (33) due to compression, tension, twist, torsion, and/or any combination thereof for the determination of 3-dimensional shape of the catheter body (33). Such applications are further discussed in reference to FIGS. 13, 14A, and 14B.

Figure 13:
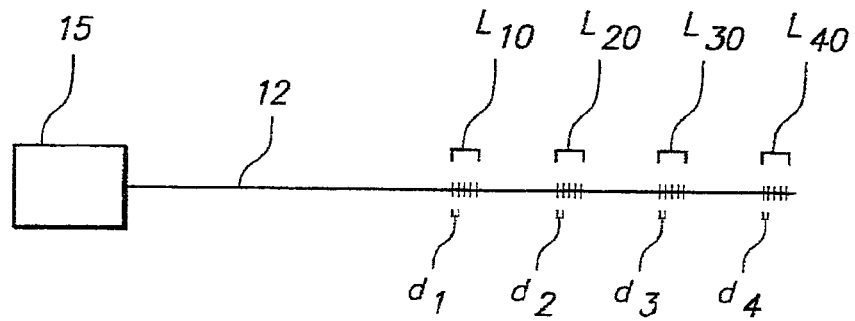
FIG. 13 illustrates an optical fiber sensing system with Bragg gratings.

Referring to FIG. 13, a single optical fiber (12) is depicted having four sets of Bragg diffraction gratings, each of which may be utilized as a local deflection sensor. Fiber (12) may be interfaced with portions of an elongate instrument such as a catheter (not shown) in various manners as those depicted, for example, in FIGS. 12A-12H. A single detector (15) may be used to detect and analyze signals from more than one fiber. With a multi-fiber configuration, such as those depicted in FIGS. 12B-12H, a proximal manifold structure may be utilized to interface the various fibers with one or more detectors. Interfacing techniques for transmitting signals between detectors and fibers are well known in the art of optical data transmission. The detector is operatively coupled with a controller configured to determine a geometric configuration of the optical fiber and, therefore, at least a portion of the associated elongate instrument (e.g., catheter) body based on a spectral analysis of the detected reflected light signals. Further details are provided in Published US Patent Application 2006/0013523, the contents of which are fully incorporated herein by reference.

In the single fiber embodiment as depicted in FIG. 13, each of the gratings has a different spacing ($d_1$, $d_2$, $d_3$, $d_4$), and a corresponding reflection spectra center at a wavelength corresponding to this spacing and thus a proximal wavelength detection system consisting in part of a light source for the depicted single fiber and detector may detect variations in wavelength for each of the "sensor" lengths ($L_{10}$, $L_{20}$, $L_{30}$, $L_{40}$). Commercial wavelength detection systems of this sort are sold by Micron Optics, Inc., Luna Innovations, Ibsen Photonics, and other companies worldwide. Thus, given determined length changes at each of the "sensor" lengths ($L_{10}$, $L_{20}$, $L_{30}$, $L_{40}$), the longitudinal positions of the "sensor" lengths ($L_{10}$, $L_{20}$, $L_{30}$, $L_{40}$), and a known configuration such as those depicted in cross section in FIGS. 12A-12H, the deflection and/or position of the associated elongate instrument in space may be determined. One of the challenges with a configuration such as that depicted in FIG. 13 is that a fairly spectrally or tunable light source and or a broad band tunable detector is commonly utilized proximally to capture length differentiation data from each of the sensor lengths, potentially compromising the number of sensor lengths that may be monitored without interference between the reflective spectra associated by the Bragg fiber gratings in the array. Regardless, several fiber (12) and detector (15) configurations such as that depicted in FIG. 13 may comprise embodiments such as those depicted in FIGS. 12A-12H to facilitate determination of three-dimensional shape and position of an elongate medical instrument.

Figure 14A:
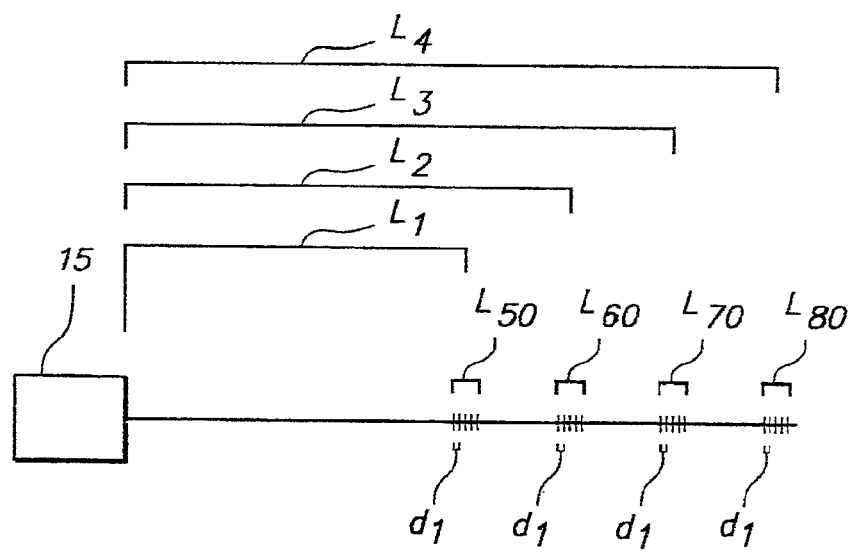
FIGS. 14A-14B illustrate an optical fiber sensing system with Bragg gratings.
Figure 14B:
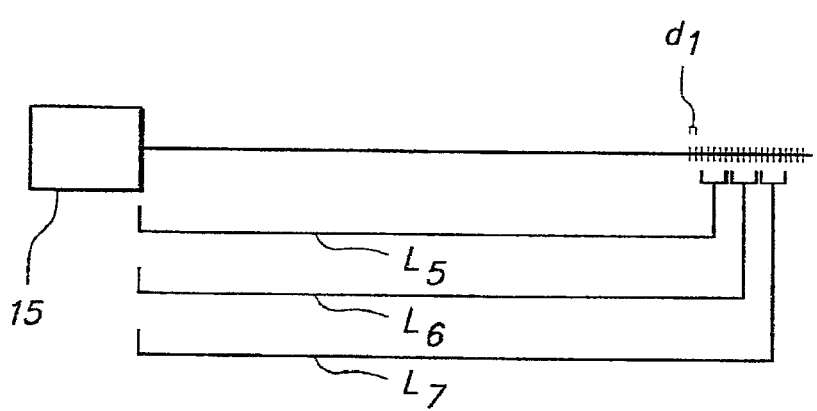

In another embodiment of a single sensing fiber, depicted in FIG. 14A, various sensor lengths ($L_{50}$, $L_{60}$, $L_{70}$, $L_{80}$) may be configured to each have the same grating spacing, and a more narrow band source may be utilized with some sophisticated analysis, as described, for example, in "Sensing Shape—Fiber-Bragg-grating sensor arrays monitor shape at high resolution," SPIE's OE Magazine, September, 2005, pages 18-21, incorporated by reference herein in its entirety, to monitor elongation at each of the sensor lengths given the fact that such sensor lengths are positioned at different positions longitudinally ($L_1$, $L_2$, $L_3$, $L_4$) away from the proximal detector (15). This approach is generally known as optical frequency domain reflectometry (OFDR) method. In another (related) embodiment, depicted in FIG. 14B, a portion of a given fiber, such as the distal portion, may have constant gratings created to facilitate high-resolution detection of distal lengthening or shortening of the fiber. Such a constant grating configuration would also be possible with the configurations described in the aforementioned scientific journal article. It should be noted that FIGS. 13, 14A and 14B show a single fiber for the purpose of simplicity. The fibers could be single core or multi-core. For example, multi-core fibers are shown in 12G and 12H as element (13). In particular, multi-core fibers are applicable to embodiments illustrated in FIGS. 9, 10, and 11 for measuring bend as described in the above paragraphs. In general, the embodiments described in the entirety of this document are applicable for single core or multi-core fibers.

As will be apparent to those skilled in the art, the fibers in the embodiments depicted herein will provide accurate measurements of localized length and shape changes in portions of the associated catheter or elongate instrument only if such fiber portions are indeed coupled in some manner to the nearby portions of the catheter or elongate instrument. In one embodiment, it is desirable to have the fiber or fibers intimately coupled with or constrained by the surrounding instrument body along the entire length of the instrument. In another embodiment, a proximal portion of a fiber may be coupled to a less bendable section of the catheter but configured to float freely floating along the catheter body, and a distal portion of a fiber may be intimately or tightly coupled to a distal portion of the catheter to facilitate high-precision monitoring of the bending or movement of the distal, and perhaps, more flexible portion of the catheter.

Figure 15:
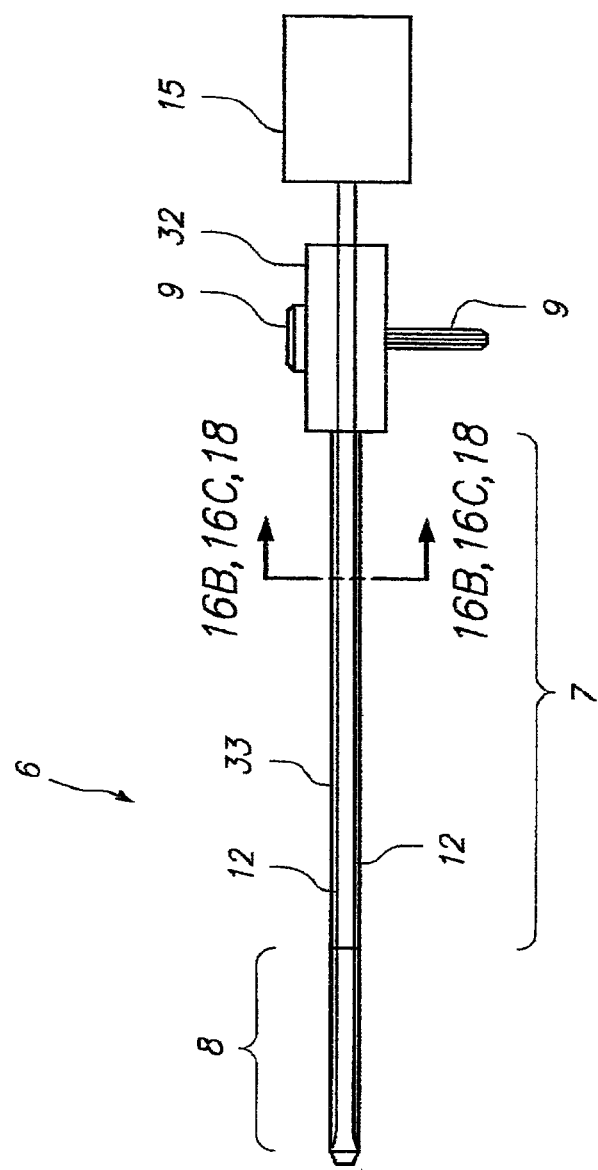
FIGS. 15 and 16A-16C illustrate integration of an optical fiber sensing system to a robotically-controlled catheter.
Figure 16A:
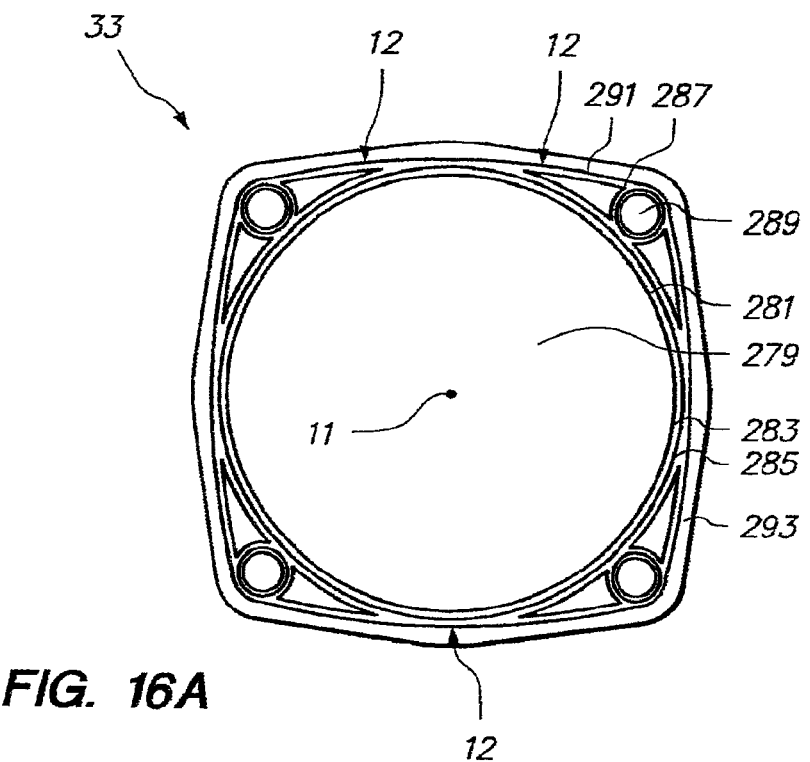
Figure 16B:
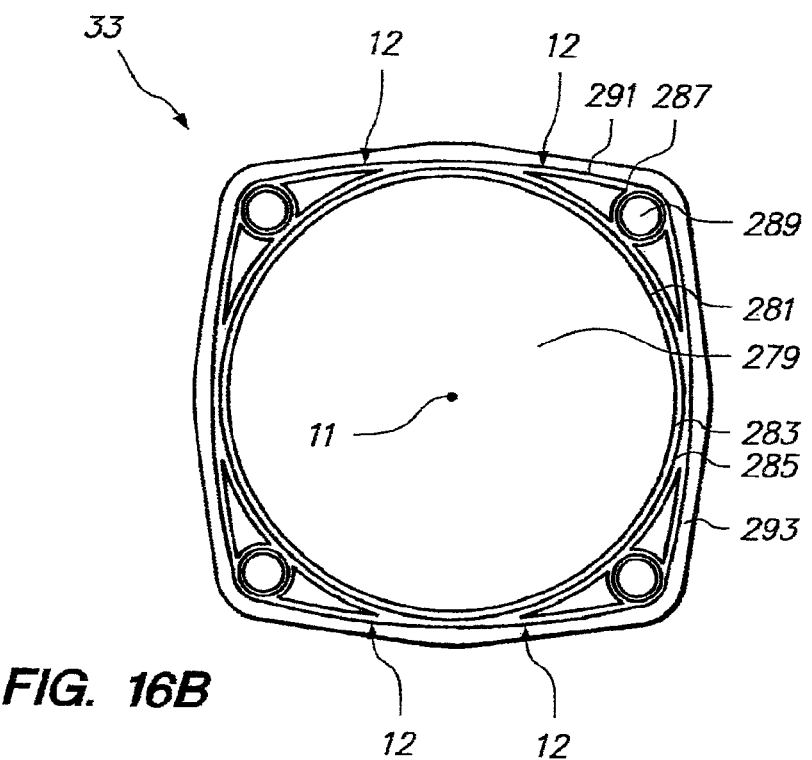
Figure 16C:
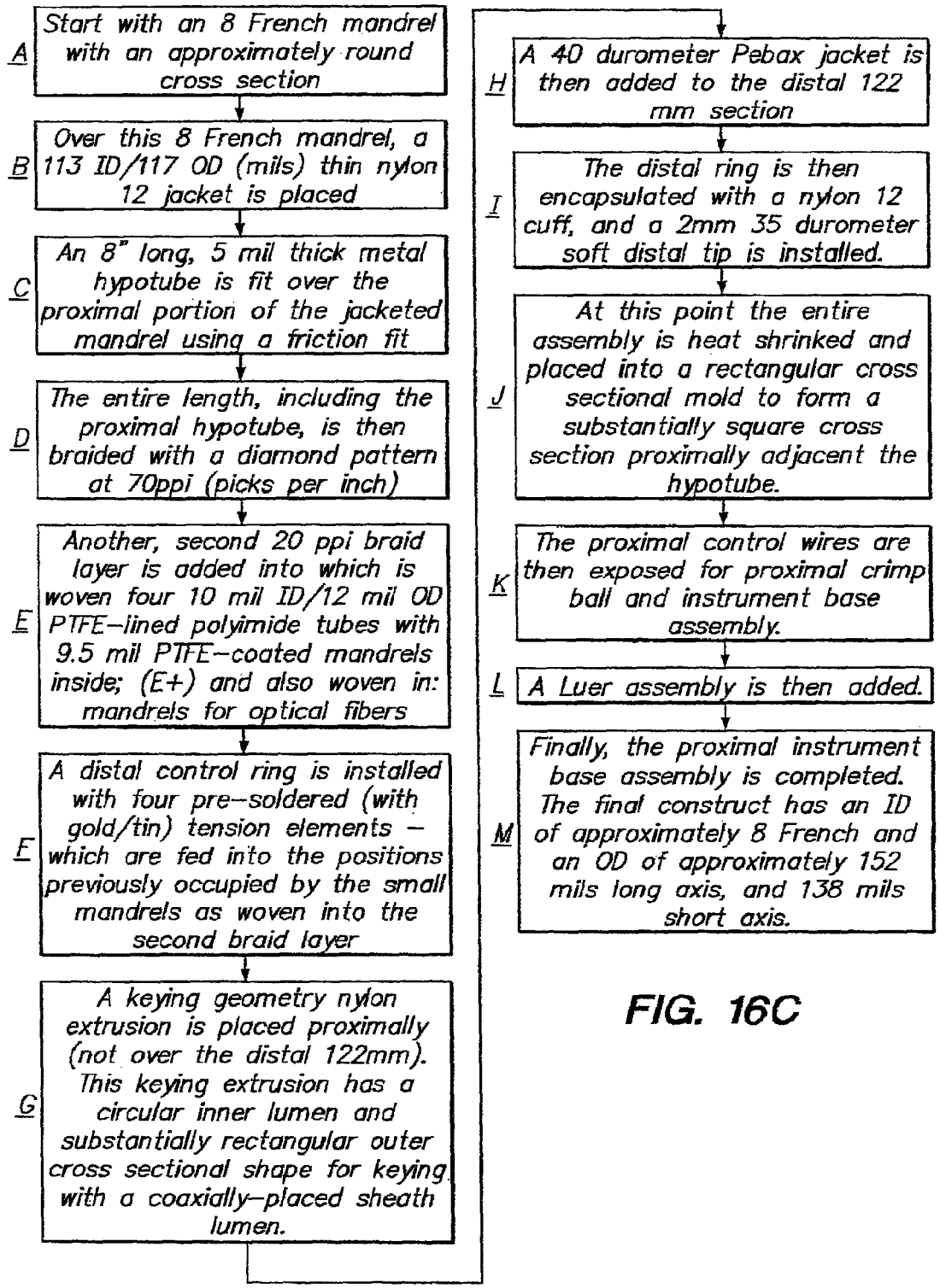

FIGS. 15, 16A, 16B, and 16C illustrate integration of an optical fiber sensing system to a robotically-controlled catheter. U.S. patent application Ser. No. 11/176,598, from which these drawings (along with FIGS. 17 and 18) have been taken and modified, is incorporated herein by reference in its entirety. FIGS. 15 and 16A show an embodiment with three optical fibers (12) and a detector (15) for detecting catheter bending and distal tip position. FIG. 16B depicts an embodiment having four optical fibers (12) for detecting catheter position. FIG. 16C depicts an integration to build such embodiments. As shown in FIG. 16C, in Step "E+", mandrels for optical fibers are woven into a braid layer, subsequent to which (Step "F") optical fibers with Bragg gratings are positioned in the cross sectional space previously occupied by such mandrels (after such mandrels are removed). The geometry of the mandrels relative to the fibers selected to occupy the positions previously occupied by the mandrels after the mandrels are removed preferably is selected based upon the level of constrain desired between the fibers (12) and surrounding catheter body (33) materials. For example, if a highly-constrained relationship, comprising substantial encapsulation, is desired, the mandrels will closely approximate the size of the fibers. If a more loosely-constrained geometric relationship is desired, the mandrels may be sized up to allow for relative motion between the fibers (12) and the catheter body (33) at selected locations, or a tubular member, such as a polyimide or PTFE sleeve, may be inserted subsequent to removal of the mandrel, to provide a "tunnel" with clearance for relative motion of the fiber, and/or simply a layer of protection between the fiber and the materials surrounding it which comprise the catheter or instrument body (33). Similar principles may be applied in embodiments such as those described in reference to FIGS. 17A-17G.

Figure 17A:
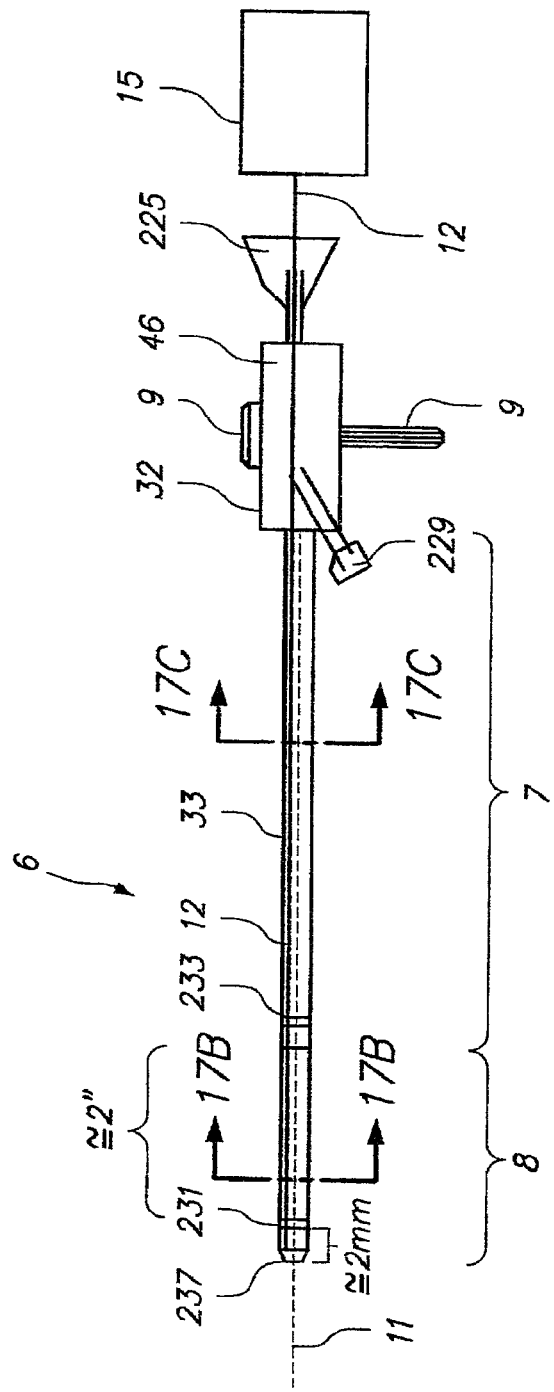
FIGS. 17A-17G illustrate the integration of sheath instruments.
Figure 17B:
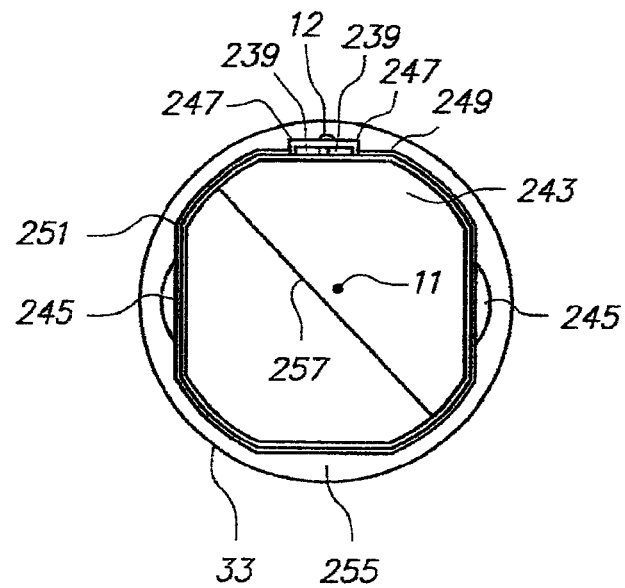
Figure 17C:
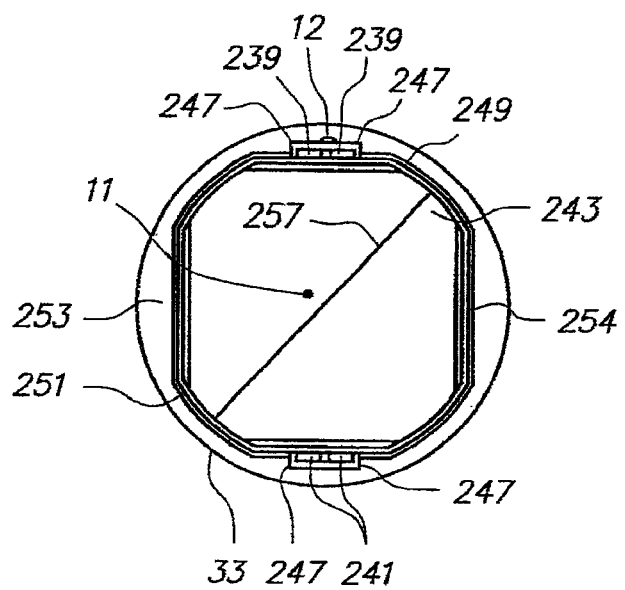
Figure 17D:
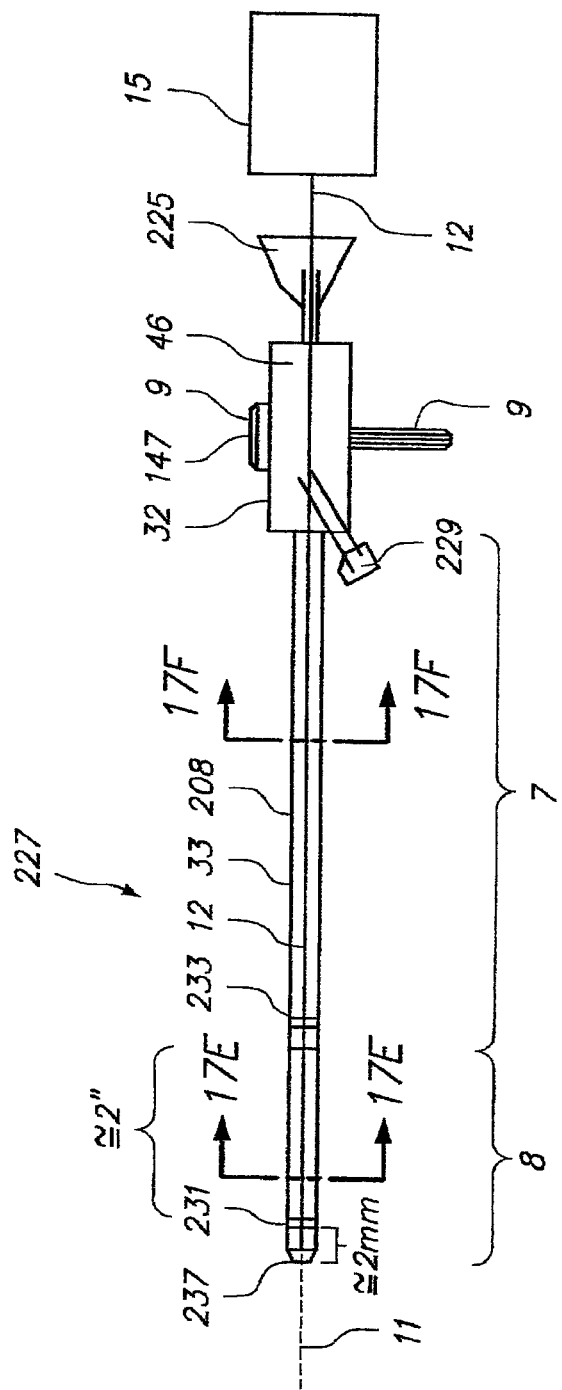
Figure 17E:
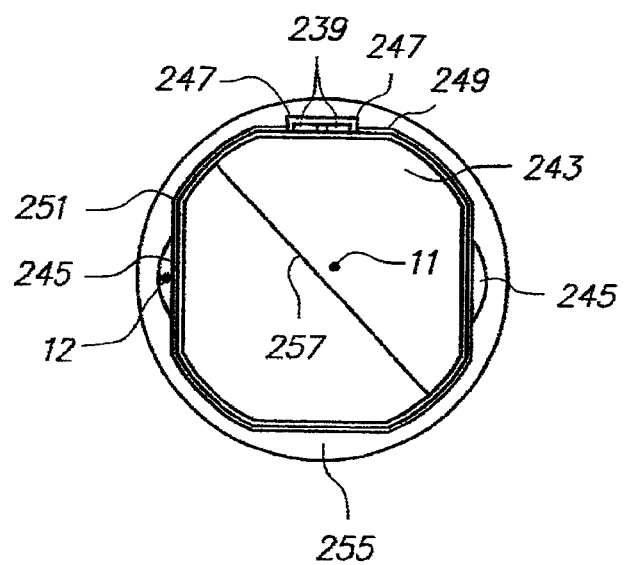
Figure 17F:
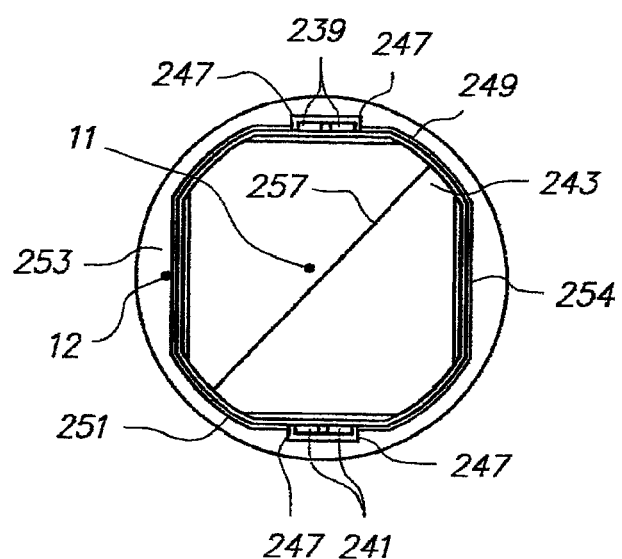
Figures 2, 17G:
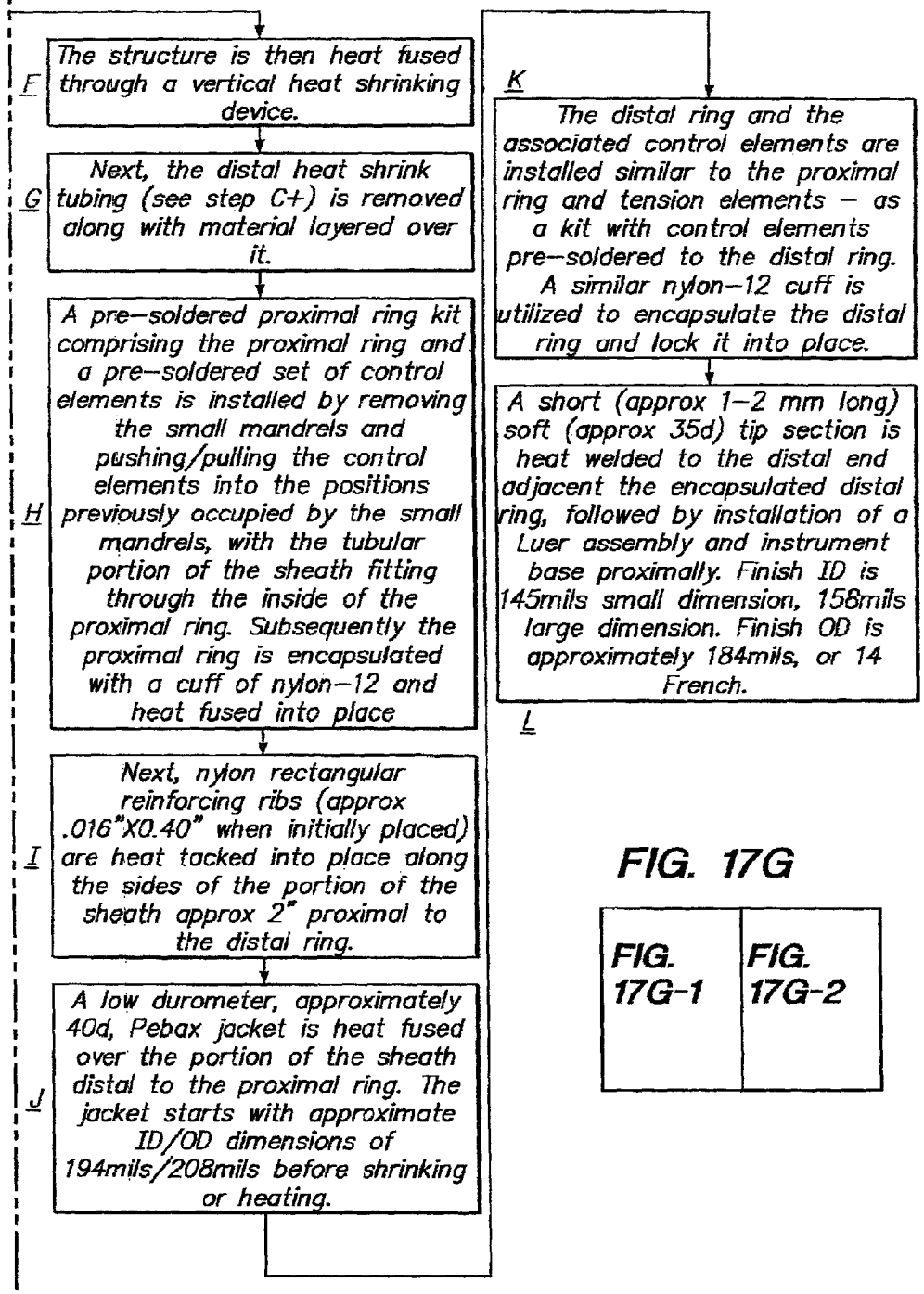
Figure 17G:
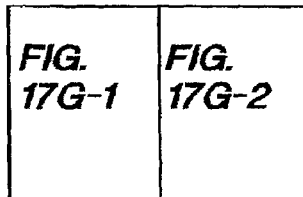

Referring to FIGS. 17A-F, two sheath instrument integrations are depicted, each comprising a single optical fiber (12). FIG. 17G depicts an integration to build such embodiments. As shown in FIG. 16C, in Step "B", a mandrel for the optical fiber is placed, subsequent to which (Step "K") an optical fiber with Bragg gratings is positioned in the cross sectional space previously occupied by the mandrel (after such mandrel is removed).

Figure 18:
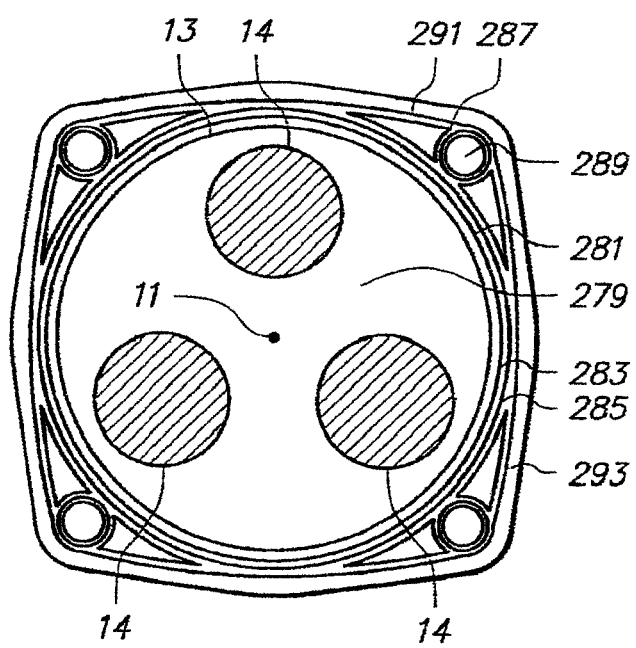
FIG. 18 illustrates a cross-sectional view of a bundle of optical fiber within the working lumen of a catheter.

Referring to FIG. 18, in another embodiment, a bundle (13) of fibers (14) may be placed down the working lumen of an off-the-shelf robotic catheter (guide or sheath instrument type) such as that depicted in FIG. 18, and coupled to the catheter in one or more locations, with a selected level of geometric constraint, as described above, to provide 3-D spatial detection.

Tension and compression loads on an elongate instrument may be detected with common mode deflection in radially-outwardly positioned fibers, or with a single fiber along the neutral axis of bending. Torque may be detected by sensing common mode additional tension (in addition, for example, to tension and/or compression sensed by, for example, a single fiber coaxial with the neutral bending axis) in outwardly-positioned fibers in configurations such as those depicted in FIGS. 12A-H.

In another embodiment, the tension elements utilized to actuate bending, steering, and/or compression of an elongate instrument, such as a steerable catheter, may comprise optical fibers with Bragg gratings, as compared with more conventional metal wires or other structures, and these fiber optic tension elements may be monitored for deflection as they are loaded to induce bending/steering to the instrument. Such monitoring may be used to prevent overstraining of the tension elements, and may also be utilized to detect the position of the instrument as a whole, as per the description above.

Figure 19B:
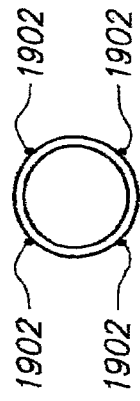
FIG. 19B illustrates a cross sectional view of the catheter.
Figure 19D:
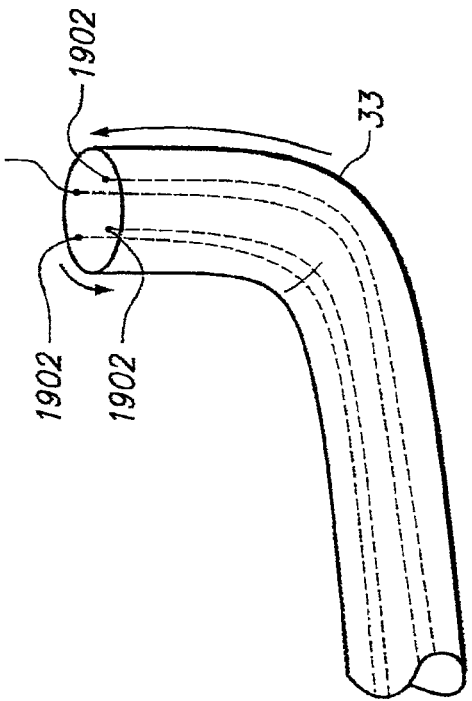
FIG. 19D illustrates that the control wires are activated to steer the catheter.
Figure 19A:
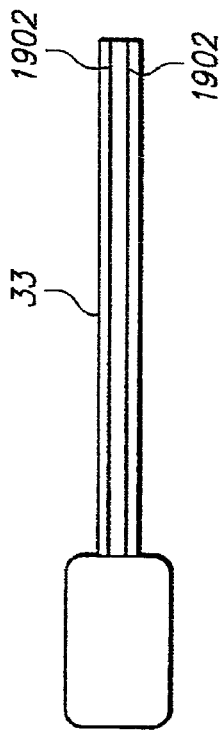
FIG. 19A illustrates a catheter in a neutral position with control wires or pull wires in an inactivated mode.

As previously mentioned, it is highly useful to be able to determine the 3-dimensional spatial positions of elongate instruments such as a catheter that is being used in minimally invasive interventional or diagnostic operations so as to monitor the 3-dimensional spatial position of the catheter relative to other structures, such as pertinent tissue structures, other instruments, the operating table, particular reference points, etc. In advancing and steering or bending an elongate instrument such as a catheter through tortuous pathways, such as various body lumens, or inside an organ, such as a chamber of a heart, to perform various interventional or diagnostics operations inside a patient, the steering or bending movements may produce or induce twisting or torsional forces to the elongate instrument. In addition, twist may also be induced by contact with tissue. Twisting of the elongate instrument may cause the distal tip of the elongate instrument to be displaced to an unintended or unaccounted for positions. FIG. 19A illustrates a catheter (33) in a neutral position with control wires or pull wires (1902) in an inactivated mode. FIG. 19B illustrates a cross sectional view of catheter (33).

Figure 19C:
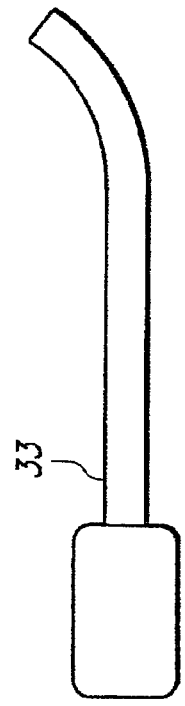
FIG. 19C illustrates the distal tip of the catheter being steered or bended upwardly by activating control wires.
Figure 19E:
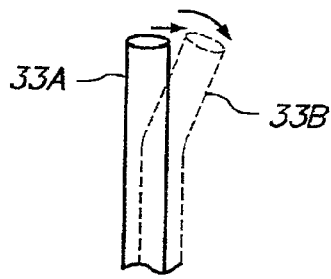
FIG. 19E illustrates the different resultant positions of the distal tip of the catheter.

FIG. 19C illustrates the distal tip of the catheter (33) being steered or bended upwardly by activating the control wires (1902). FIG. 19D illustrates that as the control wires (1902) are activated to steer or bend the distal portion of the catheter (33) in an upwardly direction, the tensioning of the control wires (1902) may also produce or induce torsional or twisting forces at the distal section such that the distal portion of the catheter (33) may not be steered or bended only in an upwardly movement, but also in a twisted or rotated movement. Accordingly, the resultant displacement of the distal tip of the catheter (33) due to the steering control to bend in an upwardly manner may include components of upward and twisted or rotated displacements. FIG. 19E illustrates the different resultant positions of the distal tip of the catheter (33); where catheter (33A) is shown to be displaced upwardly only, whereas catheter (33B) is shown to be displaced including the twist or rotational displacement.

The twisting or rotational displacement of an elongate instrument, such as a catheter, may also induce stress or strain on an optical fiber with Bragg gratings in addition to stress or strain induced by bending as the example illustrated in FIGS. 19A-19E. Unless the data from the Bragg gratings can be parsed into identifiable components of reflected optical readings from stress or strain due to bending and reflected optical readings from stress or strain due to twist or torsion, the displacement information determined from the optical data will include inherent inaccuracy or error in estimating the position or shape of the elongate instrument. Accordingly, in order to accurately estimate or predict the position or shape of an elongate instrument as discussed by using optical fibers with Bragg gratings, one must account for the potential of induced twist or rotation of the elongate instrument when it is steered or bended as well as tissue contact while executing various interventional or diagnostic procedures.

Figure 20:
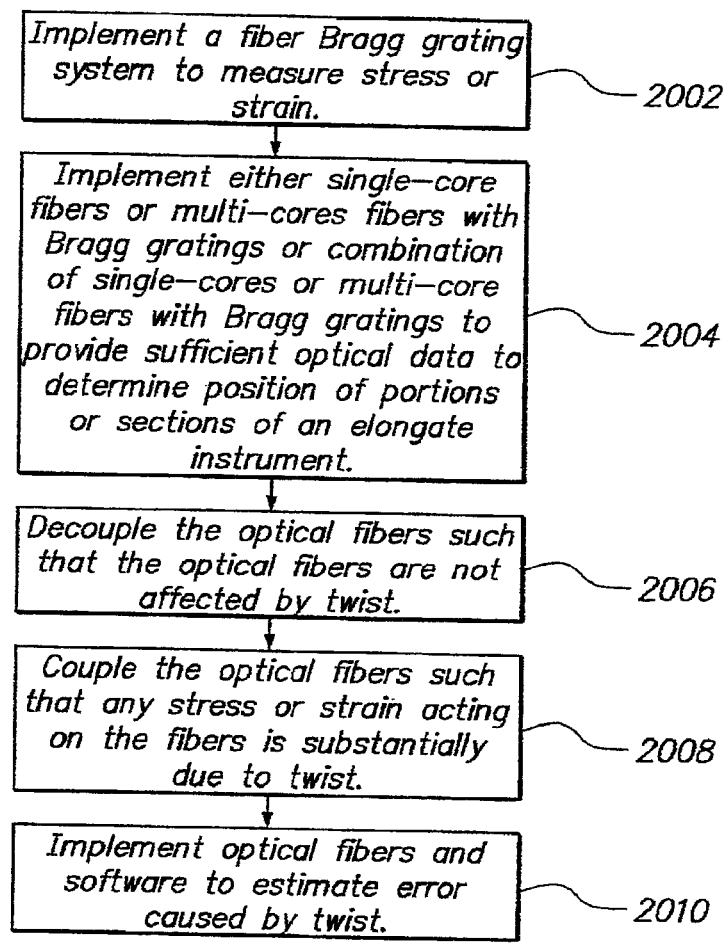
FIG. 20 illustrates a flow chart of a process to address twist or rotation of an elongate instrument.
Figure 21A:
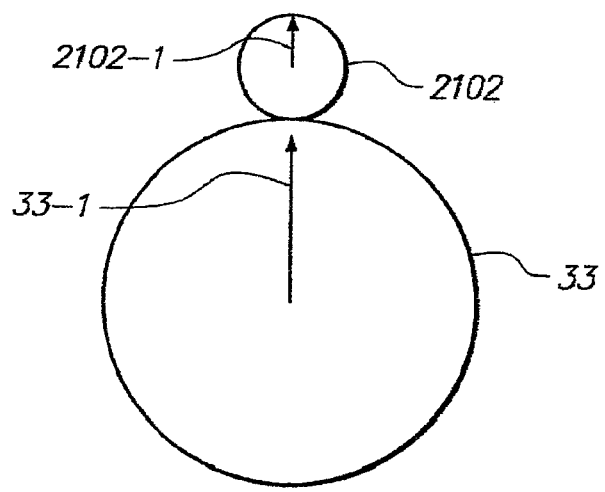
FIGS. 21A-21B illustrate an optical fiber that is rotationally decoupled from an elongate instrument.
Figure 21B:
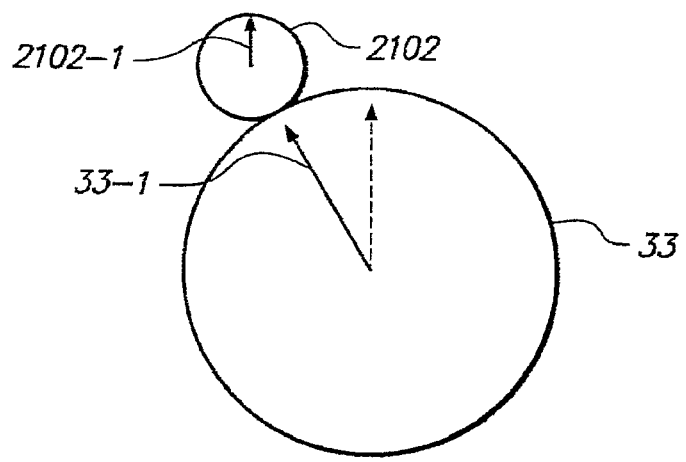
Figure 21C:
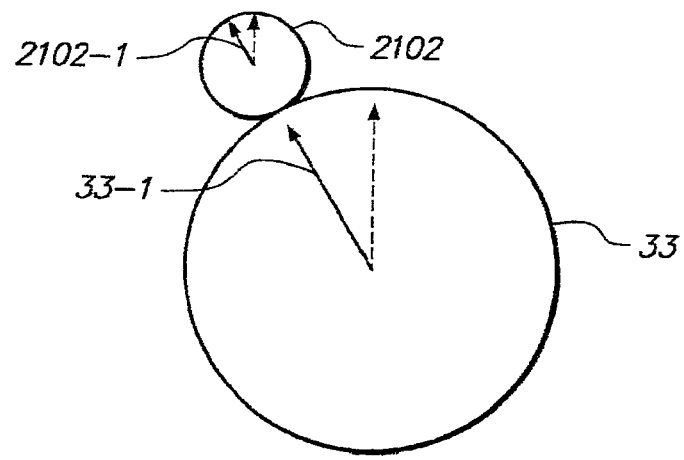
FIG. 21C illustrates an optical fiber that is rotationally coupled to an elongate instrument.

FIG. 20 illustrates a flow chart of a process to address twist or rotation of an elongate instrument using optical fiber Bragg grating to determine position of sections or portions along the length of an elongate instrument. As illustrated in FIG. 20, in Step 2002, an optical fiber Bragg grating system, such as any of the configurations discussed above as well as any of the configurations to be discussed below is implemented on an elongate instrument such that position of sections along the length of an elongate instrument may be determined. As explained in Step 2004, the implementation of an optical fiber Bragg grating system may be comprised of single-core optical fibers, multi-core optical fibers, or combination of single core and multi-core optical fibers. To be discussed in further detail, there are various embodiments to address the potential error or uncertainty that may be induced by twist or rotation of the elongate instrument. As indicated in Step 2006, twist or rotation may be addressed by decoupling the optical fibers from the elongate instrument. That is any twist or rotation of the elongate instrument is not transferred or induced onto the optical fibers. Referring to FIG. 21A, it illustrates a cross-sectional view of an elongate instrument (33) and an optical fiber (2102) that is decoupled to the elongate instrument (33). Both the elongate instrument (33) and optical fiber (2102), as illustrated in FIG. 21A, are in a neutral or initial state as indicated by the markers (33-1) and (2102-1). FIG. 21B illustrates that the elongate instrument (33) has been steered or bended in a particular direction and the steering or bending as executed by control or pull wires (not shown) have induced twist to the elongate instrument. Twisting of the elongate instrument is illustrated by displacement of the marker (33-1). Since the optical fiber (2102) is decoupled from the elongate instrument (33), the optical fiber is not affected by twist or rotation of the elongate instrument. As the optical fiber marker (2102-1) indicates, the optical fiber (2102) did not experience any twist or rotation. On the other hand, if the optical fiber (2102) was not decoupled from the elongate instrument, it may be induced to twist or rotate as illustrated in FIG. 21C. Depending on how the optical fiber (2102) is coupled to the elongate instrument (33), there might be substantial one-to-one correspondence as to the induced twist of the optical fiber (2102) from the elongate instrument (33). In some configurations, the induced twist of the optical fiber (2102) from the elongate instrument (33) might be substantially less than one-to-one.

Figure 22A:
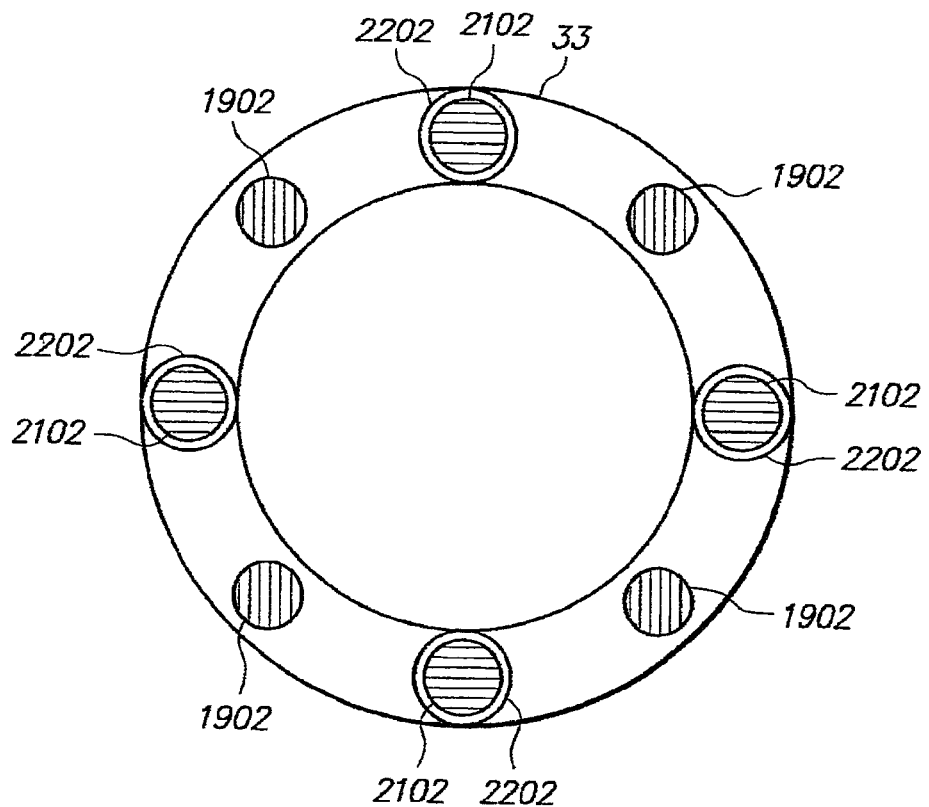
FIG. 22A illustrates the cross section of an elongate instrument.
Figure 22B:
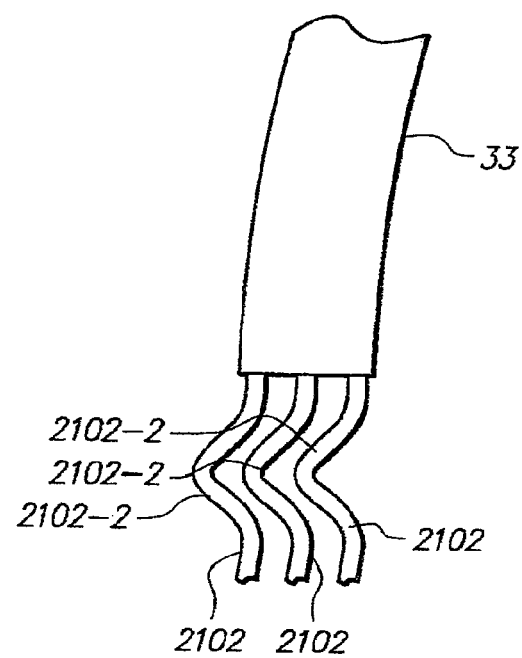
FIG. 22B illustrates optical fibers with service or buffer loops.

Still referring to Step 2006 of FIG. 20, there are numerous implementations in which optical fibers may be decoupled from the elongated instrument such that twist is not induced from the twisting or rotating of the elongate instrument to the optical fibers. As may be appreciated, the optical may be sufficiently stiff or rotational stiffness such that the optical fibers may not be easily twistable. Examples provided herein are by no means exhaustive or limiting, but for illustration purposes only. In one embodiment, as illustrated in FIG. 22A, elongate instrument (33), which may be a catheter, a guide, or sheath, includes control or pull wires (1902) and optical fibers (2102). The optical fibers (2102) may be disposed in lumens (2202) that have substantially smooth, non-binding, or frictionless wall surface, such that no torsional force is induced or transferred to the optical fibers to cause them to twist or rotate, hence inducing stress or strain due to twist or rotation to the optical fibers. In another embodiment, as illustrated in FIG. 22B, the optical fibers (2102) may include service or buffer loops (2102-2) near the proximal end of the elongate instrument (33), such that any steering or bending movements of the elongated instrument would not cause the optical fibers to bind or couple (e.g., by tension, friction, etc.) to the elongate instrument in a way that could result in transfer of torsion or rotation forces to the optical fibers to cause the optical fibers to twist or rotate. In addition, the optical fibers (2102) may be implemented such that they could slide substantially freely in and out of the lumens (2202) of the elongate instrument (33). Furthermore, the optical fibers (2102) may be secured near the proximal end by rotatable fasteners or couplers, such as ball-bearing collar, swivel joint or collar, universal joint or collar, etc., so as to prevent binding or coupling.

Figure 23:
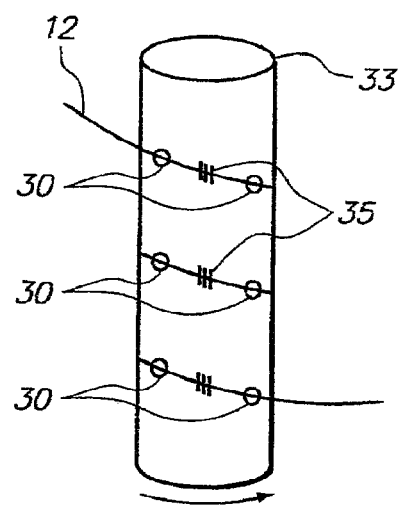
FIG. 23 illustrates a cylindrical structure with a spirally wound array of fiber grating sensors to measure twist.
Figure 24:
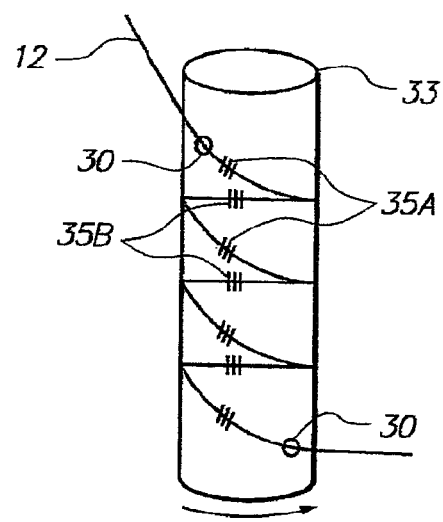
FIG. 24 illustrates a cylindrical structure with a variable pitch spirally wound array of fiber gratings to measure twist and axial strain.
Figure 25:
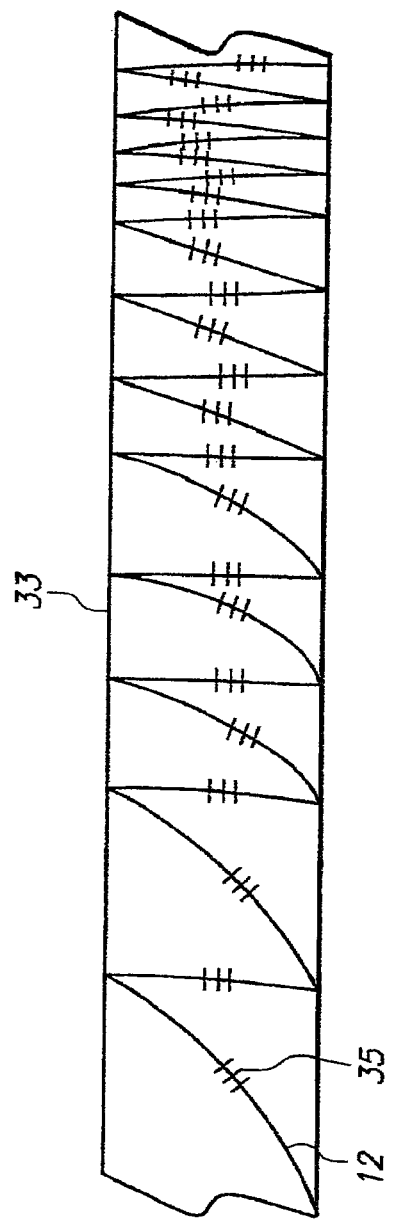
FIG. 25 illustrates an elongate instrument being wound with an optical fiber at variable pitch and spacing along its length.

Referring back to FIG. 20, in particularly Step 2008, optical fibers with Bragg gratings may be coupled to an elongate instrument such that stress or strain acting on the fibers is substantially due to twist; hence, such configuration or implementation of the fibers would enable the determination of twist or rotational displacement of the elongate instrument. FIG. 23 illustrates one embodiment of using an optical fiber (12) with Bragg grating sensors (35) to measure compression or tensile stress to determine twist or torsion in an elongate member (33). Optical fiber (12) may be constrained to the elongate member (33) at attachment points (30) or in another embodiment, optical fiber (12) may be adhered to elongate member (33) in a continuous manner instead of being attached at discrete locations. As the elongate member (33) is twisted (e.g., due to steering or bending) the fiber gratings (35) are exposed to either axial tension or compression depending on the direction of twist that is applied to the elongate member (33). In the case where the fiber is bonded directly to the elongate member (33) tension and compression may be measured directly. When attachment points are used to bond or couple the optical fiber (12) to the elongate member (33) it may be necessary to pretension the optical fiber (12) with sufficient tension such that full range of compression encountered may be measured without the optical fiber (12) becoming unloaded such that the full compression may be measured. As shown in FIG. 23, the pitch at which the optical fiber (12) is wound around the elongate member (33) is substantially constant. However, the pitch of the wound for optical fiber (12) need not be constant. As shown in FIG. 24, the optical fiber (12) is wound with variable pitch in a spiral manner. When the optical fiber (12) is wound with variable pitch, the response of the fiber gratings (35) to twist would depend upon the localized pitch of the spiral. As illustrated in FIG. 24, due to the pitch of the spiral of optical fiber (12), fiber gratings (35A) may be exposed to compression or tensile stress due to axial loading as well as twist or torsional loading, whereas fiber gratings (35B) may be exposed to substantially twist or torsional loading only. In this manner both the strain or stress due to twist and the strain or stress due to axial tension or compression along the length of the elongate member (33) may be measured. In other embodiments, optical fibers may be wound around an elongated member with variable spacing or tightness. That is the optical fibers may be wound in larger or further apart spirals or smaller or closer together spirals. For example, in a section of the elongate instrument, e.g., the proximal portion, where elongate instrument may be stiffer or less flexible or less maneuvered, the optical fibers may be wound with larger or further apart spirals. On the other hand, in a section of the elongate instrument, e.g., the distal section, where the elongate instrument may be more flexible or where greater steering or maneuvering is executed, the optical fibers may be wound with smaller or closer spirals to obtain increased optical data to determine the position and orientation of the distal section or tip of the elongate instrument. For instance, FIG. 25 illustrates an elongate instrument 33 where optical fiber (12) is wound with variable pitch along its length. In addition, the optical fiber (12) is wound with larger or further apart spirals near the proximal portion, while the optical fiber (12) is wound with smaller or closer together spirals near the distal portion.

Figure 26:
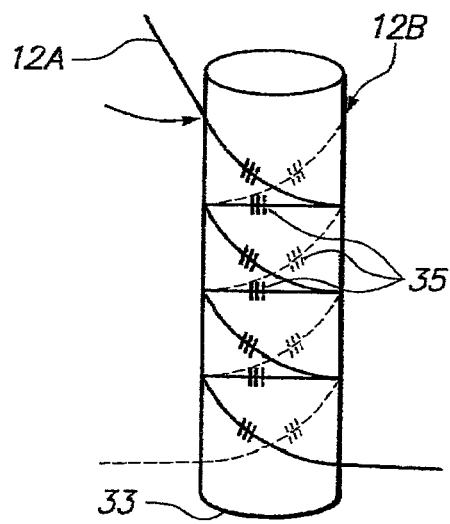
FIG. 26 illustrates a cylindrical structure with two spirally wound arrays of fiber gratings arranged to that strain rosettes are formed on the cylinder for multi-dimensional strain measurements.

FIG. 26 shows how two spirally wound optical fibers (12A and 12B) may be wound around an elongate member (33) in opposite directions. One of these optical fibers (12A) may be wound with variable pitch (e.g., in a manner similar to that shown in FIG. 24). A second optical fiber 12B may be wound in the opposition direction with constant pitch (e.g., in a manner similar to the constant pitch example as illustrated in FIG. 23). Fiber gratings can be incorporated on these two optical fibers (12A and 12B) so that localized strain rosettes are formed along the length of the elongate member (33) providing a means for three dimensional strain or stress measurements to be performed along the length of the elongate member (33).

Figure 27:
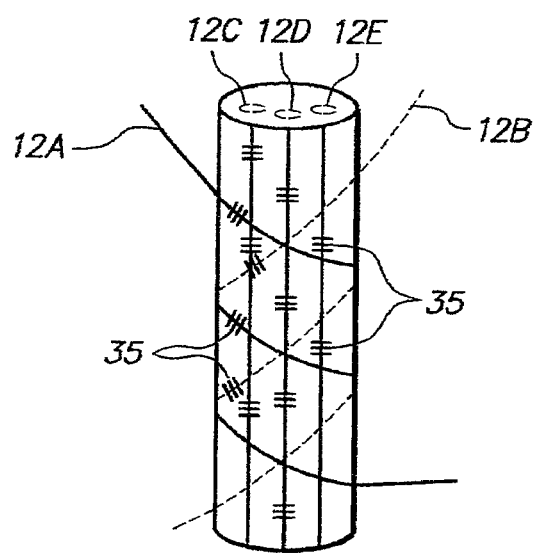
FIG. 27 shows five grating arrays; three parallel to the long axis of the cylinder to measure bending and two spirally wound to measure twist.

FIG. 27 illustrates one embodiment that is configured for measuring bending and twist using two spirally wound optical fibers (12A and 12B) and three additional optical fibers (12C), (12D), and (12E) substantially axially oriented that are attached either to the interior or exterior of the elongate member (33). As may be appreciated, the elongate instrument (33) as described may be a catheter sheath, catheter guide, or catheter instrument. Catheter sheath and catheter guide may be hollow instruments having a lumen or channel where surgical instrument may be disposed, advanced, and steered toward a target operational site. Optical fibers (12A) may be disposed, coupled, secured, etc. on either the exterior or interior surface of the sheath or guide. On the other hand, a catheter guide and catheter instrument may be non-hollow elongate instruments where certain surgical instrument may be incorporated as part of the catheter guide or catheter instrument. In such applications, optical fibers may be disposed, coupled, secured, etc. on the exterior surface of the catheter guide or catheter instrument or optical fibers may be incorporated into the internal construction of the catheter guide and configured in the various manners (e.g., axial, spiral, cross spiral, constant pitch, variable pitch, spaced far apart, closely spaced apart, etc.) as described in this description.

Still referring to FIG. 27, the three axial optical fibers (12C), (12D) and (12E) are arranged to be spaced about or near the periphery of the elongate member (33) so that bend moments may be measured by using fiber grating arrays that are incorporated and spaced-apart along the length of axial optical fibers (12C), (12D), and (12E). Twist could be measured by a single spirally wound fiber with gratings similar to that shown in FIG. 23 or a dual spiral configuration that allows twist and axial strain or stress measurements that could be used to supplement and augment the axial strain or stress measurements of the optical fiber grating arrays along the axis of the elongate member (33).

One advantage of using separated arrays of fiber gratings is that for objects of larger size is that the fiber grating sensors may be placed in locations or positions for optimum strain sensitivity. In some practical applications, space may be at a premium and the dimensions of the optical fiber used may be significant with respect to the size of the overall structure. In these cases, it would be highly desirable to be able to minimize the number of optical fibers used to gather data to determine bend and twist measurements. For example, in a medical device application, it would be highly desirable to minimize the overall diameter of a catheter for performing minimally invasive interventional or diagnostic procedures. In this case, even a millimeter increase in overall diameter may be significant for a medical device such as a catheter that is used in the minimally invasive interventional or diagnostic procedure. One approach as suggested above, various types of surgical instruments (e.g., ablation electrode, irrigated ablation electrode, needle, cutting tool, etc.) may be incorporated to the catheter to eliminate the need of a through lumen and reduce the overall size and diameter of the catheter surgical system. Another approach to keep the invasive medical device as small as possible would be to combine optical techniques into a single optical fiber for measuring both bend and twist. This approach would reduce the number of fibers required for accurate determination and monitoring of the 3-dimensional shape and position of the medical device, and minimize the impact of the fiber grating sensor array on the overall size of the invasive medical device. Another approach to reduce or minimize overall size one or more optical fibers may be incorporated into the structure of the elongate instrument. For example, one or more optical fibers with Bragg gratings may incorporated or woven with the braiding of a catheter.

Figure 28:
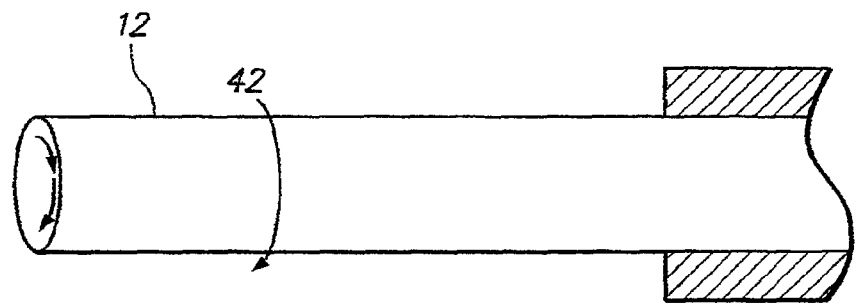
FIG. 28 illustrates an optical fiber constrained at one end and twisted to induce circular birefringence.
Figure 29:
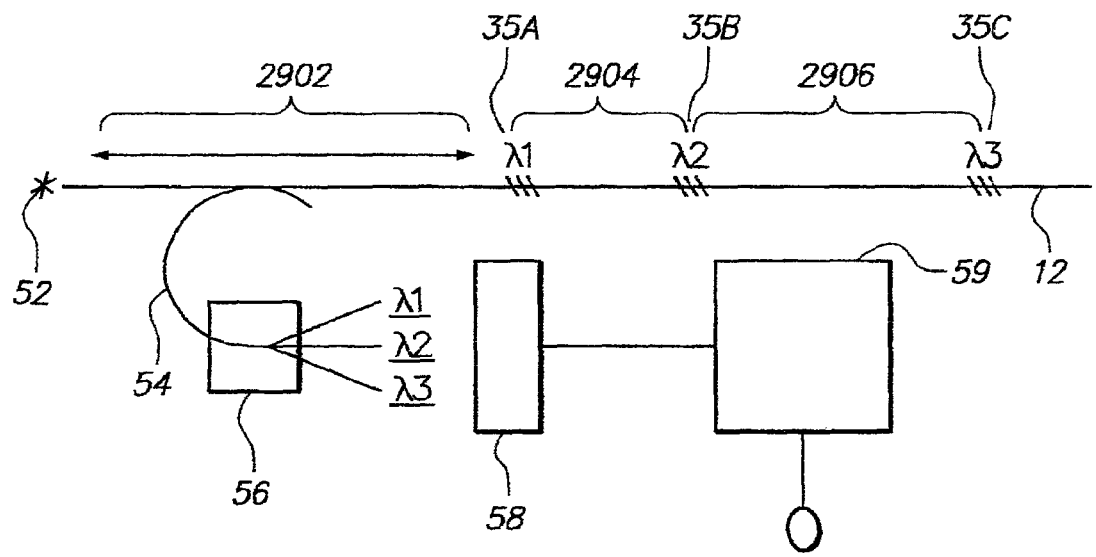
FIG. 29 illustrates a system to measure twist based on changes of the birefringence of an optical fiber being twisted, wherein fiber gratings are used in separate sections of the fiber to enable wavelength division multiplexing to analyze separate sections of the fibers based on their respective polarization states.

As it is highly desirable to be able to measure twist in an optical fiber that is simultaneously capable of measuring bend, FIG. 28 illustrates a method of measuring twist of an optical fiber along its longitudinal axis in accordance with one embodiment of the present disclosure. As illustrated in FIG. 28, an optical fiber (12) is constrained at one end and a twist or torsional load (42) is applied to the optical fiber (12). This results in a rotationally induced strain that causes the optical index of refraction to vary in a circular manner. This circular variation in the index of refraction is called circular birefringence and it can be used to advance or retard the phase of circularly polarized light which propagates along the length of the optical fiber (12). By measuring the change in the circular birefringence of the optical fiber induced by twist or torsional load (42), the amount or degree of twist of the optical fiber (12) may be measured by conventional optical instruments. In some instances, it is desirable to measure the twist of the optical fiber (12) in a periodic manner along the length of the optical fiber (12). Under such circumstance, the optical fiber (12) may be divided into sections via fiber gratings as illustrated in FIG. 29. In this case, a light source (52) which may be a tunable laser sweeps over a wavelength range or a spectrally broad super-radiant diode, or a fiber light source (52) that operates continuously over a broad spectral band may be used to launch one or more selected polarization states into the optical fiber (12). This light could be a circularly polarized light or it could be an ensemble of polarization states that are later separated. The light beam propagates along optical fiber (12) in which it is launched by an optical coupler (54) to a fiber grating (35A) of wavelength 1. The optical coupler (54) may be a 2 by 2 coupler or an optical circulator. A portion of the optical beam corresponding to wavelength 1 and the "lead" section (2902) of the optical fiber is reflected back by the fiber grating (35A) of wavelength 1 to the coupler (54) and directed to a wavelength division multiplexing element (WDM) (56) that splits out wavelength 1 to a port of an optical switch (58) corresponding to this wavelength. The optical switch (58) in turn directs the light at wavelength 1 to a polarization analyzer (59) that is used to measure the change in polarization state induced by twist of the "lead" length of the optical fiber and in turn determine a twist output for this section of the optic fiber (12). In a similar manner, a portion of the light source optical beam is reflected by the fiber grating (35B) at wavelength 2 after it propagates through the optical fiber (12) passes the lead section and section 1 (2904). The reflected light beam from the fiber grating (35B) at wavelength 2 then propagates back through the coupler (54) to the WDM (56) where it is directed to the switch port corresponding to wavelength 2 at the optical switch (58). The switch (58) then directs this light beam at wavelength 2 to the polarization analyzer (59) that extracts the degree of twist from the fiber length corresponding to the lead (2902) and section 1 (2904). In a further similar manner, the reflected beam from the fiber grating (35C) at wavelength 3 is analyzed to extract the twist from the lead (2902) plus section 1 (2904) and section 2 (2906). This can also be done by using an $n^{th}$ grating along the optical fiber to determine the degree of twist for the optical fiber between the light source and the $n^{th}$ optical fiber grating. By subtracting the degree of twist between adjacent sections, the degree of twist for each separate section may be determined. As an example, the degree of twist for the optical fiber (12) along section 1 (2904) may be determined by factoring out the degree of twist from the lead section (2902) (determined by using the light from the fiber grating (35A) at wavelength 1) from the degree of twist from the lead section (2902) plus section 1 (2904) (determined by the light from the fiber grating (35B) at wavelength 2). It should be noted that a polarization analyzer (59) may be constructed to have multiple ports so that each reflected wavelength could be monitored continually without the need of an optical switch.

Figure 30A:
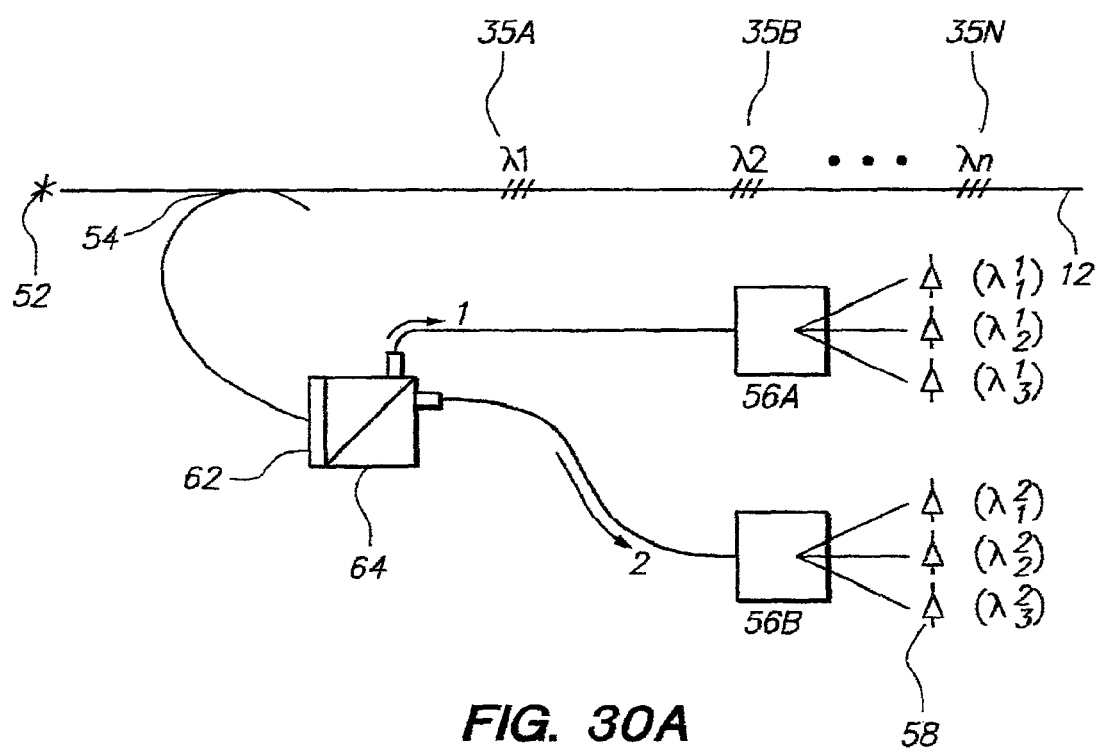
FIG. 30A illustrates an implementation of a system to measure twist based on a fiber grating array and a polarization measurement system capable of separating out the regions over which twist is to be measured in the optical fiber via wavelength division multiplexing and analysis of the polarization state of each optical fiber section.
Figure 30B:
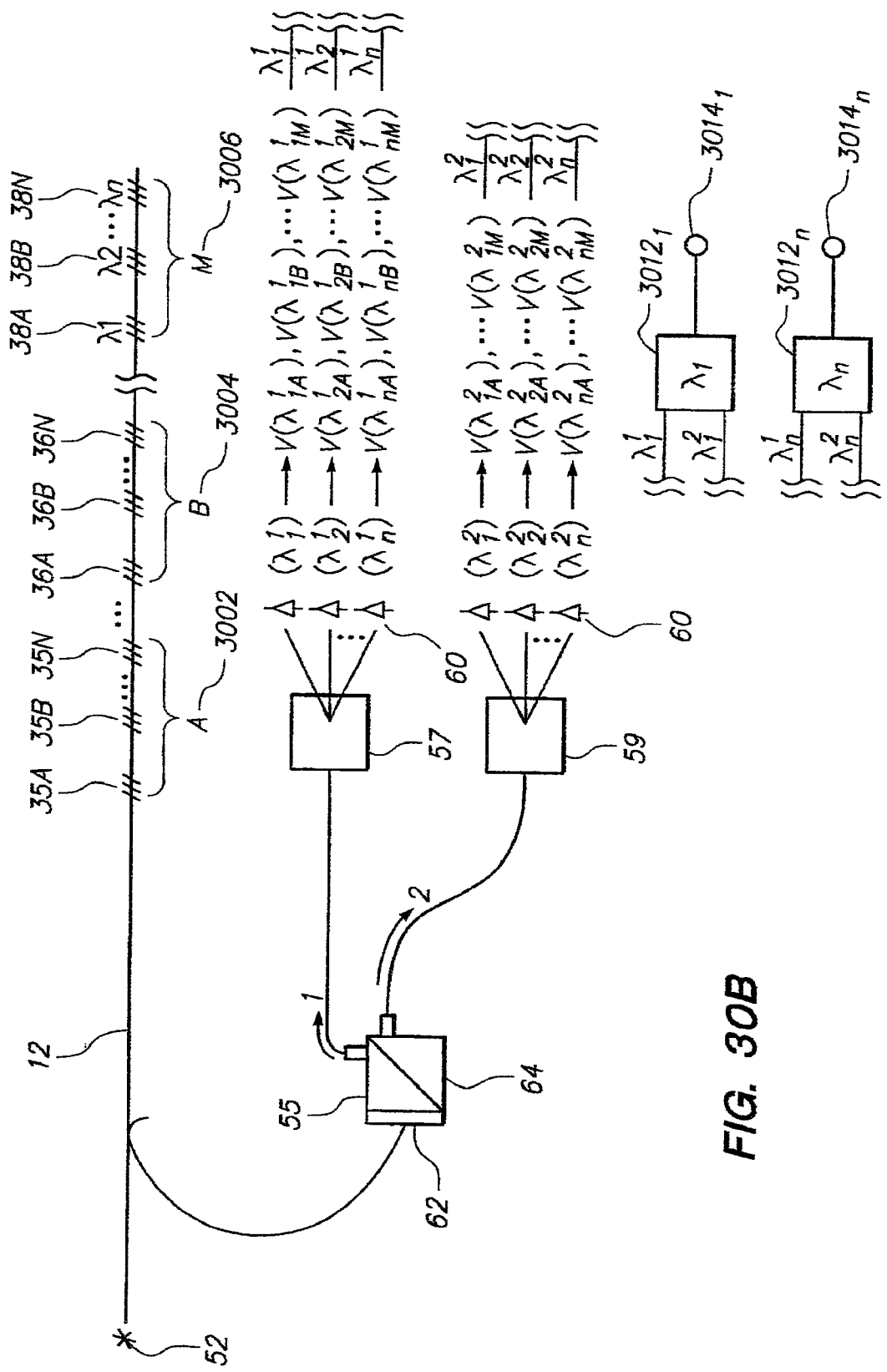
FIG. 30B illustrates a pulsed optical fiber system.

It is possible to utilize a fiber analyzer that is a precision instrument to do a complete polarization analysis of the reflected light beams associated with FIG. 29 to extract twist. However simpler configurations with lesser accuracy are possible. FIG. 30A illustrates an optical system comprising a polarized light source (52) that is configured to launch selected polarization states into an optical fiber (12) which couples a light beam to fiber grating array with n numbers of fiber gratings (35A, 35B, . . . , 35N) of wavelengths 1, 2 . . . n. The reflected light beams are directed via a coupler (54) into a simple polarization analyzer that comprises of an optical wave plate (62) (that may be used to convert circularly polarized light to linear polarized light) and a polarization beam splitter apparatus (64) which separates out the two orthogonal linear polarization states, such as s and p, into light beams 1 and 2 that may be directed to the WDM element 1 (56A) and WDM element 2 (56B) which in turn split the light beam into wavelength components 1 through n. These optical light beams may then be directed to detectors (58) which convert the optical signals to electrical signals for processing. The hardware and software for electrical signal processing are not shown or discussed here, but will be discussed below. Referring to the converted optical signals, in particular amplitude of the s polarization component at wavelength n can be compared to the amplitude of the p polarization component at the wavelength n to extract the polarization changes induced by twist of the optical fiber between the light source and the fiber grating of wavelength n. By comparing the subsequent section signals the twist along the fiber length may be measured. This approach may be extended to provide more twist measurement points by implementing a system using time division as well as wavelength division multiplexing as illustrated in FIG. 30B. FIG. 30B illustrates an optical system comprising a pulsed light source (52). The pulsed light source may be configured to provide substantially short pulses of light that may be on the order of one nanosecond during or less. The pulses of light are propagated down the optical fiber (12) to the M sets of n fiber gratings, such as (A (3002), B (3004), . . . , M (3006), of n gratings (35A, 35B, . . . , 35N, 36A, 36B, . . . , 36N, 38A, 38B, . . . , 38N), that are centered at n distinct wavelengths. The reflected light beam from each of these M sets (3002, 3004, . . . , 3006) of n gratings (35A, 35B, . . . , 35N, 36A, 36B, . . . , 36N, 38A, 38B, . . . , 38N) then passes through a polarization analyzer (55), which may be comprises of an optical wave plate (62) and a polarization beam splitter apparatus (64), where two orthogonal linear polarization states 1 and 2, such as s and p, are directed toward wavelength division multiplexing (WDM) elements 57 and 59, e.g., WDM elements, that are configured to divide out the n number of wavelengths onto n number of detectors ($60_1$, $60_2$, . . . , $60_n$). Each pulse from the light source (52) results in M number of return pulses from the fiber gratings associated with each of the wavelength bands 1, 2, . . . , n with each of these return pulses corresponding to the $A^{th}$ (3002) through the $M^{th}$ (3006) sets. Through the processing of the detectors ($60_1$, $60_2$, . . . $60_n$), the optical pulses are processed to provided output voltages associated with each of the fiber gratings and its two orthogonal polarization states, illustrated in FIG. 30B as state 1 and state 2 (e.g., s and p), that depend on twist. For example, the output voltages associated with fiber gratings at wavelength 1 and their two polarization states are directed into a wavelength 1 comparator ($3012_1$), and the relative values of the voltages associated with the signals associated with the polarization states are used to calculate the twist angle at wavelength 1 angle output ($3014_1$). In a similar manner, the outputs from the fiber gratings at wavelength n are calculated by a wavelength n comparator ($3012_n$), and the relative values of the voltages associated with the signals associated with the polarization states are used to calculate the twist angle at wavelength n angle output ($3014_n$). To make this system work in a substantially optimum manner, the reflectivity of the first set, such as set A (3002), may be configured to have relatively low reflectivity, the second, such as set B (3004), may be configured to have slightly higher reflectivity, and so on until the final set, such as set M (3006), may be configured to have the highest reflectivity. As illustrated in this exemplary optical system, there are n gratings in M sets of gratings such that a quantity of n×M number of twist measurement points may be supported by this or similarly configured optical system.

Figure 31:
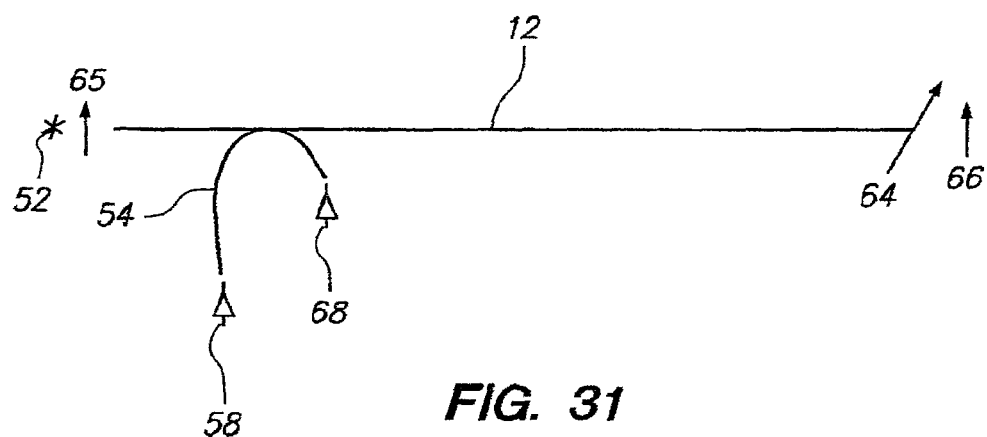
FIG. 31 illustrates a diagram of a twist measurement system which launches light into one end of an optical fiber and analyzes the reflection from a polarization dependent end of the optical fiber that may have been twisted.

Another embodiment for determining or measuring twist is illustrated in FIG. 31. In this embodiment a polarized light source (52) launches light through a polarizing element (65) that may be a linear polarizer into one end of an optical fiber (12). The resultant light beam then propagates past a coupler (54) to a polarizing element (64) at the opposite end of the optical fiber (12), and the light beam is then redirected back toward the coupler (54) by an end reflector (66). The polarized light source (52) may be remotely powered (e.g., electromagnetic energy) and controlled by wireless signals. The polarizing element (64) may be a linear polarizing element that is oriented at 45 degrees relative to the orientation of the input polarizer (65). In this illustration, the polarizing elements (65) and (64) may be linear polarizing elements and their initial orientation may be at 45 degrees twist or rotation at the end associated with the polarizer (65) and end reflector (66) which may result in a change in the relative orientation of the polarizer (64) to the polarizer (65) and the light beam propagating through the system may be amplitude modulated accordingly allowing the measurement of twist via the output voltage on detector (58). A reference detector (68) may be used to support factoring out changes in the light source and coupling through the coupler element. The detector (58) may be remotely powered (e.g., electromagnetic energy) and/or remotely interrogated via wireless means by a remotely located controller.

Figure 32:
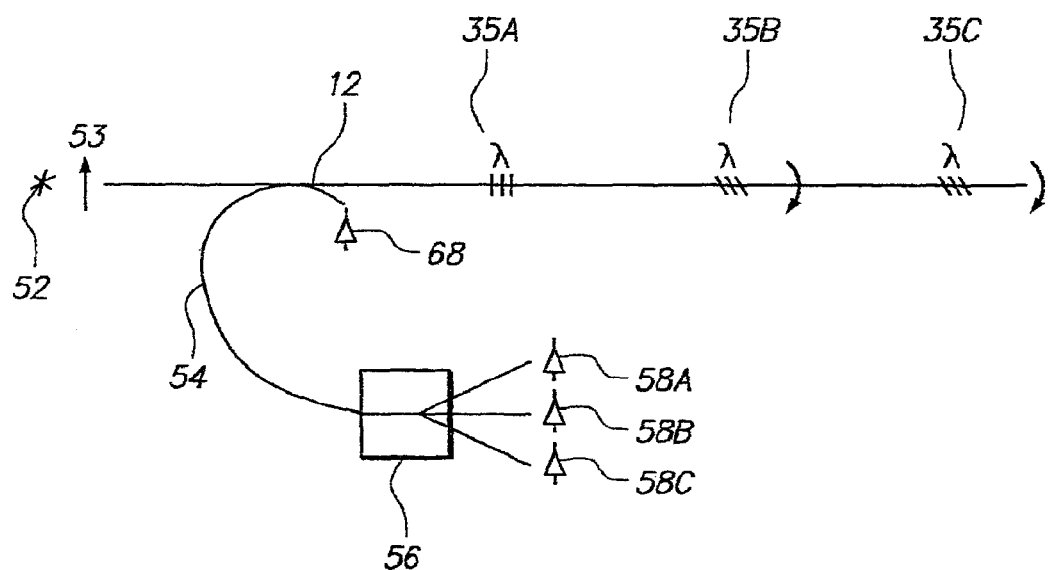
FIG. 32 illustrates a twist measurement system based on an array of fiber gratings that includes fiber grating with significant polarization dependence.

FIG. 32 illustrates another embodiment for measuring twist. This embodiment includes a light source (52), which may be a swept laser system or spectrally broadband continuous light source with an input polarization state defined by the polarizing element (53) which may be a linear polarizing element. A reference detector (68) on one output leg of the coupler (54) may be used to monitor light source fluctuations. The light reflected from the reference fiber grating (35A) which may be designed to be substantially polarization independent may be used to monitor the light source and changes in attenuation due to optical elements associated with the read out portion the system. Further along the optical fiber (12) are fiber gratings (35B) and (35C) which may be designed to be polarization dependent; for example, such means as tilting the fiber gratings relative to the longitudinal axis of the optical fiber. When twist occurs at the fiber gratings (35B) and (35C) their rotational position relative to the input polarization state defined by the polarizing element (53) changes resulting in an amplitude change of the light that reaches the detectors (58B) and (58C) which may be configured to monitor light reflected from the fiber gratings (35B) and (35C) respectively. It should be noted that the exemplary systems illustrated in FIGS. 31 and 32 are designed to measure the state of twist of the optical fiber at various points or locations along the length of an elongate instrument.

The embodiments as described to measure twist by changes in the polarization state of light propagating through an optical fiber illustrated in FIGS. 29 through 32 may be made more effective by initially calibrating the optical fiber. For example, the initial polarization state of an optical fiber may be determined in an initial condition, e.g., a neutral state such as unbent and untwisted state, to characterize the polarization state of the optical fiber. Twists may then be applied to the optical fiber to determine or calibrate the effects of various degrees of twists to the polarization state of the optical fiber. In practical applications, the polarization of an optical fiber with unknown amount of twist may be compared to the initial state of polarization and calibrated polarization due to the various degrees of twist to determine the unknown amount of twist that is actually applied to the optical fiber with unknown amount of twist. In further practical applications, an optical fiber may be exposed to various degrees of twist and bend to estimate or establish another set of calibration information. Accordingly, the effect of polarization due to bend may be determined or calibrated and then factored out to isolate the effect of twist on polarization. For instance, bending loads may be applied to the optical fiber to determine or calibrate the effects of various degrees of bends on the polarization state of the optical fiber. The amount of bend to the optical fiber may be determined by physical measurements or optical frequency domain reflectometry or time/wavelength division multiplexing techniques.

Figure 33A:
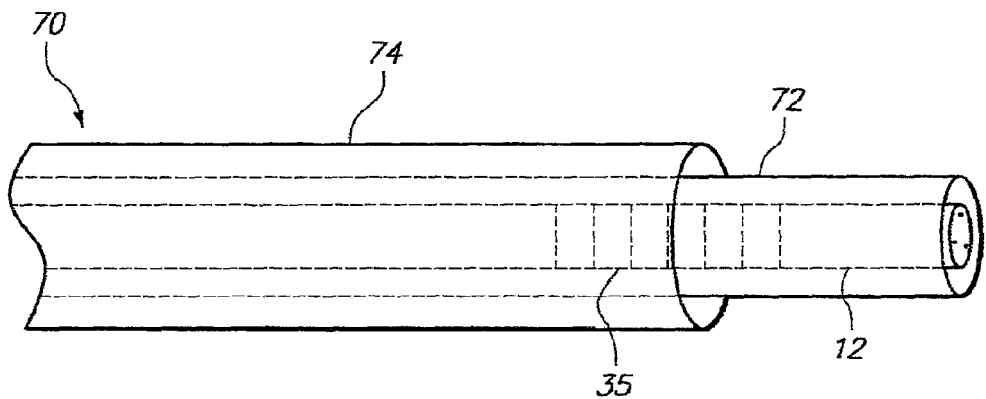
FIGS. 33A-33G illustrate the concept of determining localized bending on an elongate instrument.
Figure 33B:
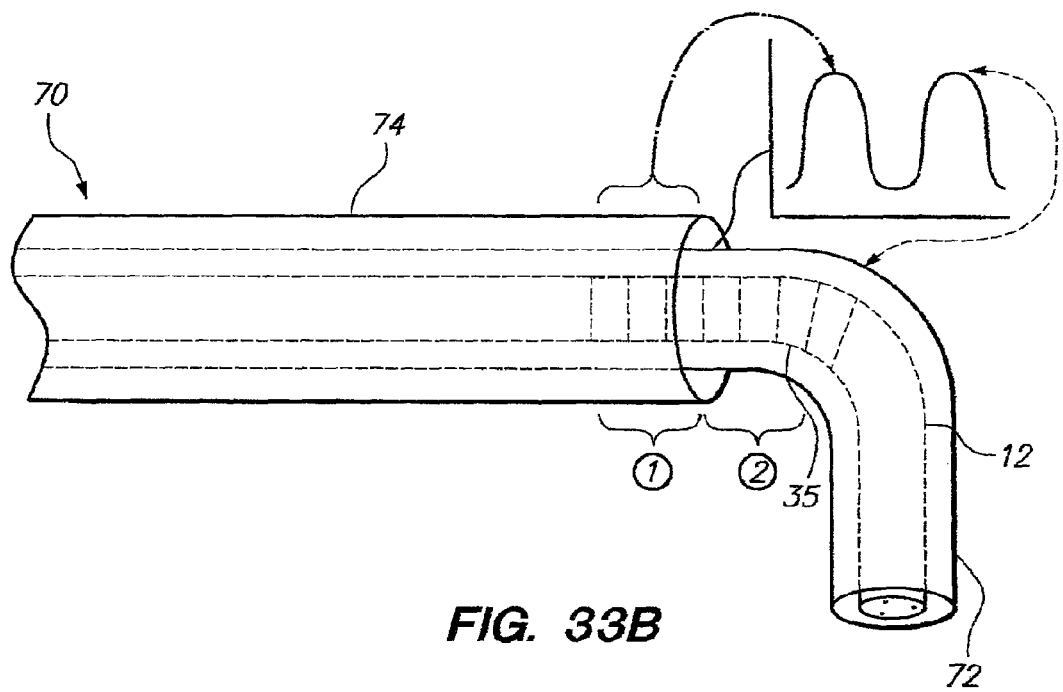
Figure 33C:
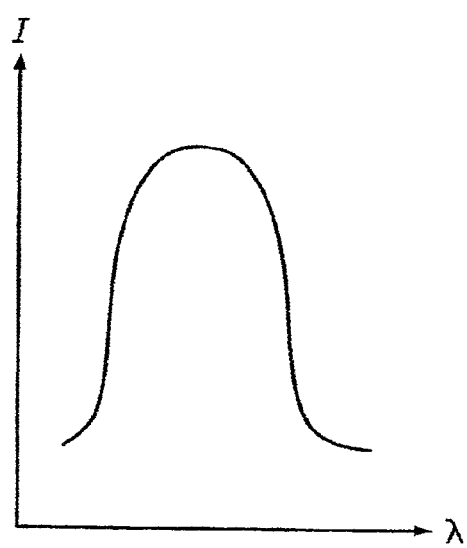
Figure 33D:
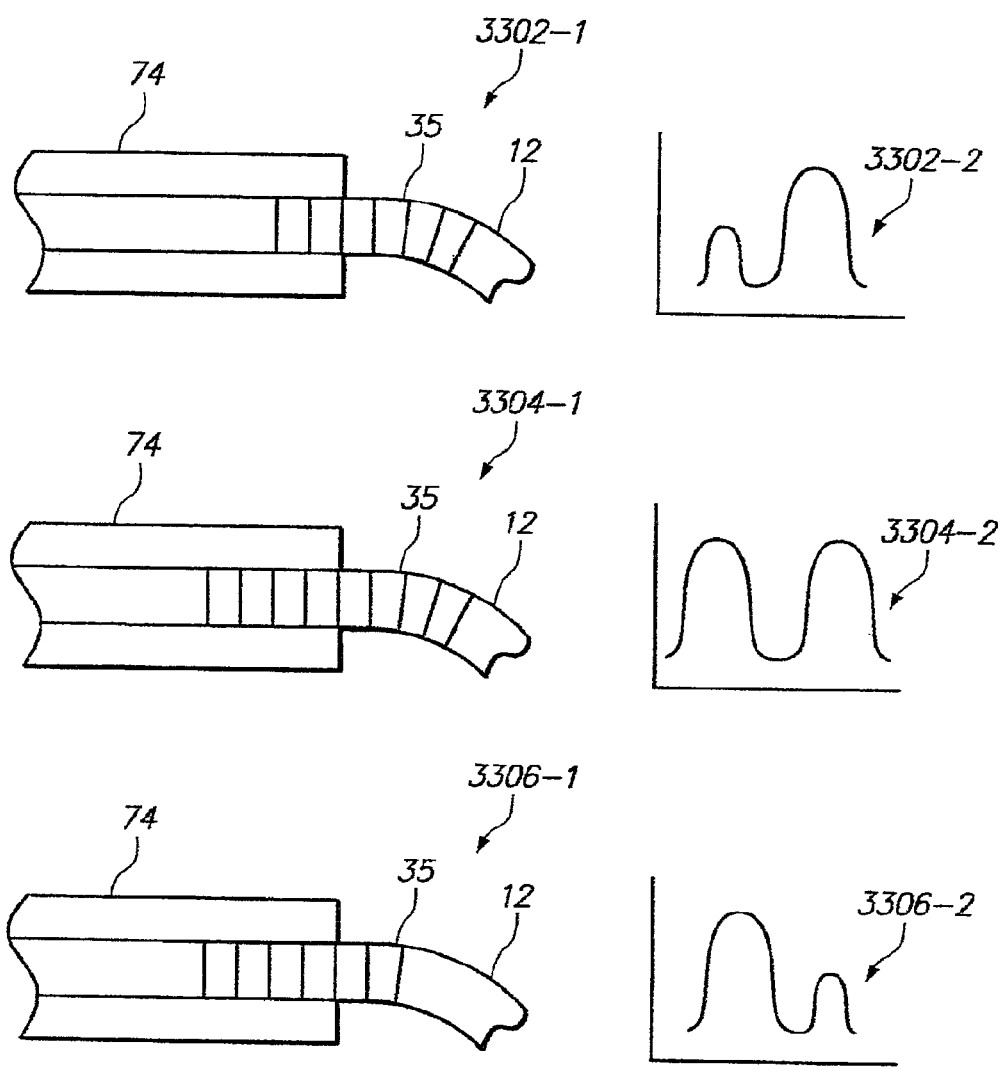

A fiber grating system in accordance with another embodiment may be used to measure localized changes in bend. FIG. 33A and FIG. 33B illustrate elongate member (70), which comprises of an inner cylinder or instrument (72) designed to slide within a stiffer outer cylinder or instrument (74). A multiple core optical fiber (12) or multi-single core optical fibers (12) having one or more fiber gratings (35) that may be mounted at some distance from the central or neutral axis of the inner cylinder or instrument (72) to measure bend as illustrated in FIG. 33B. In one example, as illustrated in FIG. 33A, the instrument (72) with optical fiber (12) may be advanced substantially straight out of the outer cylinder or instrument (74). The spectral signals from the fiber gratings associated with this scenario may consist of a single spectral peak as illustrated in FIG. 33C. In a different example, the inner instrument (72) may be advanced partially out of the outer instrument (74) and the inner instrument (72) is steered or bent at a position where the fiber gratings (35) are partially out of the stiffer outer cylindrical instrument (74) as illustrated in FIG. 33B. Referring to FIG. 33B, the inner instrument (72) may be substantially straight over the area identified as region 1 in the figure, and the inner instrument (72) may be bent with a particular radius of curvature over the area identified as region 2. In this example, the spectral signature from the fiber grating (35) exhibits a signature having split spectral peaks with one of the spectral peaks corresponding to the area or region (region 1) of the fiber where it is substantially straight and the second one of the spectral peaks corresponding the area or region (region 2) of the fiber where the fiber is bent fiber. When the fiber grating position is determined based on a known center wavelength and a measured position along the length of the optical fiber (12), the split spectral peak signature may be used to determine its position relative to the edge of the outer cylinder or instrument (74). Since region 1 (the number of gratings (35) on the straight portion of the fiber (12)) and region 2 (the number of gratings (35) on the bent portion of the fiber (12)), illustrated in this example, are about the same, the amplitudes of the corresponding spectral peaks are about the same. The split spectral peaks signature is illustrated on the inset graph of FIG. 33B. The position of the fiber grating (35) relative to the edge of the outer instrument (74) may be determined by the relative amplitudes of dual spectral peaks or over spectral profile when the optical fiber (12) is bent as shown in FIG. 33D. As illustrated in FIG. 33D, the optical fiber (12) on the inner instrument (72) (not shown in this figure) of the elongate system (3302-1) has about one-third of the gratings (35) on the substantially straight portion and about two-third of the gratings on the substantially bent portion of the fiber. The corresponding split spectral peaks signature (3302-2) illustrates that the amplitude of the straight portion is about one-third the amplitude of the bent portion. Additionally illustrated in FIG. 33D, the optical fiber (12) on the inner instrument (72) (not shown in this figure) of the elongate system (3304-1) has about half or equal number of the gratings (35) on the substantially straight portion and about half or equal number of the gratings on the substantially bent portion of the fiber. The corresponding split spectral peaks signature (3304-2) illustrates that the amplitude of the straight portion is about equal to amplitude of the bent portion. Further illustrated in FIG. 33D, the optical fiber (12) on the inner instrument (72) (not shown in this figure) of the elongate system (3306-1) has about two-third of the gratings (35) on the substantially straight portion and about one-third of the gratings on the substantially bent portion of the fiber. The corresponding split spectral peaks signature (3306-2) illustrates that the amplitude of the straight portion is about twice as high as the amplitude associated to the bent portion.

Figure 33E:
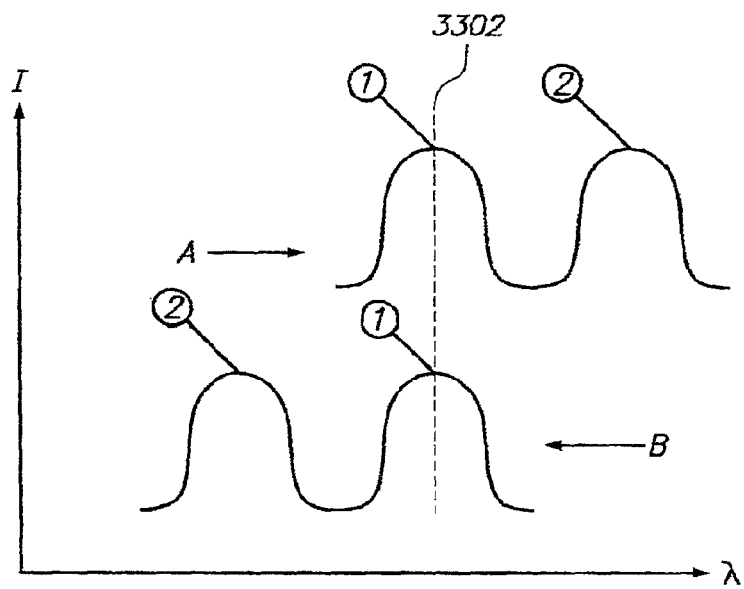
Figure 33F:
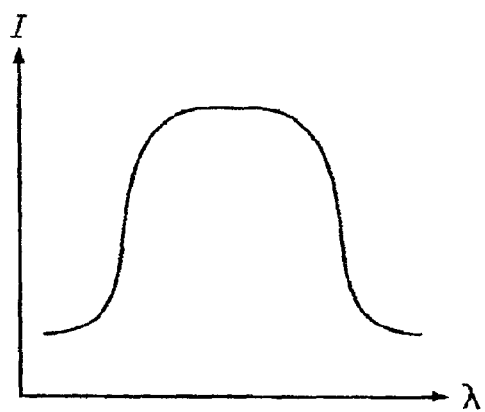
Figure 33G:
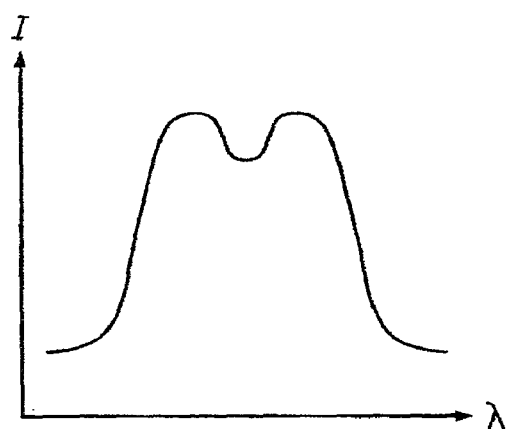

In a multiple core or multiple fiber system, for example, comprising of two or more cores or fibers, the core or fiber that is near the top of the inner cylinder or instrument (72), as illustrated in FIG. 33B, will be under tension at the bent portion or region, such that the spectral signature (Graph A in FIG. 33E) from that portion or region will exhibit longer wavelengths (region 2) as compared to the unbent or substantially straight portion (region 1). The portion of the fiber grating that is substantially straight will have a signal spectrum that is substantially unchanged in the spectral peak position (as indicated by the dashed marker line (3302) in FIG. 33E). Meanwhile the core or fiber that is near the bottom of the inner cylinder or instrument (72) will have a portion of the fiber gratings bent so that it is under compression; as such a spectral peak of region 2 is shifted toward shorter wavelengths as illustrated on Graph B in FIG. 33E. The spectral peaks for both the "top" optical fiber and "bottom" optical fiber are illustrated in 33E. As illustrated in FIG. 33E, the steering or bending was sufficient to cause complete separation between two spectral peaks (peak at region 1 and peak at region 2). However, in a different situation when only a slight bend is applied, the spectral peak may not separate into two peaks; instead, the spectral peak may broaden and not separate into two peaks as illustrated in FIG. 33F. In another situation when a slightly higher bend is applied, the spectral peak may start to separate into two peaks as illustrated in FIG. 33G. In more detail, net tension on a portion of the fiber grating will result in a broadening of the spectral profile that spreads toward longer wavelengths with respect to the unbent fiber grating spectral position. On the other hand, net compression on a portion of the fiber grating will result in broadening of the spectral profile that spreads toward the shorter wavelengths with respect to the unbent fiber grating spectral position. In summary, by analyzing spectral profiles (e.g., peaks splits or broadening of the spectral profile) the portion or fraction of the fiber grating (35) extending beyond the edge of a stiff or stiffer outer cylinder sleeve (74) may be determined or identified. The amplitude of the respective peaks depends on the respective fraction of the grating that is straight or bent. For example, if the peaks are at about the same amplitude, then the straight and bent portions of the gratings are substantially equal. In addition, the direction, e.g., tension or compression, and magnitude of the bend may be determined based on the direction of shift (e.g., longer wavelength or shorter wavelength) of the spectral profile relative to the spectral profile of an unstressed fiber.

Figure 34:
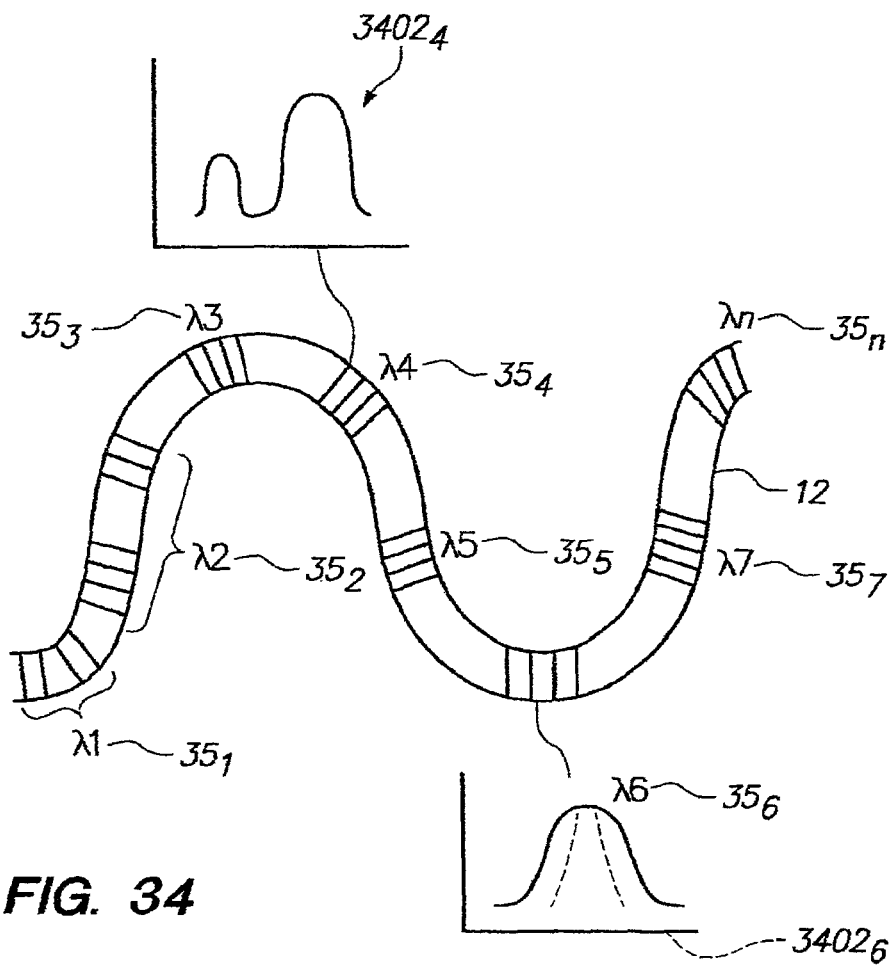
FIG. 34 illustrates how the concept of determining localized bending based on spectral profile analysis may be used to determine the shape of an elongate member.

The concepts illustrated in FIGS. 33A through 33F may be extended to a multi-core fiber or multi-fiber array offset from the neutral axis to perform continuous shape sensing. In FIG. 34, an array of fiber gratings (35) (where grating $35_1$ is configured at wavelength ($\lambda_1$), grating $35_2$ is configured at wavelength ($\lambda_2$), grating $35_3$ is configured at wavelength ($\lambda_3$), grating $35_4$ is configured at wavelength ($\lambda_4$), grating $35_5$ is configured at wavelength ($\lambda_5$), grating $35_6$ is configured at wavelength ($\lambda_6$), grating $35_7$ is configured at wavelength ($\lambda_7$), ..., grating $35_n$ is configured at wavelength ($\lambda n$)) is configured onto an optical fiber (12) to provide measurements for determining the 3-dimensional shape of the optical fiber. The fiber gratings (35) may be spaced apart such that interpolation techniques may be used. Each grating (35) will have a split or broadened spectrum depending on the radius of curvature change associated with each section of the fiber (as illustrated by the inset graph ($3402_4$) for grating ($35_4$) and inset graph ($3402_6$) for grating ($35_6$)) and each grating (35) can be monitored over an effective sub portion of its associated length on the fiber. When each of the fiber grating are subjected to axial tension or compression, the spectral position of the fiber grating may shift, similar to the discussion regarding bending as discussed above. Temperature changes may also result in spectral position shifts. For example, an increase in temperature (e.g., a positive delta) may cause the spectral position to shift towards longer wavelengths; whereas a decrease in temperature (e.g., a negative delta) may cause the spectral position to shift towards shorter wavelengths. However, uniform axial strain nor temperature changes may not result in changes in the shape of the spectral profile. Localized bending will, however, may broaden or split the spectral profile of the gratings. The degree of spectral broadening or splitting of the fiber gratings may depend on their position relative to the center line or central or neutral axis. Large offsets from the center may result in larger spectral shifts. Once the position is defined, the amount of spectral broadening will substantially depend on the direction of the bend. The shifts toward longer or shorter wavelengths depend upon whether the bending results in net tension or compression at the respective sections of the fibers where the fiber gratings are located. This may be done, for example, by using wavelength division multiplexing systems to uniquely identify each fiber gratings with its individual center wavelength and physically measuring the distance between gratings before usage. Multiple fibers are needed to define multi-dimensional bending. Two fibers that are located in an offset orientation from the central or neutral axis of the optical fiber may be sufficient for defining bending in a two-dimensional system. Three fibers may be required for a three dimensional system where twist is constrained. Additional fibers and methodologies similar to those described above associated with FIGS. 28 through 32 may be necessary to support the more general application where an elongate structure (e.g., optical fiber, etc.) is exposed to 3-dimensional bending and twisting. A variety of fiber grating sensing methods and systems may be used to support spectral measurements such as those that are based on wavelength division multiplexing and optical frequency domain reflectometry. For example, optical frequency domain reflectometry (OFDR) may be used for fiber grating arrays such as those illustrated in FIG. 34. Such arrays may be at the same or different wavelengths. Other multiplexing methods such as time division multiplexing may also be used for spectral measurements for fiber grating arrays that are at the same or different wavelengths. In addition, as will be discussed further below, fiber grating sensing methods may be combined to extend the typical sensing capabilities of a sensing system.

Figure 35:
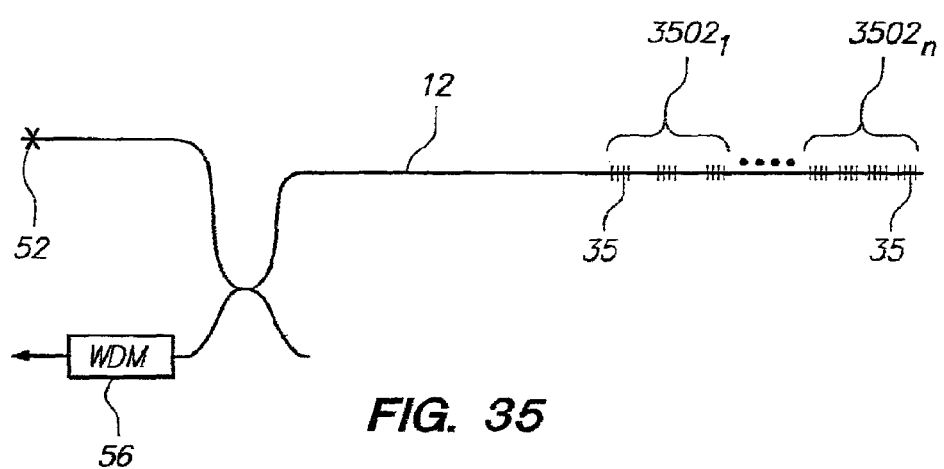
FIG. 35 illustrates a shape sensing waveform division multiplexing system.

As discussed above, a waveform division multiplexing (WDM) system may be used to process the optical data from optical fibers. Preferred embodiments of WDM systems will now be discussed in more detail. FIG. 35 illustrates a general WDM system that may be coupled to an optic fiber having unequally spaced fiber Bragg grating sensors. The WDM system includes a light source (52), such as a swept laser, optical fiber (12), fiber gratings (35), and waveform division multiplexer (56). The motivation behind the unequally spaced grating sensors is that, in reference to FIG. 35, the region specified by Band 1 ($3502_1$) may experience a rate of change of strain that is different than the rate of change of strain experienced by Band N ($3502_n$). For example, Band 1 may have a small rate of change strain and Band N may have a large rate of change. The WDM methodology only allows for a finite number of gratings as each grating utilizes a finite bandwidth of the input spectrum. In this embodiment, finite number of gratings may be used more effectively over the length of the fiber by designing the spacing of the gratings in accordance with the rate of change of strain that each section will actually be exposed. This preferred embodiment of waveform division multiplexing system may be applied to multiple single core fibers or to multiple multi-core fibers.

Figure 36:
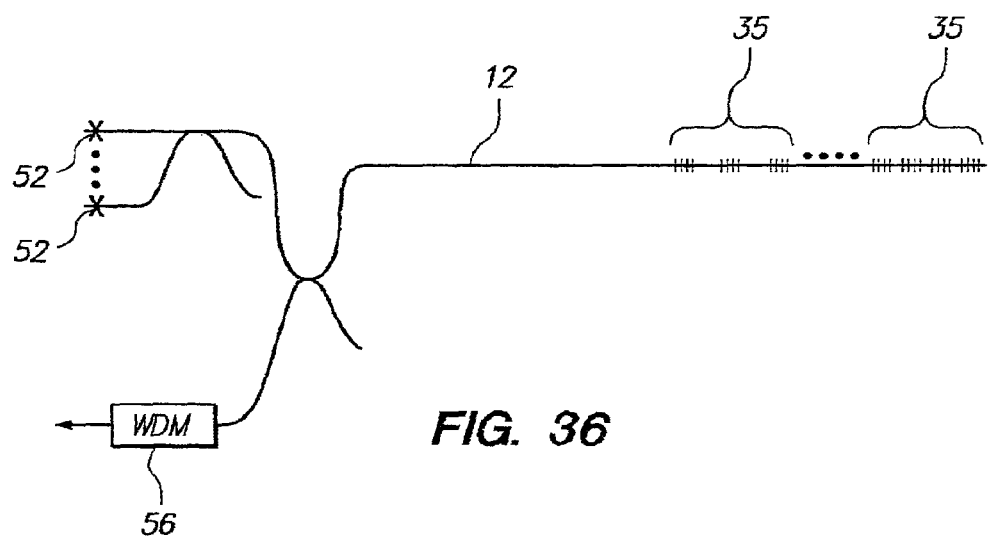
FIG. 36 illustrates another shape sensing waveform division multiplexing system.

FIG. 36 illustrates another embodiment of a waveform division multiplexing (WDM) system. In this embodiment, the WDM system includes multiple light sources (52), optical fiber (12), fiber gratings (35), and waveform division multiplexer (56). As illustrated in FIG. 36, multiple sources of light such as swept lasers may be used. Each light source (52) has a distinct frequency that sweeps over the optical fiber (12). In addition, each light source interrogates a certain band of gratings. The association of the grating to a light source is accomplished by designing each grating such that it only reflects light at a specific wavelength. The light source must emit light containing this wavelength to sense the grating. This embodiment allows for more gratings to be placed in a given length of fiber because as explained above, only a limited number of gratings can be placed and associated with each light source. Accordingly, adding multiple light sources may increase this limit. As can be appreciated, the spacing of the gratings associated with each light source does not have to be equal. Furthermore, as will be discussed in more detail, the embodiments illustrated in FIG. 35 and FIG. 36 may be combined. The embodiments illustrated in FIG. 35 and FIG. 36 may utilize multiple single core fibers or multiple multi-core fibers.

Figure 37:
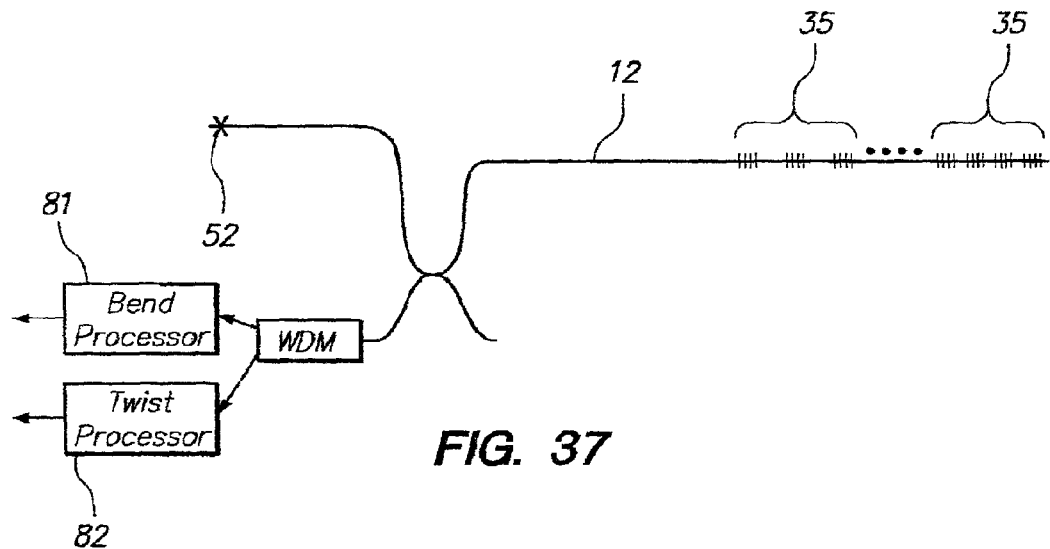
FIG. 37 illustrates yet another shape sensing waveform division multiplexing system.

FIG. 37 illustrates another embodiment of a WDM optical system which is similar to the WDM optical systems illustrated in FIG. 35 and FIG. 36. In this embodiment, the waveform division multiplexing system includes a light source (52), optical fiber (12), fiber gratings (35), waveform division multiplexer (56), bend processor (81), and twist processor (82). As configured in the optical system, the reflected light from each grating (35) may occur at specific wavelengths due to the induced strain or stress at each of the gratings (35). As such, the reflected light may be processed based on wavelength to determine bending of the optical fiber from the induced strain or stress at the gratings (35). In addition to processing the reflected light based on wavelengths, the reflected light may also be processed based on the polarization state as discussed in the previous sections to determine twist. As illustrated in FIG. 37, output of the waveform division multiplexer (56) provides input to two processors, a bend processor (81) and a twist processor (82). One wavelength band may be assigned to fiber gratings for measuring bend and another wavelength band may be assigned to support another distinct set of fiber gratings for measuring twist. Thus, by processing distinct wavelength bands independently, bend and twist may be determined.

Figure 38:
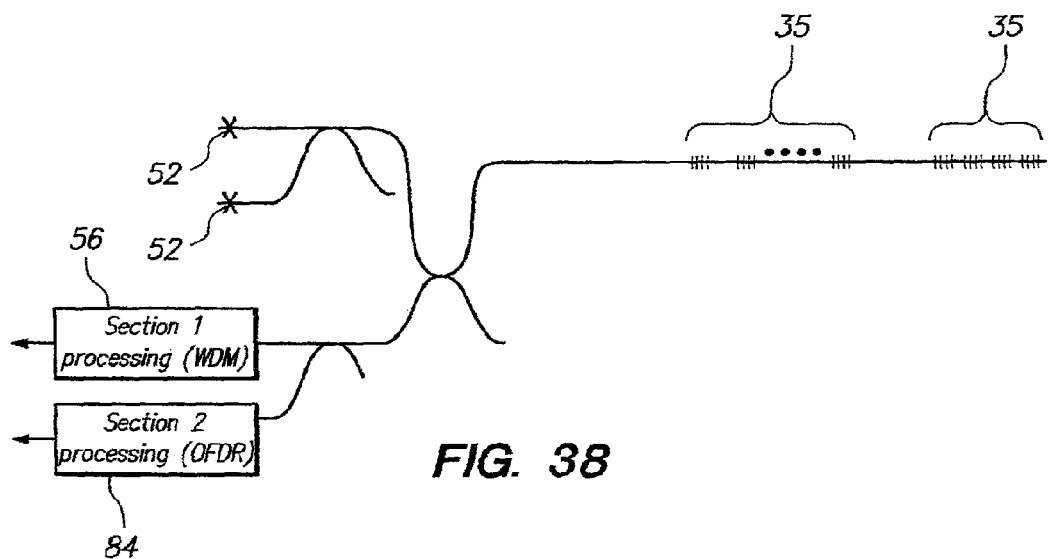
FIG. 38 illustrates a shape sensing system comprising waveform division multiplexing and optical frequency domain reflectometry processing.

As mentioned previously, fiber grating sensing methods may be combined to extend the typical sensing capabilities of a sensing system. FIG. 38 illustrates another embodiment which includes waveform division multiplexing (WDM) and optical frequency domain reflectometry (OFDR) processing. In this embodiment, the system includes two light sources (52), optical fiber (12), fiber gratings (35), WDM processor (56), and OFDR processor (84). The optical fiber (12) is designed so that it includes at least two sections, Section 1 and Section 2. One of the sections has gratings which reflect light at wavelengths that is suitable for WDM processing. Another section reflects light at a wavelength that is suitable for OFDR processing. Two sources of light are needed if the WDM approach utilizes all the bandwidth provided by one light source (e.g., a swept laser, spectrally broadband super radiant diode, or broadband fiber light source). However, it is possible to design a system using only one source of light. For example, it is possible to design a system such that part of the input spectrum is reserved for the WDM gratings and another part of the spectrum is reserved for the OFDR gratings. This could be accomplished by using a single tunable light source covering both the spectral band associated with the fiber gratings supported by WDM and the fiber gratings supported by OFDR.

Figure 39:
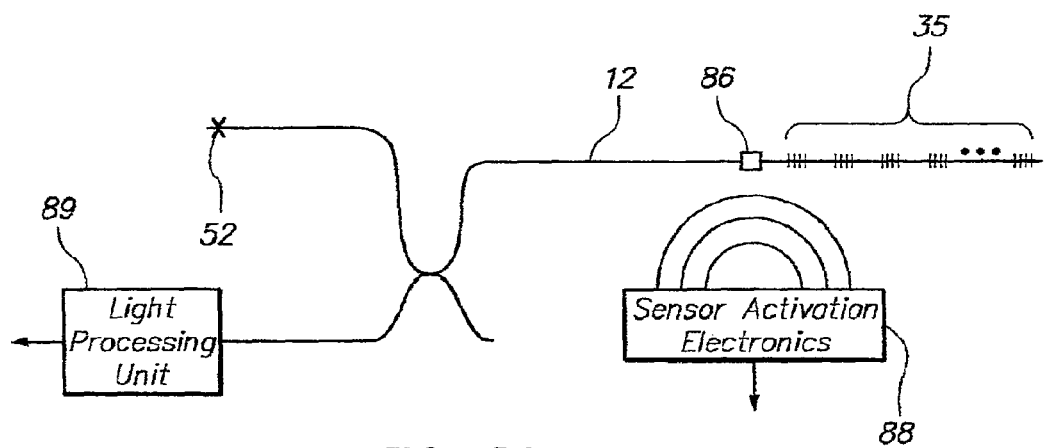
FIG. 39 illustrates a shape sensing system including optical processing and non-optical processing hardware.

FIG. 39 illustrates another embodiment in which optical sensing may be combined with non-optical sensing hardware and processing to supplement optical position and/shape sensing. In this embodiment, the system includes a light source (52), optical fiber (12), non-optical sensor (86), fiber gratings (35), sensor activation electronics (88), and light processing unit (89). The non-optical sensor (86) may be any suitable sensor such as electromagnetic type sensor, potential difference sensor, ultrasound type sensor (e.g., time-of-flight), etc. It may be desirable to measure the location of a known or designated point Q with respect to some reference point, for example point P, in relation to position or shape determined by optical fiber sensing. In position determination between points of interest, the best results may be obtained when the points are in close proximity to each other. That is the errors involved in position measurement of location Q with respect to location P may be larger if Q and P are far apart. As such, it would be desirable to keep points Q and P in close proximity to each other. As illustrated in FIG. 39, point Q may be a point located near the distal end of the optical fiber (12) or the distal end of a catheter. Point P, the location of the non-optical sensor (86) may be also located on the optical fiber (12) or the catheter at some distance from the distal end. However, in practical applications, it may be difficult or impractical to position the non-optical sensor (86) at point P in close proximity to point Q. For instance, the optical fiber (12) may be coupled to a catheter that is used in a minimally invasive interventional or diagnostic operation inside a patient. Since the non-optical sensor (86) may be physically large so that it may not be possible or easily integrated onto the optical fiber (12) or the catheter, such that the non-optical sensor (86) may be located outside the body of the patient. If the non-optical sensor is located outside of the patient, then it may be possible to use a larger sensor. Still, to get maximum accuracy of location Q, the non-optical sensor (86) should be mounted at location P where the distance between P and Q is fairly close. In addition, the location of the non-optical sensor (86) may be sensed by another non-optically based system such as EM, acoustic or electrical type technology such that the non-optical signal from sensor (86) may be easily received and processed. Accordingly, an optical fiber based measurement system may be combined with a non-optical position sensing system such that optical position and shape sensing may be supplemented by non-optical position sensing.

Figure 40A:
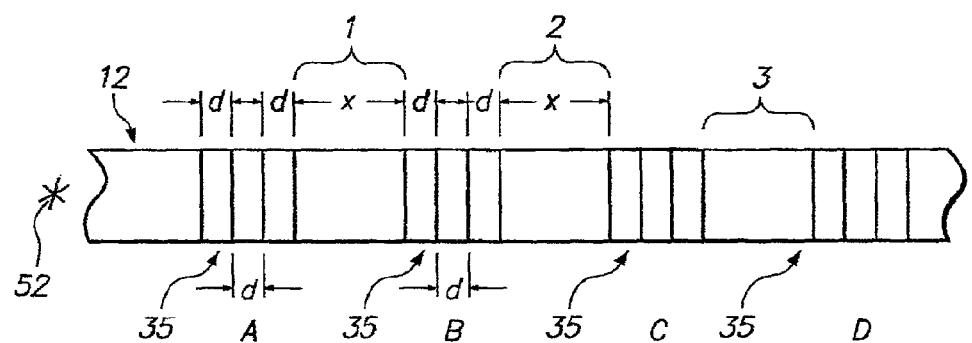
FIG. 40A illustrates an optical fiber with Bragg gratings.

Reflected light from fiber Bragg gratings may be processed using waveform or wavelength division multiplexing (WDM) or optical frequency domain reflectometry (OFDR) technique. Sometimes, a combination of both techniques may be used to process the optical data from the reflected light. For example, FIG. 40A illustrates an optical fiber (12) with Bragg gratings (35) written or printed on the length of the fiber (12) with a distance (d) between each line of the fiber gratings (35) and a distance (x) between each gratings (35). As light is launched through the optical fiber (12) by a light source (52), e.g., a swept laser, etc., light at a certain wavelength (2) is reflected back corresponding to the distance (d) between the lines of the gratings (35). As the optical fiber (12) is exposed to tension or compression due to bend, etc., the distance (d) between the lines in one or more of the gratings are altered in response to the tensile or compression load, wherein the strain (ϵ) of the fiber (12) is quotient (d'−d)/d.

$$(\epsilon)=(d'-d)/d$$

Figure 40B:
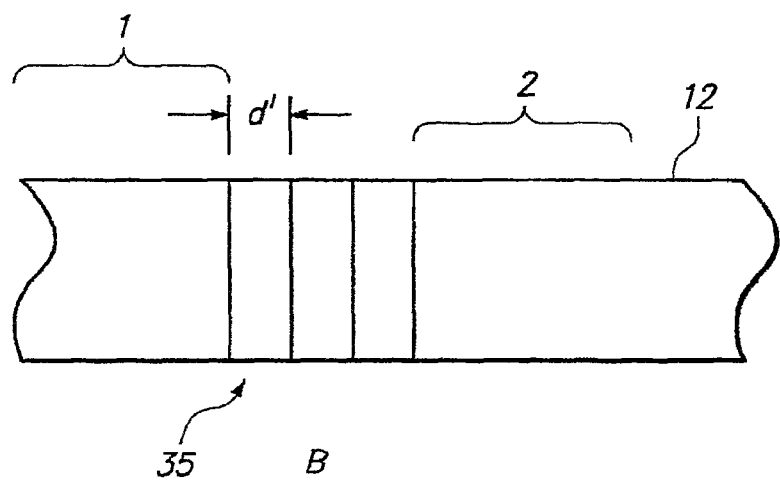
FIG. 40B illustrates a change in distance between two gratings after a load is applied to the fiber.
Figure 40C:
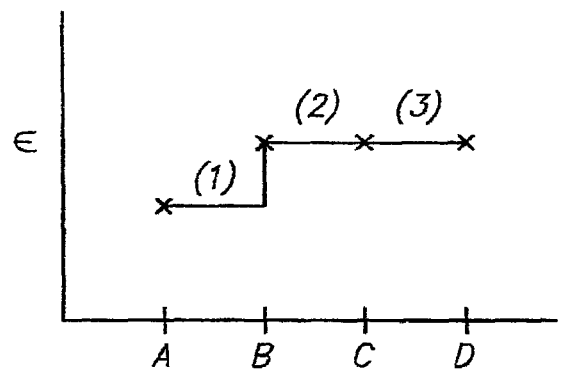
FIGS. 40C-40E illustrate a graph of strain versus distance along the length of the fiber.
Figure 40D:
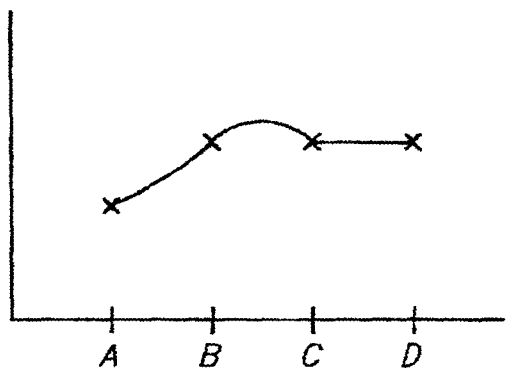
Figure 40E:
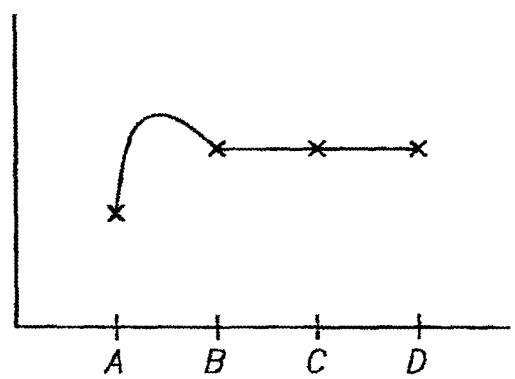

As illustrated in FIG. 40B, the distance (d') is the distance between the lines of the gratings after a load (e.g., tensile load, etc.) is applied to the fiber (12), e.g., from bending, twisting, etc. FIG. 40C illustrates a graph of strain vs. distance along the length of the fiber (12). As would be appreciated, by conventional methodologies the region (1) between the grating (A) and grating (B) is assumed to be constant in accordance with the strain measured at grating (A). Similarly, the region (2) between the grating (B) and grating (C) is assumed to be constant in accordance with the strain measured at grating (B), and the region (3) between the grating (C) and grating (D) is assumed to be constant in accordance with the strain measured at grating (C). However, in actual scenarios, the strain in region (1) is most unlikely to be at a constant value in accordance with the strain measured at grating (A). For example, as illustrated in FIG. 40D, the strain in region (1) may rise gradually between grating (A) and grating (B), or as illustrated in FIG. 40E, the strain in region (1) may rise starting at grating (A) to a peak value, and then dropping to a value below the peak value, but higher than the value measured at grating (A), such as a value measured at grating (B). As would appreciated, there are many possible scenarios for the strain profile in regions (1), (2), and (3), unless there are fiber gratings at regions (1), (2), and (3), the actual strain value or strain profile at regions (1), (2), and (3) would be unknown or uncertain. Therefore, it would be desirable to write or print gratings continuously along the length of the optical fiber (12) and use either optical frequency domain reflectometry (OFDR) technique or wavelength division multiplexing (WDM) technique or combination of OFDR and WDM techniques to process the optical data. In addition, continuous gratings could be used on each core of multi-core fibers or multiple single core fibers to characterize the dynamic 3-dimensional shape, orientation, and positions of the optical fibers. The optical fibers (e.g., multiple fibers with single core, one or more single fibers with multi-cores, etc.) may be attached in various manners to an elongate instrument, as previously discussed and illustrated (e.g., catheter, etc.), as a means to determine the dynamic 3-dimensional shape, orientation, and position of the elongate instrument or various sections or portions of the elongate instrument.

Figure 41A:
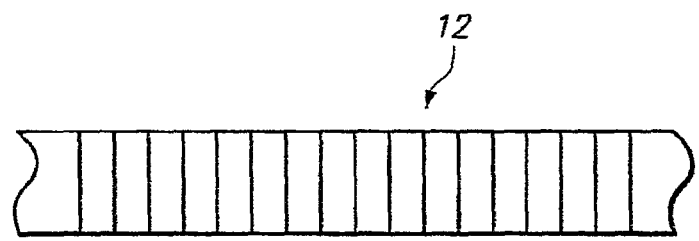
FIGS. 41A-41B illustrate an optical fiber printed with continuous Bragg gratings.
Figure 41B:
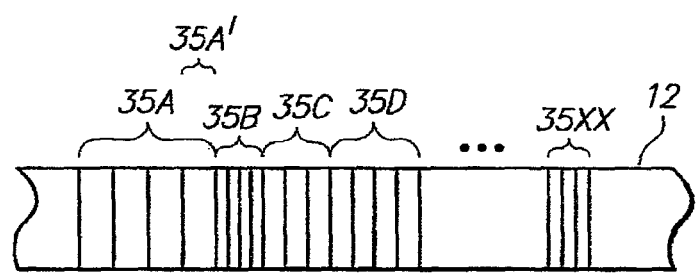

In practical applications, there may be hardware, software, and other limitations to process all the possible data that could be generated or produced by having continuous gratings along the entire length of the optical fiber for determining the strain, dynamic 3-dimensional shape, orientation, and positions of the optical fiber. In accordance with one embodiment of the present disclosure, selective scanning or selective reading of the optical data and data processing may be used to reduce the hardware, software, and processing time requirement to receive and process the necessary data for determining the strain, dynamic 3-dimensional shape, orientation, and positions of an optical fiber. As discussed herein, the reference to an optical fiber may be directed to an optical fiber having a single core or an optical fiber having multiple cores for shape sensing. As illustrated in FIG. 41A, an optical fiber (12) has been written or printed with continuous Bragg gratings. The lines of the gratings could be equal distance apart to enable the use of OFDR technique or lines of the gratings may not be equal distance apart to enable the use of WDM technique. In addition, the continuous gratings written or printed on optical fiber (12) may enable the combination of both OFDR and WDM techniques to read the strain exposed to the optical fiber. As will be discussed in more detail, the system and method for selective scanning or selective reading the optical data in accordance with one embodiment of the present disclosure may be applied to techniques that include OFDR, WDM, combination of OFDR and WDM, etc. FIG. 41B illustrates that optical fiber (12) has been written with continuous gratings; for example, some gratings (e.g., 35A, 35B, 35C, etc.) have lines that are equal distance apart, while other gratings (e.g., 35D, . . . , 35XX, etc.) have lines that are not equal distance apart. Using a selective scanning unit, embodiments of the present disclosure enable either the OFDR technique or the WDM technique to selectively scan and interrogate a fiber grating (e.g., 35A, 35B, 35C, 35D, . . . , 35XX). In addition, the selective scanning unit may scan and read gratings that overlap. As illustrated in FIG. 41B, the selective scanning unit scan and read grating 35A, 35A', etc., wherein grating 35A overlaps with grating 35B. The selective scanning unit may scan and read data from the optical fiber in any imaginable manner, e.g., overlapping, alternating, equal intervals, unequal intervals, etc., and it is not limited to the examples and illustrations provided herein.

Figure 42A:
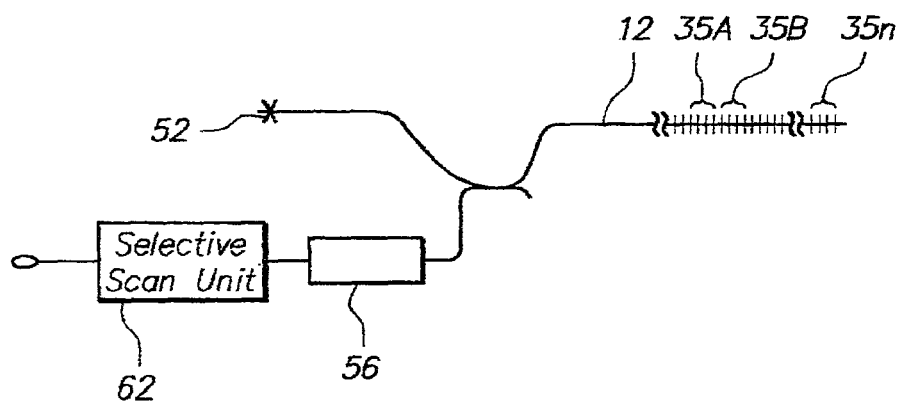
FIG. 42A illustrates a waveform division multiplexing system.
Figure 42B:
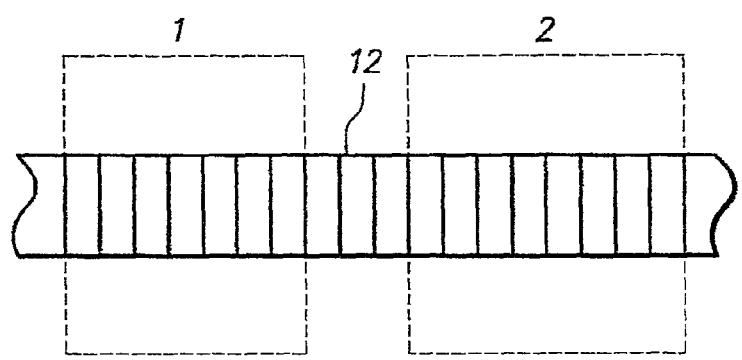
FIGS. 42B-42C illustrate selective scanning of gratings on the fiber.
Figure 42C:
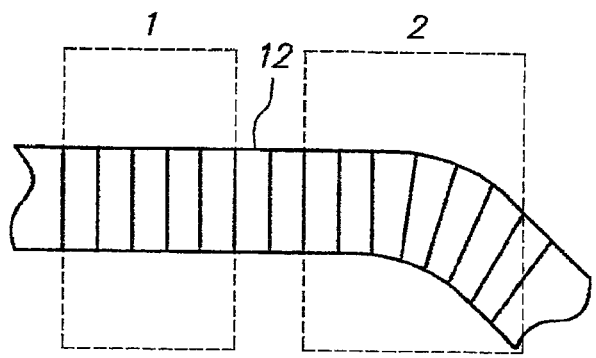

FIG. 42A illustrates a general waveform or wavelength division multiplexing (WDM) system that may be coupled to an optical fiber having Bragg gratings with unequally spaced lines with a selective scanning module in accordance with one embodiment of the present disclosure. As would be appreciated, the Bragg gratings on the optical fiber may also be written to have equally spaced lines to enable the use of OFDR technique to read the strain data from the optical fiber. Accordingly, a WDM system discussed herein may be easily changed or modified to an OFDR system as to not to limit the scope of the present disclosure to any particular technique to read strain data on an optical fiber. The optical fiber (12) in FIG. 42A may be a single fiber with a single core or a single fiber with multiple cores. As illustrated in FIG. 42, the WDM or OFDR system includes a light source (52), such as a swept laser, optical fiber (12), fiber gratings (35), waveform division multiplexer or optical frequency domain reflectometry processor (56), and selective scanning module (62). The selective scanning module (62) may be configured to selectively scan the length of optical fiber (12) and read the data from the selected grating or gratings. In accordance with one embodiment of the present disclosure, the selective scanning module (56) may selectively scan and read one section or portion of the optical fiber or selectively scan and read one section or portion of the optical fiber at a higher rate or frequency, while ignoring another section or portion of the optical fiber or selectively scan and read another section or portion of the optical fiber at a slower rate or frequency. For example, when optical fiber (12) is attached to an elongate instrument, such as a steerable elongate instrument, e.g., a manually or robotically steerable catheter, one section or portion of the elongate instrument may not change its shape, orientation, or position as often or frequently as another section or portion of the elongate instrument. As such, to conserve bandwidth on hardware and software, only the section or portion of the elongate instrument that changes its shape (e.g., bending, twisting, etc.) may be monitored or monitored more frequently. As illustrated in FIGS. 42B and 42C, the gratings in section (2) of the fiber (12) may be scan and read more frequently than the gratings in section (1) of the fiber (12).

Figure 43:
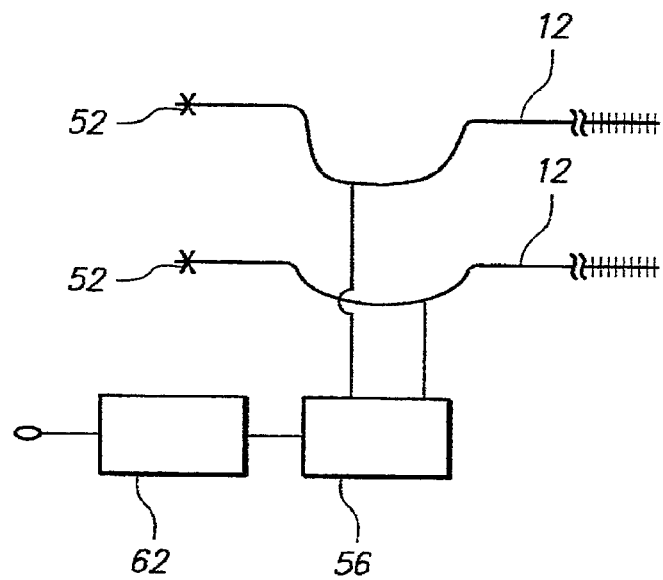
FIG. 43 illustrates an optical sensing system.

In accordance with another embodiment of the present disclosure, a WDM or an OFDR system analogous to the system of FIG. 42A may be configured to selectively scan and read two or more different fibers at different rates or frequencies. As illustrated in FIG. 43, a WDM system or OFDR system includes one or more light sources (52) (although FIG. 43 shows two light sources, the system may operate with only one light source), two optical fibers (12), a WDM or a OFDR processor (56), and selective scanning module (62). For this illustration, one of the optical fibers may be attached to one elongate instrument that is exposed to more controlled, steered, etc., movements (e.g., substantially more dynamic), while another optical fiber may be attached to another elongate instrument that is exposed to less controlled or steering movements (e.g., substantially stationary). For example, the optical fiber (12) that is exposed to more controlled or steering movements may be attached to a catheter for performing minimally invasive interventional or diagnostic operations, while the optical fiber (12) that is exposed to less controlled or steering movements or substantially stationary may be attached to a monitoring sensor or instrument for monitoring the minimally invasive interventional or diagnostic operation. To conserve hardware and software bandwidth, the selective scanning module (62) may selectively scan and read data at a higher rate or frequency from the optical fiber (12) that is exposed to more controlled or steering movements, while the selective scanning module (62) may selectively scan and read data at a lower rate or frequency from the optical fiber (12) that is exposed to less controlled or steering movements or substantially stationary.

Figure 44:
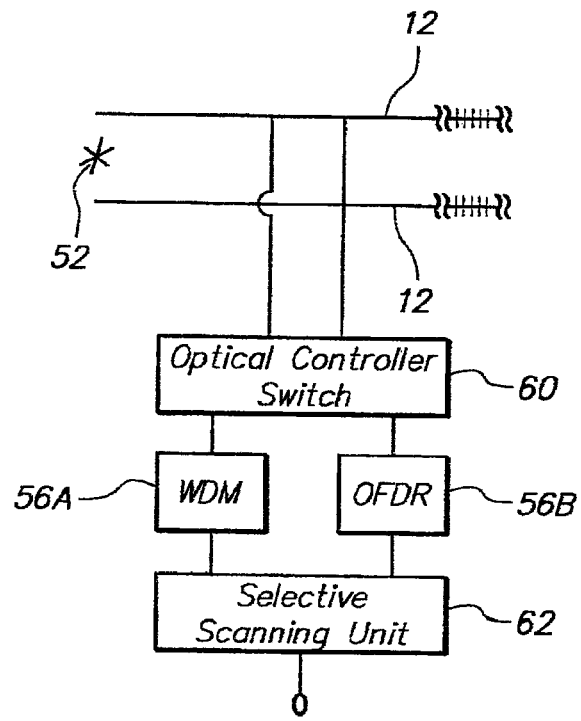
FIG. 44 illustrates another optical sensing system.

Referring to FIG. 44, it illustrates another optical sensing system in accordance with another embodiment of the present disclosure. FIG. 44 illustrates a system that may be configured to interchangeably process optical data using both WDM and/or OFDR techniques. The system includes one or multiple light sources, e.g., swept laser, etc., optical fibers (12), optical controller switch (60), WDM processor (56A), OFDR (56B), and selective scanning unit (62). This system is analogous to the system illustrated in FIG. 43 and may operates in a substantially similar manner, except this system may be configured with both a WDM processor (56A) and an OFDR processor (56B) which enables the system to selectively process the optical data with either the WDM processor or the OFDR processor.

Figure 45:
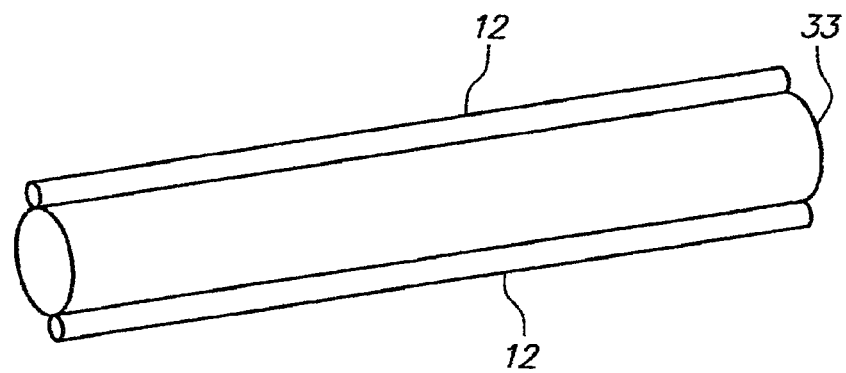
FIG. 45 illustrates two optical fibers mounted to an elongate member.
Figure 46:
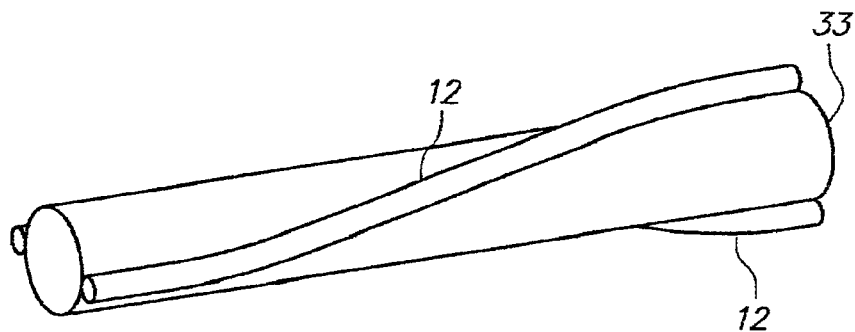
FIG. 46 illustrates two optical fibers mounted to an elongate member.
Figure 47:
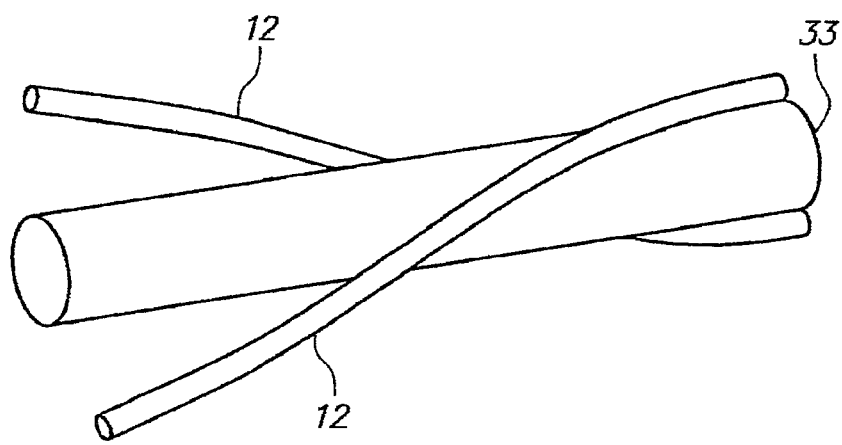
FIG. 47 illustrates the estimated 3-dimensional shapes and positions of two optical fibers.
Figure 48:
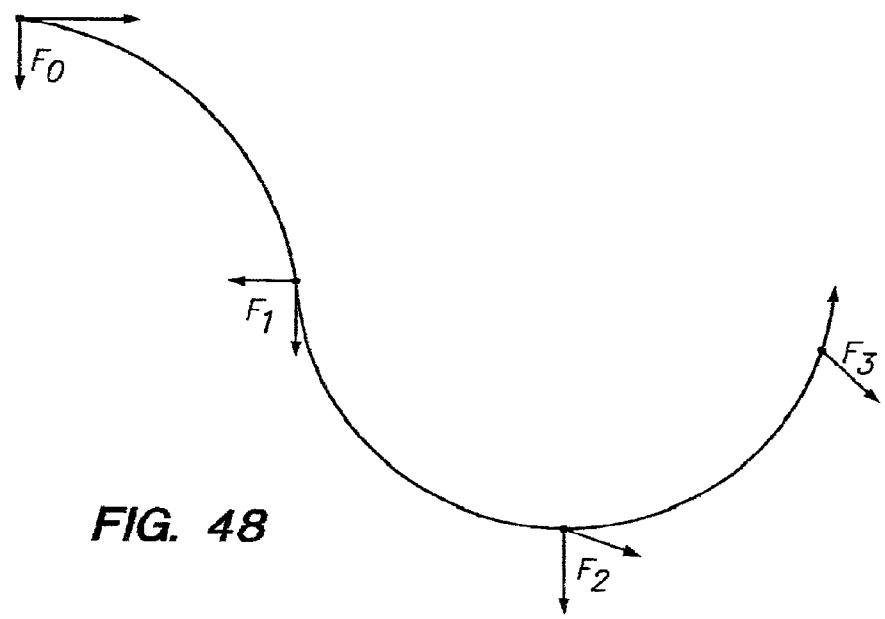
FIG. 48 illustrates the coordinate frames of various points along an optical fiber.
Figure 49:
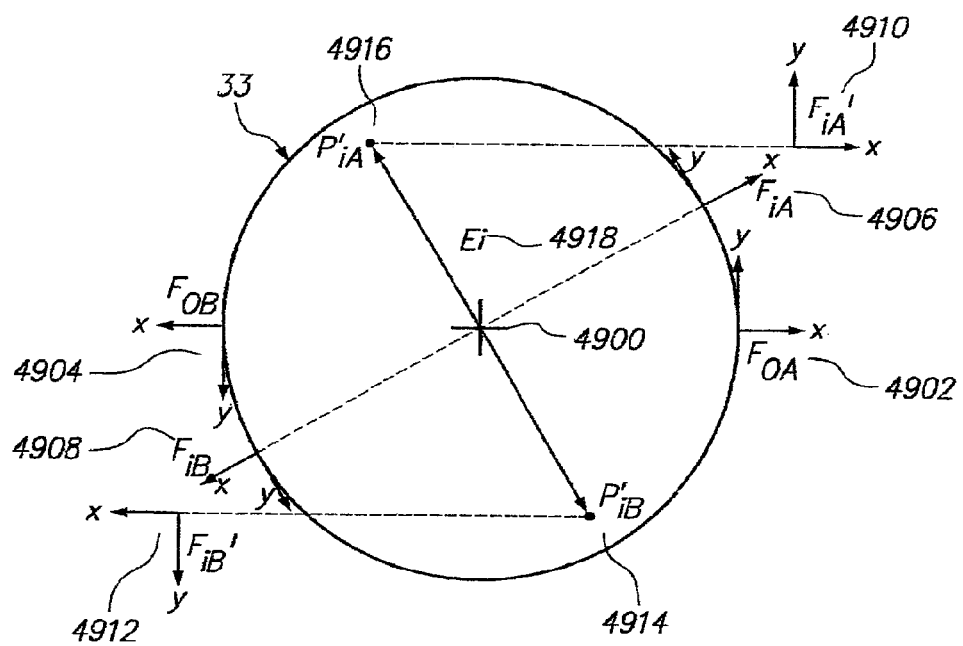
FIG. 49 illustrates the estimated error associated with the estimated shapes of two optical fibers.

Having discussed various embodiments including systems and methods for coupling one or more optical fibers (single core or multi-core fibers) such that stress or strain acting on the one or more fibers due to twist may be determined, we now refer back to FIG. 20 to discuss the hardware and software that may be implemented to estimate errors that may be caused by twist, as illustrated in Step 2010. FIG. 45 illustrates two optical fibers (12), optical fibers (12) may be single core fibers or multi-core fibers, are mounted to an elongate member (33). Twisting of the elongated member (33) may be estimated by considering the shape information obtained from multiple fibers using optical Bragg grating sensors as bending, twisting, torsion, etc. loads are applied to the elongate member while the fibers (33) are physically constrained in a specific manner on the elongate member. As the fiber are oriented on the elongate member, each fiber provides an estimate of its own shape and position in general that accounts for bending deflection, but deflection due twist may not be accounted for or taken into consideration. Therefore, the estimated shape may be different from the true shape and/or position of the fiber by some error due to twist. This error induced by twist may not be measured or determined from knowledge of the true shape and/or position of the fiber alone. However, in this case as illustrated in FIG. 45, the multiple fibers (12) are physically constrained to the elongate member (33). Accordingly, at least certain aspects of the fiber's shape and position are known. Therefore, the deviations in the estimated shapes and positions of the multiple fibers (12) from the true shapes and positions of the constrained multiple fibers (12) may be computed to determine the errors of the relative shapes and positions of the multiple fibers (12). An optimization algorithm may be used to compute an estimate of the distribution of deflection due to twist for each of the multiple fibers (12), and then apply the estimate to each of the fibers to reduce the errors of the estimated shape and positions. The optimization algorithm may be repeated to minimize the errors of the estimated shape and positions of the fibers. As illustrated in FIG. 46, elongated member (33) is twisted along with the multiple fibers (12) as the fibers (12) are mounted and physically constrained to the elongate member (33). Shape information may be obtained from each of the fibers by using the various optical fiber grating sensor techniques including hardware and software as have been discussed. Since the fibers (12) may be mounted in a configuration that is not specifically designed to directly measure information related to twist or torsional deflection, the shape information obtained may not match the actual physical shape of the constrained fibers (12). FIG. 47 illustrates the estimated shape of the fibers (12) which includes the potential expected errors of shape and position estimation. FIG. 48 illustrates the path of one of the fibers (12) as described with coordinate frame located at each of the sensor locations. The coordinate frames shifts with the deflection of the fiber (12) as the 3-dimensional shape is changed. However, since the fibers (12) are mounted in a configuration that may not be specifically designed to directly measure information related to twist or torsional deflection, the shape information obtained may not match the actual physical shape of the constrained fibers (12) and the error associated shape information also affects the orientation of the coordinate frames. In accordance with one embodiment of the present disclosure, an error optimization methodology may be used to minimize the error by using a correction factor to account for twist of the fibers (12). Error optimization may be iterated many times to reduce the error to a minimum. For example, as illustrated in FIG. 49, the reference frame $F_{OA}$ (4902) is a reference frame located at one of the sensors or optical gratings at an initial condition prior to any bending or twist is applied to the elongate member (33) or optical fiber (12). Similarly, the reference frame $F_{OB}$ (4904) is a reference frame located at another one of the sensors or optical gratings at an initial condition prior to any bending or twist is applied to the elongate member (33) or optical fiber (12). Reference frame $F_{iA}$ (4906) represents the physical reference frame $F_{OA}$ (4902) after steering movement that may include bending and/or induced or applied twist to elongate member (33) and optical fiber (12). Similarly, reference frame $F_{iB}$ (4904) represents the physical reference frame $F_{OB}$ after steering movement that may include bending and induced and/or applied twist to elongate member (33) and optical fiber (12). As illustrated, because the optical fibers (12) are physically constrained on the elongate member (33) the projects of the reference frames $F_{iA}$ (4906) and $F_{iB}$ (4908) would intersect at the center (4900) of the elongate member (33). However, as illustrated in FIG. 49, the projects of the reference frames $F_{iA}'$ and $F_{iB}'$, associated with the sensor or optical fiber gratings, located at the position and orientation based on the optical data obtained from optical fibers (12) as illustrated in FIG. 47. As illustrated in FIG. 49, the projections from reference frames $F_{iA}'$ and $F_{iB}'$ most likely do not intersect near or at the center (4900) of the elongate member (33). Instead, the projections are at a distance $E_i$ (4918) apart. The distance $E_i$ (4918) of the projected centers $P'_{iA}$ (4914) and $P'_{iB}$ (4916) would be the error caused by not accounting for induced twist in the shape estimation for the fibers (12). Accordingly, a correction factor, e.g., a twist correction factor, could be calculated to reduce the distance $E_i$ (4918) based on the deviation of the estimated shape and position of the fibers (12) to the true or actual shape and positions of the constrained fibers (12). The correction factor could be refined through iteration by using error optimization to minimize the error $E_i$ (4918). Thereby, a correction factor or twist correction factor may be determined to improve the estimated 3-dimensional shape of the fibers.

While multiple embodiments and variations of the many aspects of the present disclosure have been disclosed and described herein, such disclosure is provided for purposes of illustration only. Many combinations and permutations of the disclosed system are useful in minimally invasive medical intervention and diagnosis, and the system is configured to be flexible. The foregoing illustrated and described embodiments of the present disclosure are susceptible to various modifications and alternative forms, and it should be understood that the present disclosure generally, as well as the specific embodiments described herein, are not limited to the particular forms or methods disclosed, but also cover all modifications, equivalents and alternatives. Further, the various features and aspects of the illustrated embodiments may be incorporated into other embodiments, even if no so described herein, as will be apparent to those skilled in the art.

What is claimed is:

1. A method for measuring bending, the method comprising:
  receiving a reflected signal from a strain sensor provided on an optical fiber;
  determining a spectral profile of the reflected signal; and
  determining bending of the optical fiber based on a comparison of the spectral profile of the reflected signal with a predetermined spectral profile,
  wherein the determining bending of the optical fiber is based on separation of the spectral profile of the reflected signal into spectral peaks and/or broadening of the spectral profile of the reflected signal relative to the predetermined spectral profile.

2. The method of claim 1, further comprising determining a magnitude of bending based on whether the spectral profile of the reflected signal has a plurality of peaks.

3. The method of claim 2, wherein the spectral profile comprises a first peak and a second peak, and wherein the determining the magnitude of bending further comprises comparing an amplitude of the first peak with an amplitude of the second peak.

4. The method of claim 1, wherein the comparison of the spectral profile of the reflected signal with the predetermined spectral profile comprises determining whether the spectral profile of the reflected signal is broader than the predetermined spectral profile.

5. The method of claim 1, wherein the strain sensor is a first strain sensor, the reflected signal is a first reflected signal, and wherein the method further comprises:
  receiving a second reflected signal from a second strain sensor provided on the optical fiber;
  determining a spectral profile of the second reflected signal; and determining bending of the optical fiber based on the spectral profile of the first reflected signal and the spectral profile of the second reflected signal, wherein a center wavelength of the spectral profile of the first reflected signal is different than a center wavelength of the spectral profile of the second reflected signal.

6. A method for measuring bending, the method comprising:
receiving a reflected signal from a strain sensor provided on an optical fiber;
determining a spectral profile of the reflected signal; and
determining bending of the optical fiber based on a comparison of the spectral profile of the reflected signal with a predetermined spectral profile,
wherein the optical fiber is combined with an elongated flexible instrument,
wherein the optical fiber is offset from a neutral axis of the elongated flexible instrument, and
wherein the determining bending of the optical fiber further comprises determining whether a portion of the optical fiber has undergone compression or whether the portion has undergone tension.

7. The method of claim 6, wherein the determining whether the portion has undergone compression comprises determining whether the spectral profile of the reflected signal has shifted toward a shorter wavelength relative to the predetermined spectral profile, and
wherein the determining whether the portion has undergone tension comprises determining whether the spectral profile of the reflected signal has shifted toward a longer wavelength relative to the predetermined spectral profile.

8. The method of claim 6, wherein the optical fiber is a first optical fiber, and wherein the method further comprises:
receiving a reflected signal from a strain sensor provided on a second optical fiber combined with the elongated flexible instrument;
determining a spectral profile of the reflected signal from the strain sensor provided on the second optical fiber;
determining bending of the second optical fiber based on the spectral profile of the reflected signal from the strain sensor provided on the second optical fiber, wherein a center wavelength of the spectral profile of the reflected signal of the first optical fiber is the same as a center wavelength of the spectral profile of the reflected signal of the second optical fiber.

9. A method for measuring bending, the method comprising:
receiving a reflected signal from a strain sensor provided on an optical fiber;
determining a spectral profile of the reflected signal;
determining bending of the optical fiber based on a comparison of the spectral profile of the reflected signal with a predetermined spectral profile; and determining a temperature of the optical fiber based on the spectral profile of the reflected signal.

10. The method of claim 9, wherein the determining the temperature comprises:
determining that the temperature has increased if the spectral profile has shifted towards a longer wavelength relative to the predetermined spectral profile; and
determining that the temperature has decreased if the spectral profile has shifted towards a shorter wavelength relative to the predetermined spectral profile.

11. An instrument system comprising:
an optical fiber having a strain sensor provided thereon;
a detector operatively coupled to the optical fiber and configured to receive a reflected signal from the strain sensor;
a controller operatively coupled to the detector and configured to:
determine a spectral profile of the reflected signal received by the detector, and
determine bending of the optical fiber based on a comparison of the spectral profile of the reflected signal with a predetermined spectral profile,
wherein the controller is configured to determine the bending of the optical fiber based on separation of the spectral profile of the reflected signal into spectral peaks and/or broadening of the spectral profile of the reflected signal relative to the predetermined spectral profile.

12. The instrument system of claim 11, wherein the controller is further configured to determine a magnitude of bending based on whether the spectral profile of the reflected signal has a plurality of peaks.

13. The instrument system of claim 12, wherein the spectral profile comprises a first peak and a second peak, and wherein the controller is further configured to determine the magnitude of bending by comparing an amplitude of the first peak with an amplitude of the second peak.

14. The instrument system of claim 11, wherein the controller is configured to determine bending by determining whether the spectral profile of the reflected signal is broader than the predetermined spectral profile.

15. The instrument system of claim 11, wherein the reflected signal is a first reflected signal and wherein the strain sensor is a first strain sensor, and
wherein the detector is further configured to receive a second reflected signal from a second strain sensor provided on the optical fiber,
wherein the controller is configured to determine a spectral profile of the second reflected signal, and
wherein the controller is configured to determine bending of the optical fiber based on the spectral profile of the first reflected signal and the spectral profile of the second reflected signal, wherein a center wavelength of the spectral profile of the first reflected signal is different than a center wavelength of the spectral profile of the second spectral profile.

16. An instrument system comprising:
an optical fiber having a strain sensor provided thereon;
a detector operatively coupled to the optical fiber configured to receive a reflected signal from the strain sensor;
a controller operatively coupled to the detector and configured to:
determine a spectral profile of the reflected signal received by the detector, and
determine bending of the optical fiber based on a comparison of the spectral profile of the reflected signal with a predetermined spectral profile,
wherein the optical fiber is combined with an elongated flexible instrument,
wherein the optical fiber is offset from a neutral axis of the elongated flexible instrument, and
wherein the controller is further configured to determine whether a portion of the optical fiber located at the strain sensor has undergone bending by determining whether the portion has undergone compression or whether the portion has undergone tension.

17. The medical instrument system of claim 16, wherein the controller is further configured to determine whether the portion has undergone compression by determining whether the spectral profile of the reflected signal has shifted toward a shorter wavelength relative to the predetermined spectral profile, and wherein the controller is configured to determine whether the portion has undergone tension by determining whether the spectral profile of the reflected signal has shifted toward a longer wavelength relative to the predetermined spectral profile.

18. The instrument system of claim 16, wherein the optical fiber is a first optical fiber, and wherein the controller is further configured to determine a spectral profile of a reflected signal from a strain sensor provided on a second optical fiber combined with the elongated flexible instrument, and determine bending of the second optical fiber based on the spectral profile of the reflected signal from the strain sensor provided on the second optical fiber, wherein a center wavelength of the spectral profile of the reflected signal of the first optical fiber is the same as a center wavelength of the spectral profile of the reflected signal of the second optical fiber.

19. An instrument system comprising:

an optical fiber having a strain sensor provided thereon;

a detector operatively coupled to the optical fiber and configured to receive a reflected signal from the strain sensor;

a controller operatively coupled to the detector and configured to:

determine a spectral profile of the reflected signal received by the detector, and determine bending of the optical fiber based on a comparison of the spectral profile of the reflected signal with a predetermined spectral profile, wherein the controller is further configured to determine a temperature of the optical fiber based on the spectral profile of the reflected signal.

20. The instrument system of claim 19, wherein the controller is configured to determine the temperature by determining a temperature increase if the spectral profile has shifted towards a longer wavelength relative to the predetermined spectral profile; and determining a temperature decrease if the spectral profile has shifted towards a shorter wavelength relative to the predetermined spectral profile.

21. A method for measuring bending, the method comprising:

receiving a reflected signal from a strain sensor provided on an optical fiber;

determining a spectral profile of the reflected signal; and determining bending of the optical fiber based on a comparison of the spectral profile of the reflected signal with a predetermined spectral profile, wherein the determining bending of the optical fiber is based on the direction of shift of spectral profile of the reflected signal relative to the predetermined spectral profile.

22. The method of claim 21, wherein the determining bending of the optical fiber comprises determining the direction of the bending.

23. An instrument system comprising:

an optical fiber having a strain sensor provided thereon;

a detector operatively coupled to the optical fiber and configured to receive a reflected signal from the strain sensor;

a controller operatively coupled to the detector and configured to:

determine a spectral profile of the reflected signal received by the detector, and determine bending of the optical fiber based on a comparison of the spectral profile of the reflected signal with a predetermined spectral profile, wherein the controller is configured to determine the bending of the optical fiber based on the direction of shift of spectral profile of the reflected signal relative to the predetermined spectral profile.

24. The instrument system of claim 23, wherein the controller is configured to determine the direction of the bending based on the direction of shift of spectral profile of the reflected signal relative to the predetermined spectral profile.

* * * * *